United States Patent
Chen et al.

(10) Patent No.: US 9,512,106 B2
(45) Date of Patent: Dec. 6, 2016

(54) SMOOTHENED MODULATORS AND METHODS OF USE THEREOF

(71) Applicant: Duke University, Durham, NC (US)

(72) Inventors: Wei Chen, Durham, NC (US); Jiangbo Wang, Durham, NC (US); Robert A. Mook, Jr., Durham, NC (US); Lawrence S. Barak, Durham, NC (US); H. Kim Lyerly, Durham, NC (US); Anthony Angelo Ribeiro, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/405,614

(22) PCT Filed: Sep. 16, 2013

(86) PCT No.: PCT/US2013/059905
§ 371 (c)(1),
(2) Date: Dec. 4, 2014

(87) PCT Pub. No.: WO2014/043608
PCT Pub. Date: Mar. 20, 2014

(65) Prior Publication Data
US 2015/0166509 A1 Jun. 18, 2015

Related U.S. Application Data

(60) Provisional application No. 61/701,960, filed on Sep. 17, 2012.

(51) Int. Cl.
C07D 401/14 (2006.01)
C07D 401/12 (2006.01)
C12N 5/0793 (2010.01)

(52) U.S. Cl.
CPC ........... C07D 401/14 (2013.01); C07D 401/12 (2013.01); C12N 5/0619 (2013.01); *C12N 2500/46* (2013.01)

(58) Field of Classification Search
CPC .................................................... C07D 401/14
USPC ......... 514/316; 546/194; 544/121, 122, 124, 544/460
See application file for complete search history.

(56) References Cited

U.S. PATENT DOCUMENTS

2008/0269215 A1 10/2008 Goldsmith et al.
2011/0046143 A1 2/2011 Hipskind et al.

FOREIGN PATENT DOCUMENTS

WO WO 03/086397 A1 10/2003
WO WO 2006/028958 A2 3/2006
WO WO 2009/154739 A2 12/2009

OTHER PUBLICATIONS

Improper Markush "Fed. Registry" p. 7162-7175, training slides 1, 64-67 (2011).*
Ester , Wikipedia p. 1-11 (2016).*
Sulfonamaide, Wikipedia p. 1-4 (2016).*
Roth et al. "Piperieine derivatives . . . "*
Cerebellum granule cell, Wikipedia p. 1-2 (2016).*
(Continued)

*Primary Examiner* — Celia Chang
(74) *Attorney, Agent, or Firm* — Myers Bigel, P.A.

(57) ABSTRACT

Compounds of general Formulas (I), (IA), (IB) are described, along with compositions containing the same and methods of use thereof, inhibiting the hedgehog pathway in a cell or inhibiting unwanted proliferation of a cell.

25 Claims, 4 Drawing Sheets

(56) References Cited

OTHER PUBLICATIONS

Wang et al. "Identification of a novel Smoothened antagonist that potently suppresses Hedgehog signaling" *Bioorganic & Medicinal Chemistry* 20:6751-6757 (2012).
International Search Report and Written Opinion, PCT/US2013/059905, mailed Feb. 18, 2014.
PUBChem CID 71458712 (Create Date: May 30, 2013) 2 pages.

* cited by examiner

A.

Tripos 3910

Compound A8

B.

SMOOTHENED MODULATORS AND METHODS OF USE THEREOF

RELATED APPLICATIONS

This application is a 35 U.S.C. §371 national phase entry of PCT Application PCT/US2013/059905, filed Sep. 16, 2013, and published in English on Mar. 20, 2014, as International Publication No. WO 2014/043608, and which claims the benefit of U.S. Provisional Application No. 61/701,960, filed Sep. 17, 2012, the disclosure of each of which is incorporated herein by reference in its entirety.

STATEMENT OF GOVERNMENT SUPPORT

This invention was made with Government support under grant numbers 5RO1 CA113656-03 from the National Institutes of Health and 5K12-CA100639-08 from the National Institutes of Health. The US Government has certain rights to this invention.

BACKGROUND OF THE INVENTION

The evolutionarily conserved Hedgehog (Hh) signaling pathway is essential for embryonic development, tissue homeostasis, and maintenance of self-renewal potential in adult stem cells[1-3]. An increasing body of evidence has shown that key components of the pathway: Hh protein, its receptor Patched (Ptc) and an effector receptor Smoothened (Smo), also play pivotal roles in the development of numerous cancers[3,4]. For example, dysregulation of Hh signaling, resulting from mutations in components of the pathway has been directly implicated in the development of basal cell carcinoma and medulloblastoma[6-10]. High levels of pathway activity are observed in cancers of the pancreas, proximal gastrointestinal tract, and prostates[11-13]. In mice, about 14-30% of Ptc heterozygous knockout mice develop medulloblastoma and the homozygous deletion of Ptc in GFAP-positive progenitor cells resulted in the development of medulloblastoma in 100% of genetically engineered mice[14-15].

Several small molecule inhibitors of the pathway that bind the Smo receptor, such as cyclopamine, IPI-926, and GDC-0449, have been identified with a number of inhibitors under investigation in clinical trials[16-21,49]. Among these inhibitors, GDC-0449 (Vismodegib) was recently approved by the FDA to treat patients with advanced basal cell carcinoma[22-24]. Unfortunately, acquired resistance to GDC-0449 was recently described in which an Asp to His point mutation (D473H) was found in the Smo gene. The Smo-D473H mutant receptor is refractory to inhibition by GDC-0449 due to loss of interaction between the drug and receptor[17,25]. Thus, new Smo inhibitors with pharmacological properties capable of inhibiting wild-type and clinically relevant mutant receptors are needed to overcome acquired drug resistance and extend the duration of response.

A mechanistic understanding of the Hh signaling pathway has evolved over the past decade[26]. The Hedgehog family of growth factor proteins is comprised of 3 members: Sonic Desert, and Indian Hedgehog, each known to bind the transmembrane receptor Ptc. In the resting, non-ligand bound state, the unoccupied transmembrane receptor Ptc inhibits the activity of the transmembrane protein Smo. Upon binding of Hh ligand to its receptor Ptc, Smo becomes activated and transduces signaling by activating Gli transcription factors that results in the modulation of Hh responsive genes such as Myc and Ptc.

U.S. Pat. No. 8,178,563 to Gao et al. describes compounds and compositions as hedgehog pathway modulators, and therapeutic methods of use thereof.

SUMMARY OF THE INVENTION

A first aspect of the present invention is compounds (sometimes also referred to as "active compounds" herein) of Formula I, IA or IB:

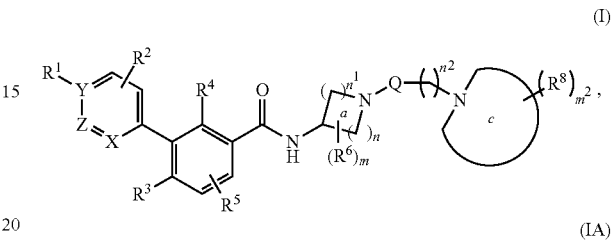

wherein:
X ix C or N;
Y is C or N;
Z is C or N;
ring C is, with the associated N, a heterocyclo group;
R, $R^1$, $R^2$, $R^3$, $R^4$, $R^5$ each $R^6$, each $R^7$, and each $R^8$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;
  subject to the proviso that $R^1$ is absent when Y is N;
  Q is heteroaryl, preferably pyridyl;
  m, $m^1$, and $m^2$ are each integers of zero, 1, 2 or 3;
  n is an integer of from zero or 1 to 7, preferably 2;
  $n^1$ is an integer of from one to six, preferably 2;
  $n^2$ is an integer of 1, 2 or 3;
or a pharmaceutically acceptable salt thereof.

A further aspect of the present invention is a composition comprising an active compound as described herein in a pharmaceutically acceptable carrier.

A further aspect of the present invention is a method of inhibiting the hedgehog pathway in a cell, comprising contacting the cell with an active compound as described herein A further aspect of the present invention is a method for inhibiting unwanted proliferation of a cell, comprising contacting the cell with an active compound as described herein.

The present invention is explained in greater detail in the drawings herein and the specification set forth below.

DETAILED DESCRIPTION OF PREFERRED EMBODIMENTS

Figure 1:
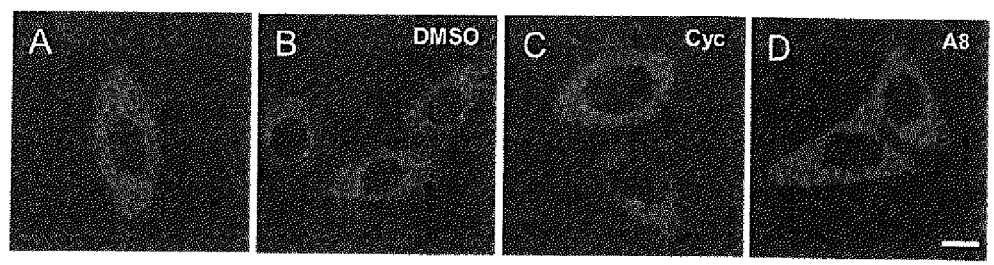
FIG. 1. Identification of novel Smo inhibitors in U2OS cells. Inhibitors are detected by the homogenous distribution of the green punctate pattern that results when the intracellular association of βarr2-GFP with Smo is inhibited. Confocal images of U2OS cells stably expressing (A) βarr2-GFP alone, or (B-D) βarr2-GFP co-expressed with Smo-633. Cells were treated for 6 hours with DMSO (B); 5 µM cyclopamine (Cyc) (C); or 5 µM compound A8 (D). Scale bar: 10 µm.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O), cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkylene bridge" as used herein refers to a straight or branched chain hydrocarbon bridging species containing from 1 to 10 carbon atoms. Representative examples include, but are not limited to, C1-C5 bridges such as —(CH$_2$)$_n$— where n is 1 or 2 to 3, 4 or 5. The term "alkylene bridge" is intended to include both substituted and unsubstituted unless otherwise indicated and may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Thus the term "alkyl" is specifically intended to include haloalkyl such as fluoroalkyl (e.g., —CH$_2$F, —CHF$_2$, —CH$_2$CF$_3$, etc.), and specifically intended to include perhaloalkyl such as perfluoroalkyl (e.g., —CF$_3$, —CF$_2$CF$_3$, etc.).

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkynyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. Bicyclic and tricyclic ring systems are also included. These rings may be optionally substituted with additional substituents as described herein such as halo or loweralkyl. The term "cycloalkyl" is generic and intended to include heterocyclic groups as discussed below unless specified otherwise.

"Heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. In some embodiments aryl contains a "hetero" atom and is also a "heterocyclo" group as described above. The term "aryl" is intended to include both substituted and unsubstituted aryl unless otherwise indicated and these groups may be substituted with the same groups as set forth in connection with alkyl and loweralkyl above. More specifically, "aryl" groups as used herein may be substituted 1, 2, 3, or 4 or more times with independently selected halo (e.g., haloaryl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Arylaryl" refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Any "aryl" may be used, substituted or unsubstituted, and optionally containing a heteroatom, as described above. Typical arylaryl groups include, but are not limited to, biphenyl, triphenyl, phenyl-naphthyl, binaphthyl, biphenyl-naphthyl, and the like, which may be substituted or unsubstituted as described in connection with aryl above. Where the number of carbon atoms in an arylaryl group are specified, the numbers refer to the carbon atoms comprising each parent aromatic ring. For example, ($C_5$-$C_{14}$) arylaryl is an arylaryl group in which each aromatic ring comprises from 5 to 14 carbons, e.g., biphenyl, triphenyl, binaphthyl, phenylnaphthyl, etc. Preferably, each parent aromatic ring system of an arylaryl group is independently a ($C_5$-$C_{14}$) aromatic, more preferably a ($C_5$-$C_{10}$) aromatic. In some embodiments, preferred are arylaryl groups in which all of the parent aromatic ring systems are identical, e.g., biphenyl, triphenyl, binaphthyl, trinaphthyl, etc. See, e.g., U.S. Pat. No. 6,750,199.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like. Thus the term "alkoxy" is specifically intended to include haloalkoxy such as fluoroalkoxy (e.g., —OCH$_2$F, —OCHF$_2$, —OCH$_2$CF$_3$, etc.), and specifically intended to include perhaloalkoxy such as perfluoroalkoxy (e.g., —OCF$_3$, —OCF$_2$CF$_3$, etc.).

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Diol" as used herein refers to a chemical compound containing two hydroxyl groups.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Treat" as used herein refers to any type of treatment that imparts a benefit to a patient afflicted with a disease or disorder, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Treat" as used herein refers to any type of treatment that imparts a benefit to a patient afflicted with a disease or disorder, including improvement in the condition of the patient (e.g., in one or more symptoms), delay in the progression of the disease, etc.

"Cancer" as used herein may be any type of cancer, including but not limited to lung cancer, colon cancer, colorectal cancer, breast cancer, prostate cancer, ovarian cancer, liver cancer, leukemia, lymphoma, etc.

"Pharmaceutically acceptable" as used herein means that the compound or composition is suitable for administration to a subject to achieve the treatments described herein, without unduly deleterious side effects in light of the severity of the disease and necessity of the treatment.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes.

1. Active Compounds.

As noted above, the present invention provides compounds of Formula I, IA or IB:

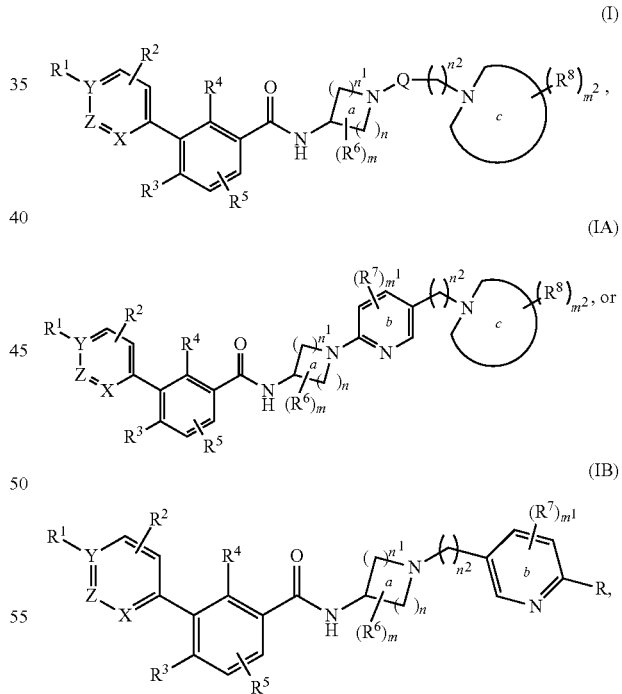

wherein:
X ix C or N;
Y is C or N;
Z is C or N;
ring c is, with the associated N, a heterocyclo group (e.g., ring c is selected from the group consisting of piperidinyl, piperazinyl, pyrrolidinyl, pyrrolinyl; imidazolidinyl, pyrazolidinyl, morpholinyl; thiomorpholinyl, etc.)

R, $R^1$, $R^2$, $R^3$, $R^4$, $R^5$ each $R^6$, each $R^7$, and each $R^8$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

subject to the proviso that $R^1$ is absent when Y is N;

Q is heteroaryl, preferably pyridyl;

m, $m^1$, and $m^2$ are each integers of zero, 1, 2 or 3;

n is an integer of from zero or 1 to 7, preferably 2;

$n^1$ is an integer of from one to six, preferably 2;

$n^2$ is an integer of 1, 2 or 3;

or a pharmaceutically acceptable salt thereof.

In some embodiments, X is C, Y is C, and Z is N; or X is C, Y is N, and Z is C; or X is N, Y is C, and Z is C.

In some embodiments, X is N, Y is N, and Z is C; or X is N, Y is C, and Z is N; or X is C, Y is N, and Z is N.

In some embodiments, the compound has the structure of Formula IB and R is heterocyclo.

In some embodiments, R is selected from the group consisting of:

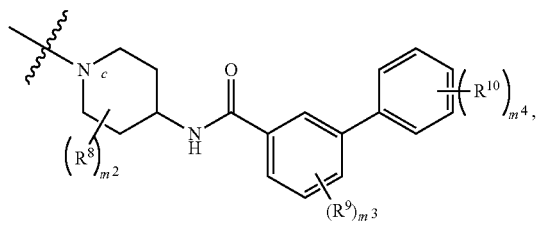

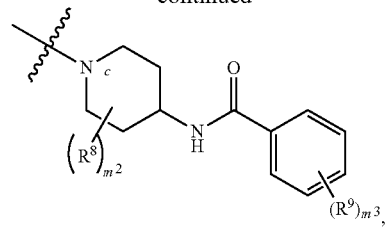

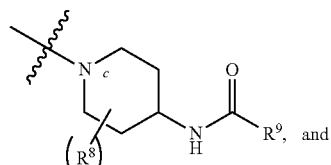

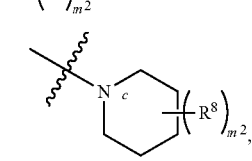

wherein:

each $R^8$ and $m^2$ is as given above;

$m^3$ and $m^4$ are each independently an integer of zero, 1, 2 or 3;

$R^9$ and each R' is each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy.

In some embodiments, the compound has the structure of Formula IIA or Formula IIB:

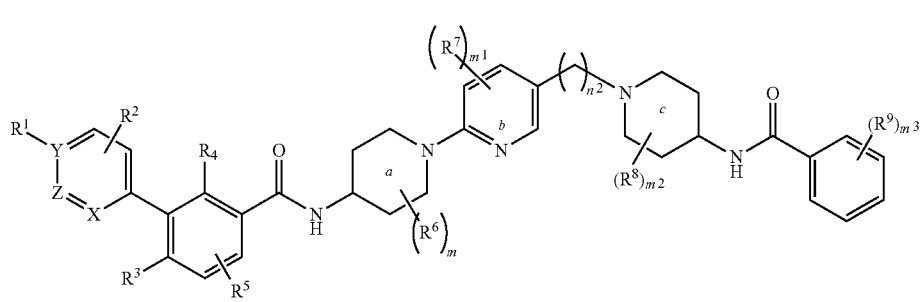

(IIA)

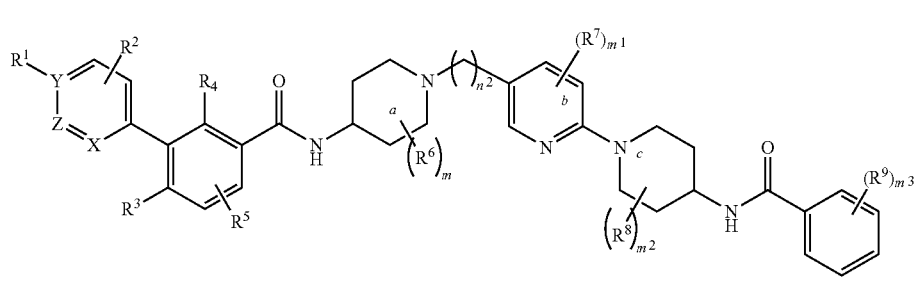

(IIB)

where $m^3$ is an integer of zero, 1, 2 or 3; and each $R^9$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy.

In some embodiments, R is selected from the group consisting of H, alkyl, cycloalkyl, cycloalkylalkyl, heterocyclo, heterocycloalkyl, heterocycloalkenylaryl, arylalkyl, arylalkenyl, arylalkynyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, urea, alkoxylacylamino, and aminoacyloxy. Or more particularly, R is selected from the group consisting of H, alkyl, heterocyclo, heterocycloalkyl, heterocycloalkenylaryl, arylalkyl, heteroaryl, heteroarylalkyl, alkoxyacyl, aryloxy, amino, alkylamino, arylalkylamino, disubstituted amino, acylamino, acyloxy, ester, amide, sulfoxyl, sulfonyl, sulfonamide, urea, alkoxylacylamino, and aminoacyloxy.

In some embodiments, $R^1$ is selected from the group consisting of H, alkyl, cycloalkyl, cycloalkylalkyl, cycloalkylalkenyl, heterocyclo, heterocycloalkyl, heterocycloalkenyl, aryl, arylalkyl, arylalkenyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy. Or more particularly, $R^1$ is selected from the group consisting of H, alkyl, alkoxy, halo, hydroxyl, acyl, amino, alkylamino, disubstituted amino, sulfoxyl, sulfonyl, sulfonamide, alkoxylacylamino, and aminoacyloxy.

In some embodiments, $R^2$ is selected from the group consisting of H, alkyl, cycloalkyl, cycloalkylalkyl, cycloalkylalkenyl, heterocyclo, heterocycloalkyl, heterocycloalkenyl, aryl, arylalkyl, arylalkenyl, heteroaryl, heteroarylalkyl, heteroarylalkenyl, alkoxy, halo, azido, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy. Or more particularly, $R^2$ is selected from the group consisting of H, alkyl, alkoxy, halo, hydroxyl, amino, alkylamino, disubstituted amino, sulfoxyl, sulfonyl, sulfonamide, alkoxylacylamino, and aminoacyloxy.

In some embodiments, $R^3$ is selected from the group consisting of H, alkyl, cycloalkyl, cycloalkylalkyl, cycloalkylalkenyl, heterocyclo, heterocycloalkyl, heterocycloalkenyl, aryl, arylalkyl, arylalkenyl, heteroaryl, heteroarylalkyl, heteroarylalkenyl, heteroarylalkynyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy. Or more particularly, $R^3$ is selected from the group consisting of H, alkyl, alkenyl, alkynyl, alkoxy, halo, cyano, hydroxyl, alkylthio, amino, alkylamino, disubstituted aminosulfoxyl, sulfonyl, sulfonamide, alkoxylacylamino, and aminoacyloxy.

In some embodiments, $R^4$ is selected from the group consisting of H, alkyl, alkenyl, cycloalkyl, cycloalkylalkyl, cycloalkylalkenyl, heterocyclo, heterocycloalkyl, heterocycloalkenyl, aryl, arylalkyl, arylalkenyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy. Or more particularly, $R^4$ is selected from the group consisting of H, alkyl, alkoxy, halo, cyano, hydroxyl, alkylthio, amino, alkylamino, disubstituted amino, sulfoxyl, and sulfonyl.

In some embodiments, $R^5$ is selected from the group consisting of H, alkyl, alkenyl, cycloalkyl, cycloalkylalkyl, cycloalkylalkenyl, heterocyclo, heterocycloalkyl, heterocycloalkenyl, heterocycloalkynyl, aryl, arylalkyl, arylalkenyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy. Or more particularly, $R^5$ is selected from the group consisting of H, alkyl, alkoxy, halo, cyano, hydroxyl, alkylthio, amino, alkylamino, disubstituted amino, sulfoxyl, and sulfonyl.

In some embodiments, each $R^6$ is independently selected from the group consisting of H, alkyl, alkenyl, alkynyl, cycloalkyl, cycloalkylalkyl, cycloalkylalkenyl, heterocyclo, heterocycloalkyl, heterocycloalkenyl, aryl, arylalkyl, arylalkenyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy. Or more particularly, each $R^6$ is independently selected from the group consisting of H, alkyl halo, and hydroxyl.

In some embodiments, each $R^7$ is independently selected from the group consisting of H, alkyl, alkenyl, cycloalkyl, cycloalkylalkyl, cycloalkylalkenyl heterocyclo, heterocycloalkyl, heterocycloalkenyl, aryl, arylalkyl, arylalkenyl, arylalkynyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy. Or more particularly, each $R^7$ is independently selected from the group consisting of H, alkyl, alkoxy, halo, cyano, hydroxyl, amino, alkylamino, disubstituted amino sulfoxyl, and sulfonyl.

In some embodiments, each $R^8$ is independently selected from the group consisting of H, alkyl, alkenyl, cycloalkyl, cycloalkylalkyl, cycloalkylalkenyl, heterocyclo, heterocycloalkyl, heterocycloalkenyl, aryl, arylalkyl, arylalkenyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy. Or more particularly, each $R^8$ is independently selected from the group consisting of H, alkyl, halo, and hydroxyl.

Examples of compounds of the present invention include, but are not limited to, those set forth in Schemes A to C, and 1 to 15, as follows:

Scheme A
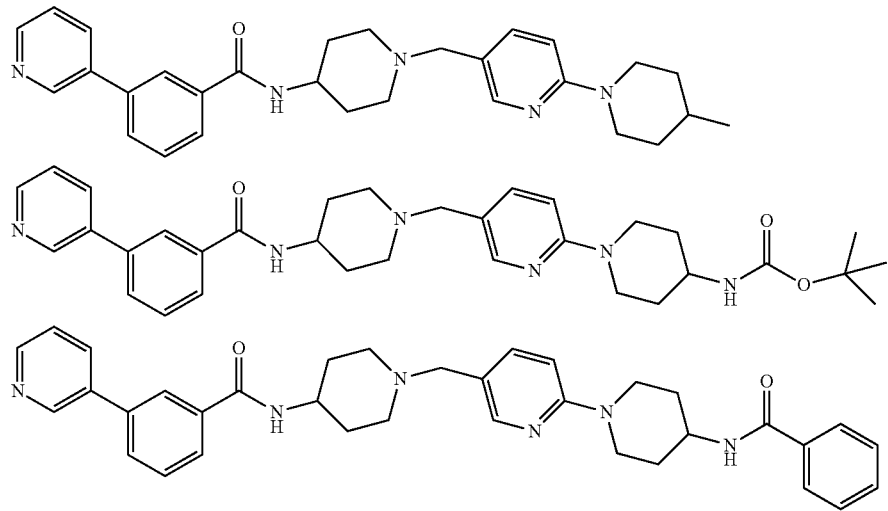
Scheme B
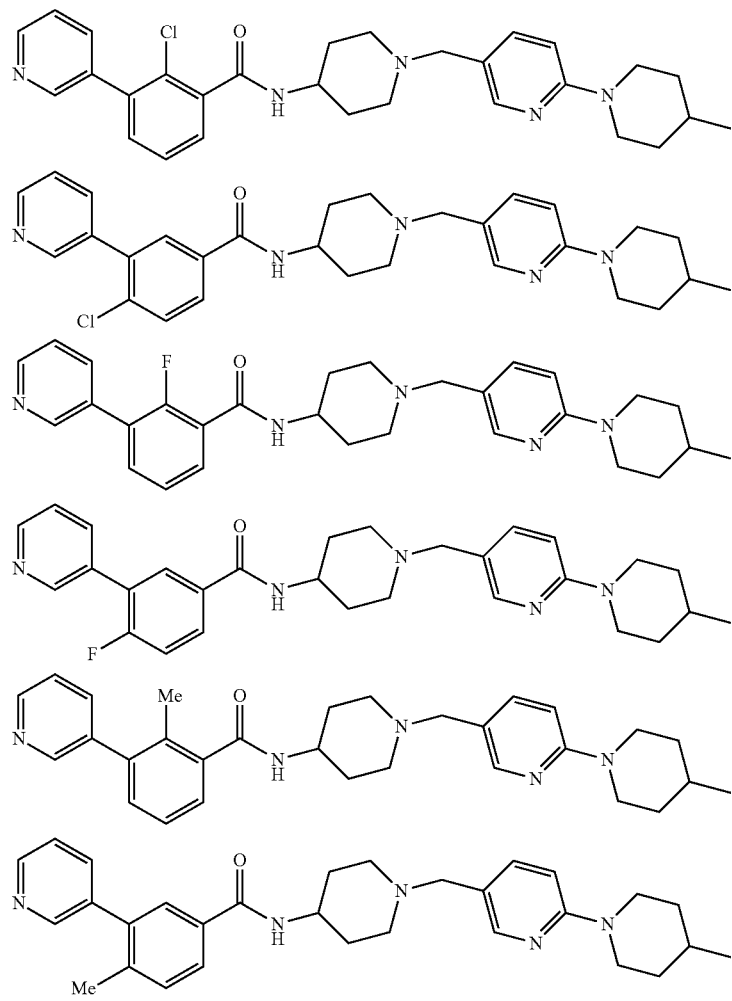

-continued
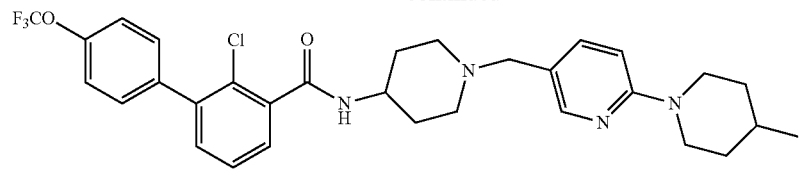
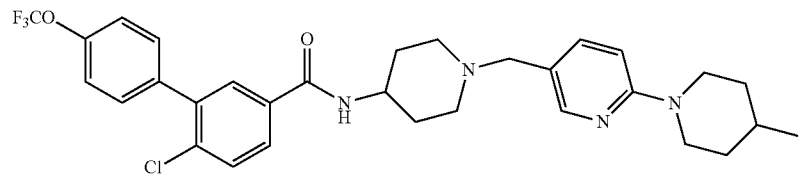
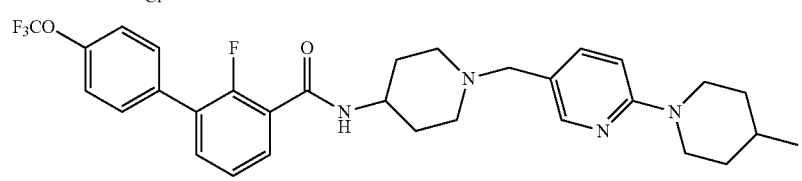
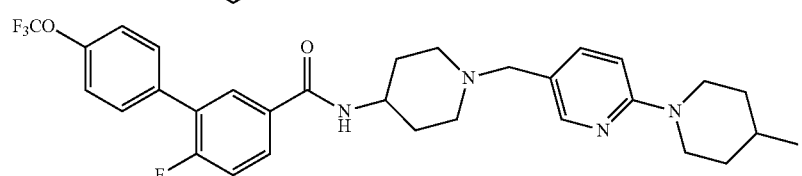
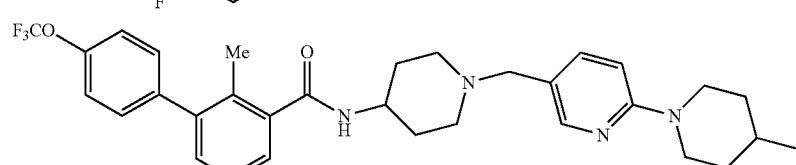
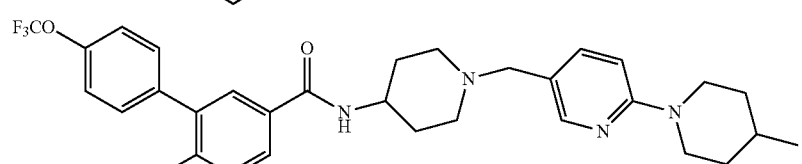
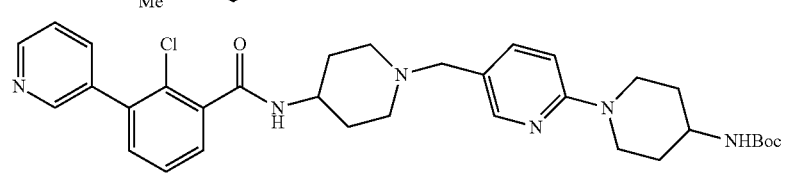
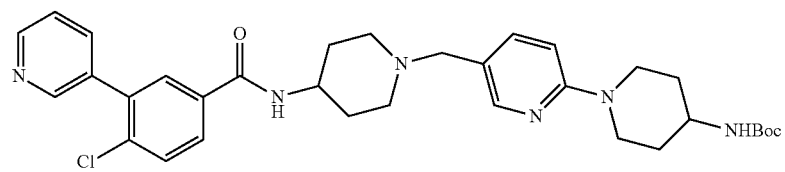
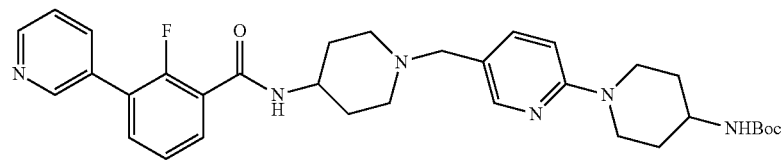
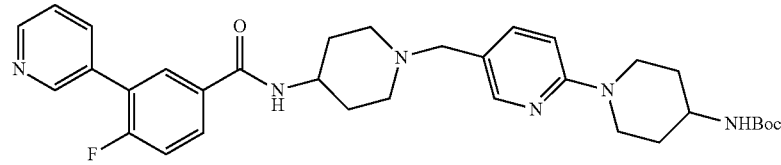

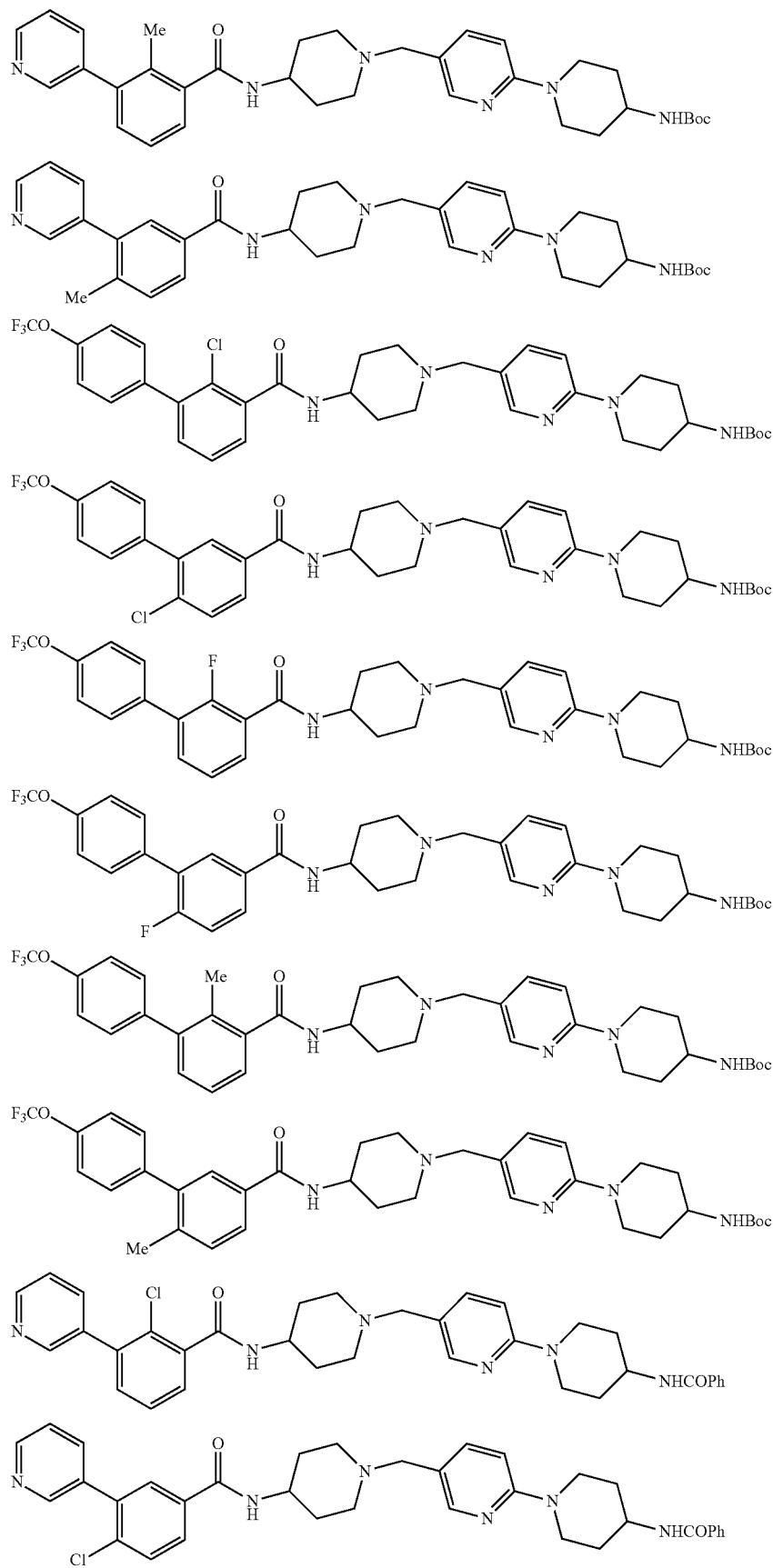

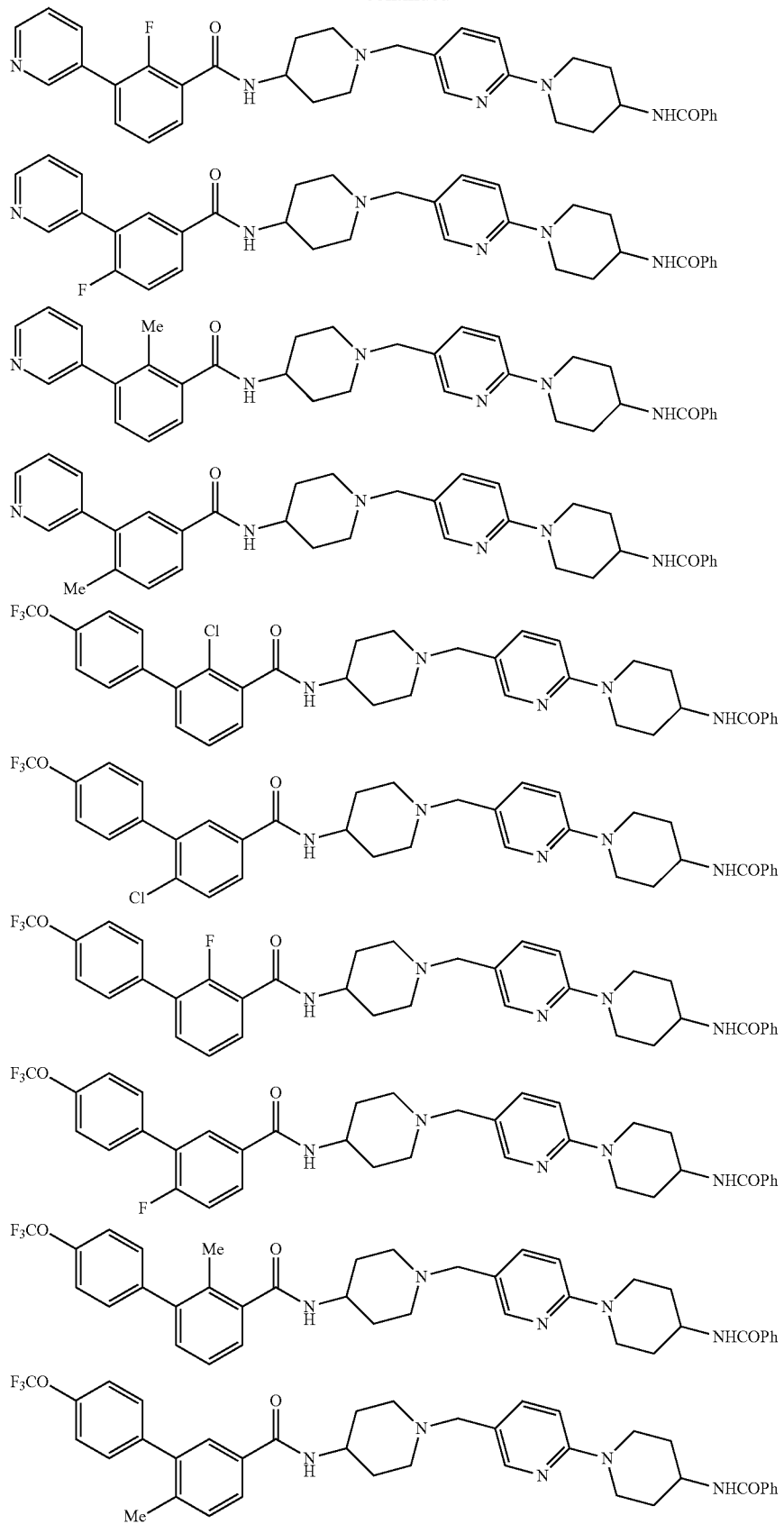

Scheme C
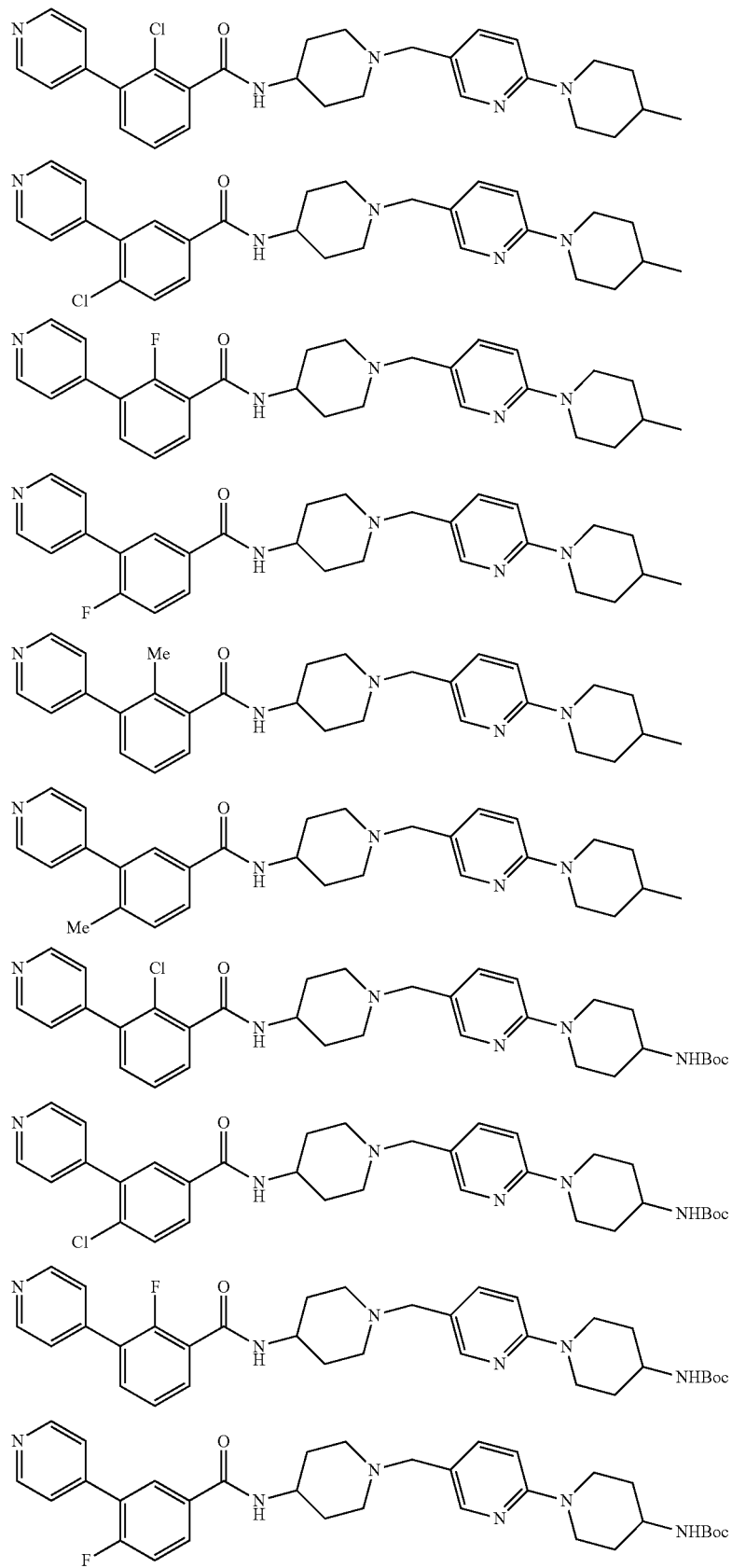

-continued
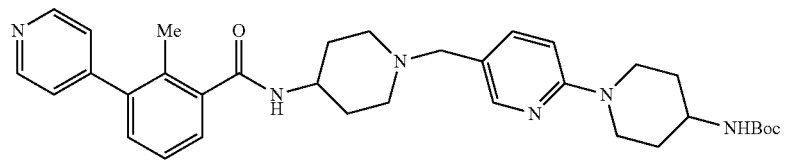
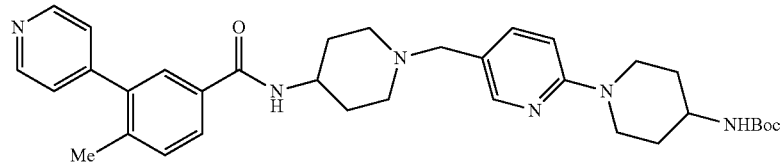
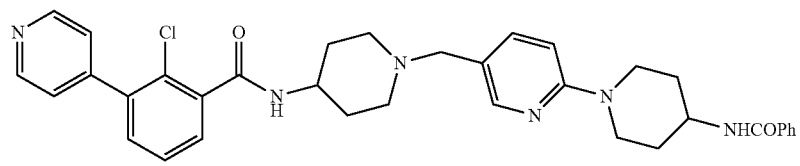
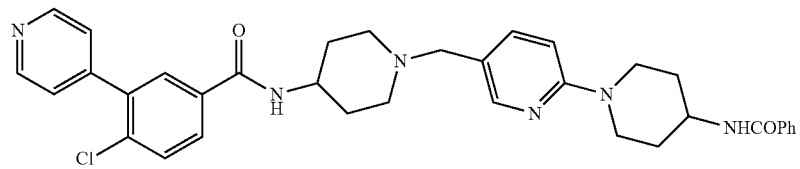
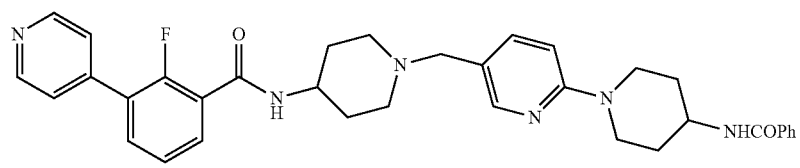
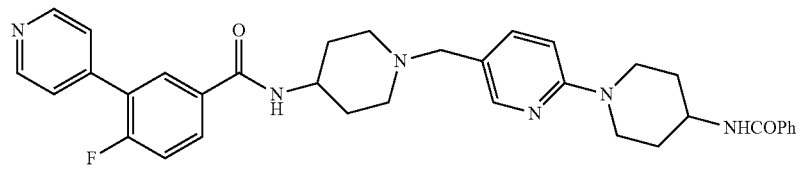
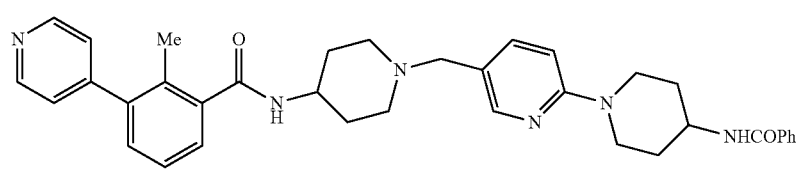
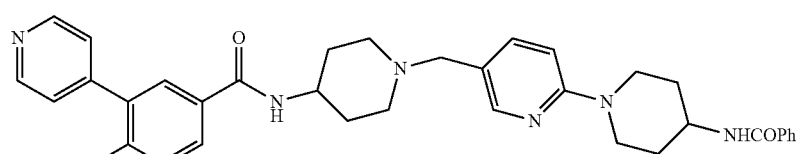
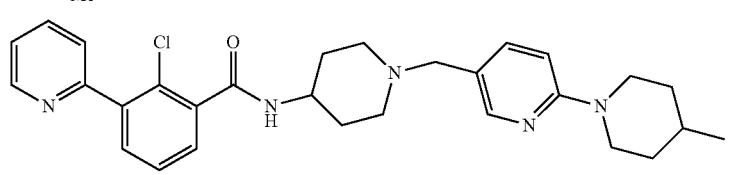
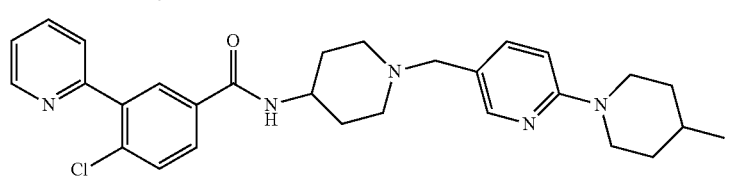

-continued
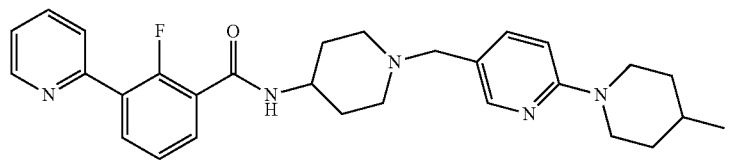
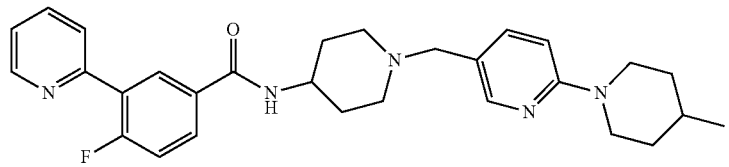
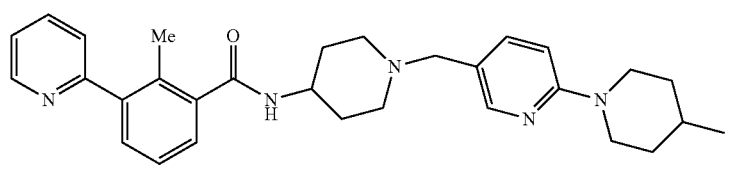
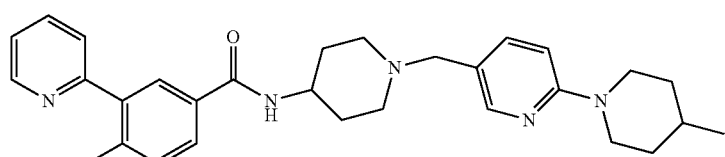
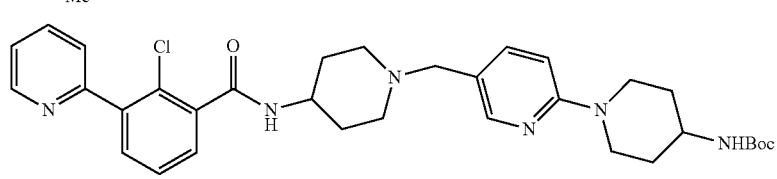
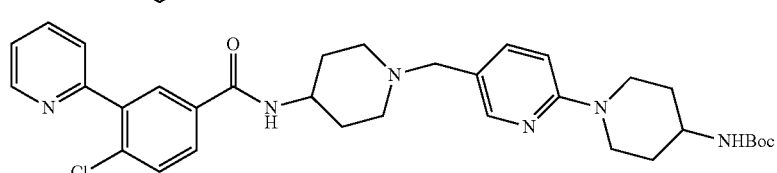
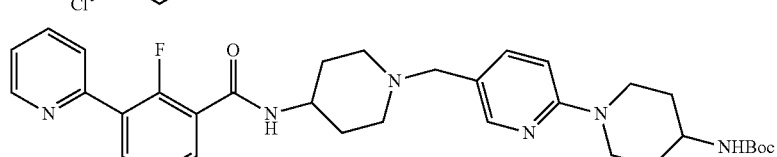
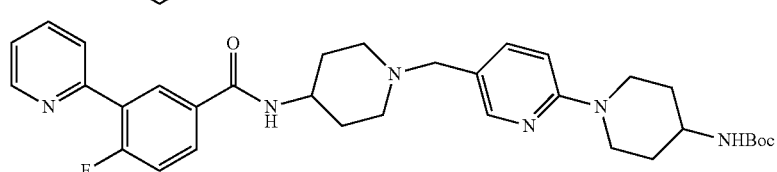
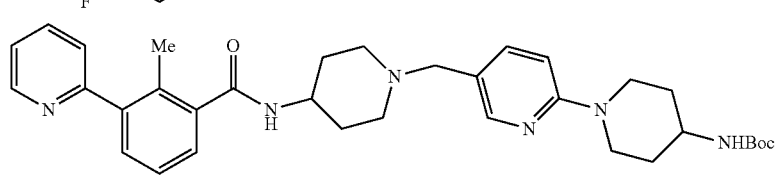
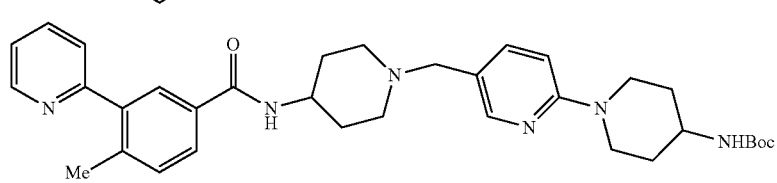

-continued
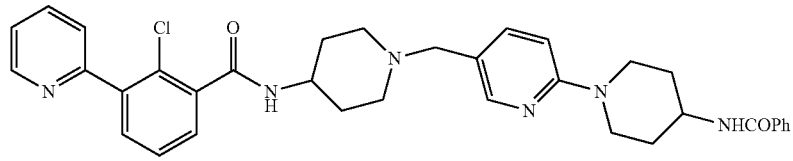
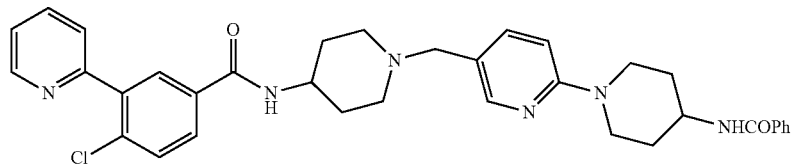
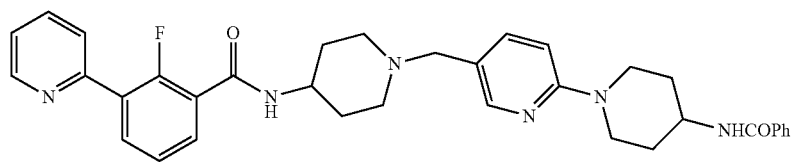
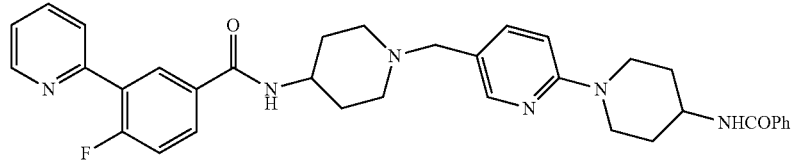
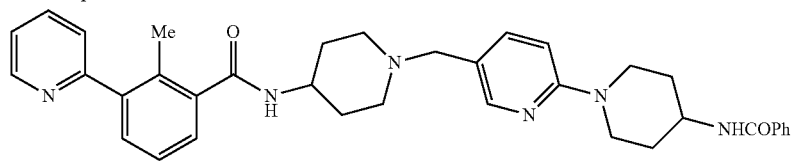
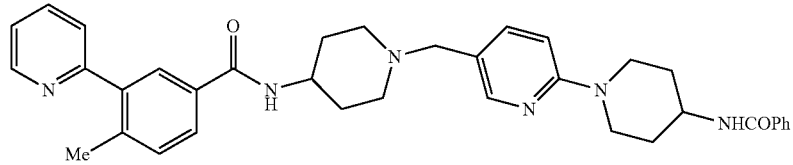
Scheme 1
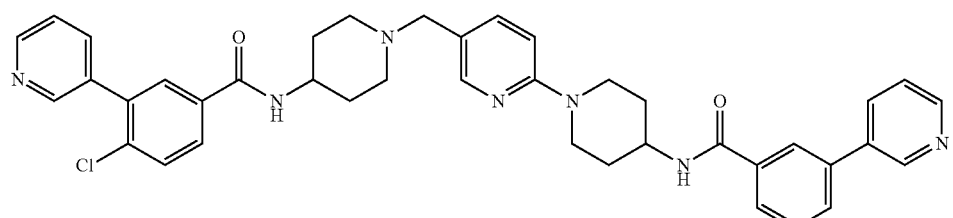
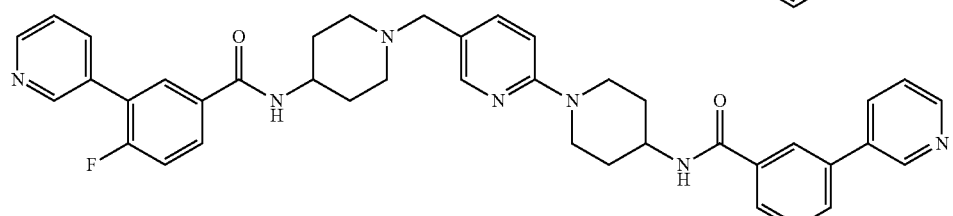
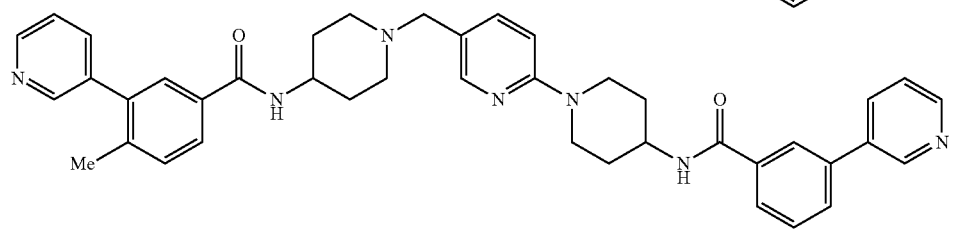

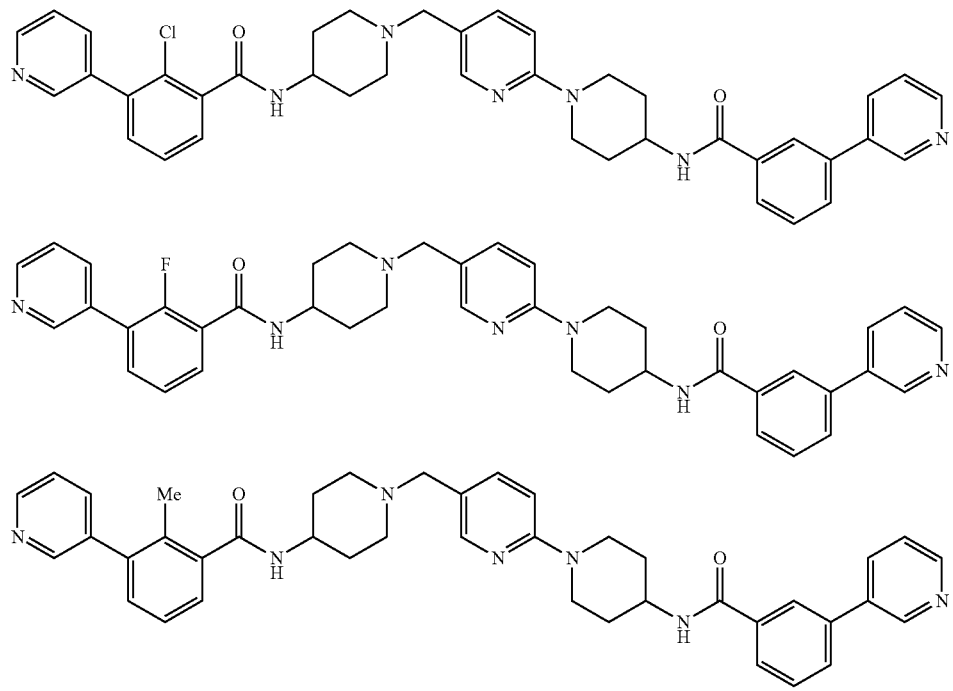
Scheme 2
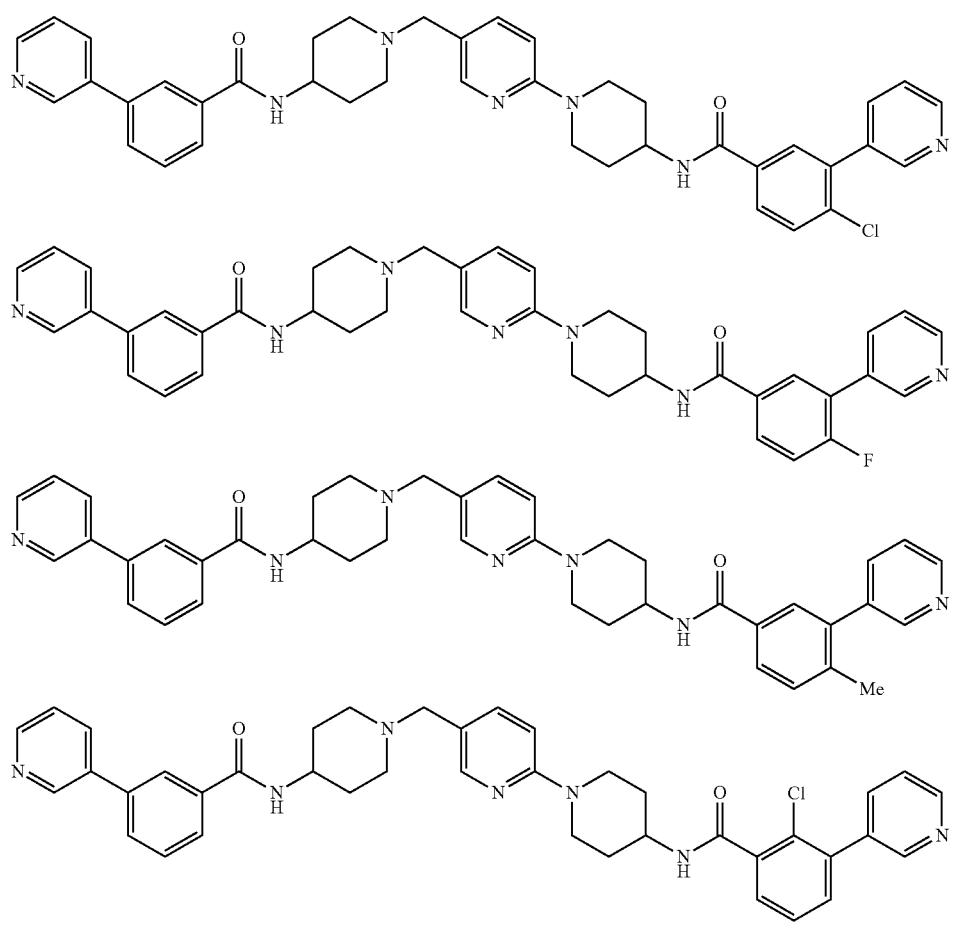

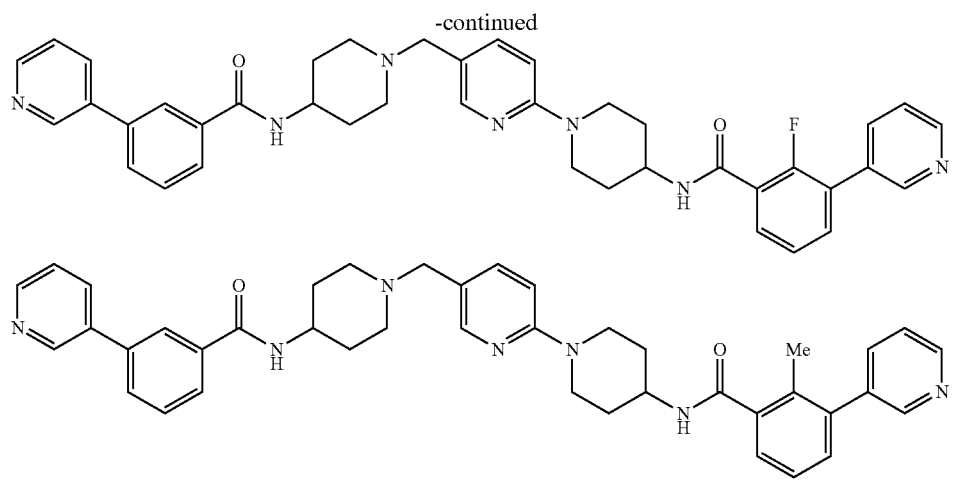
Scheme 3
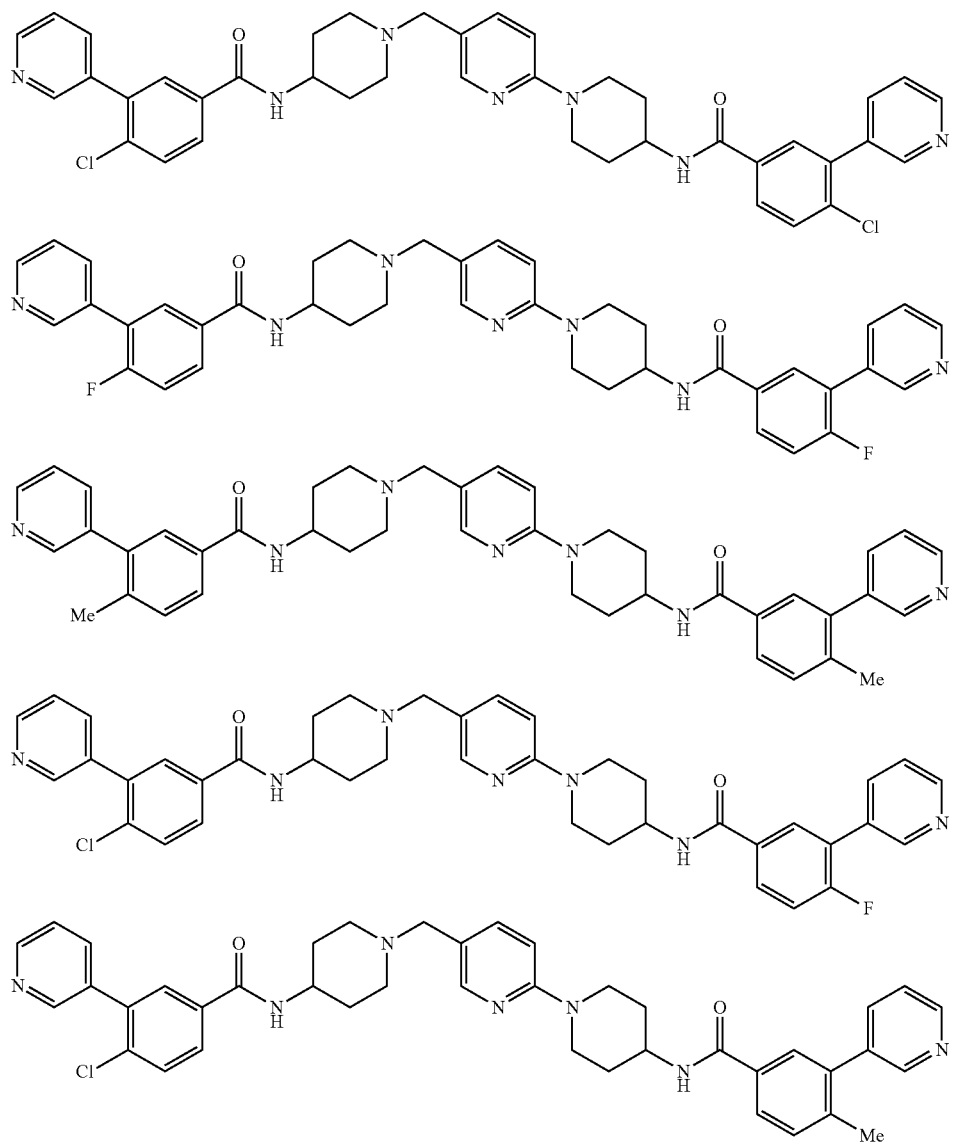

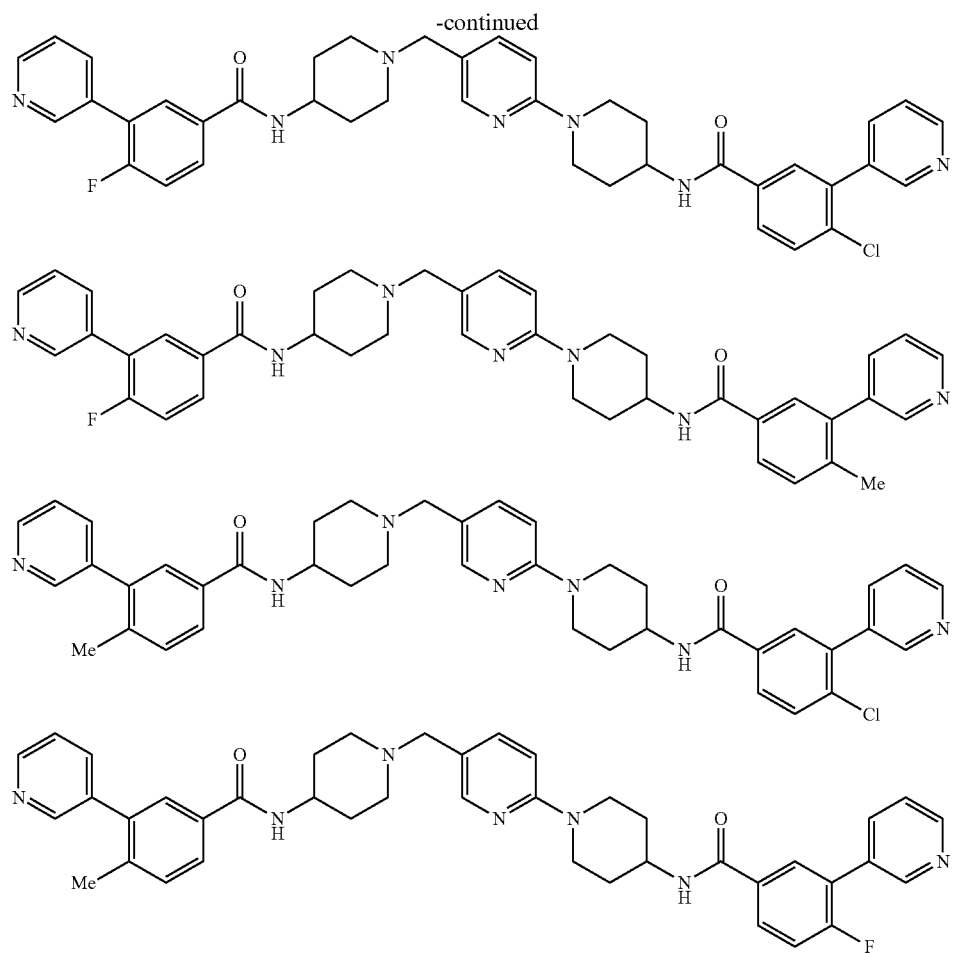
Scheme 4
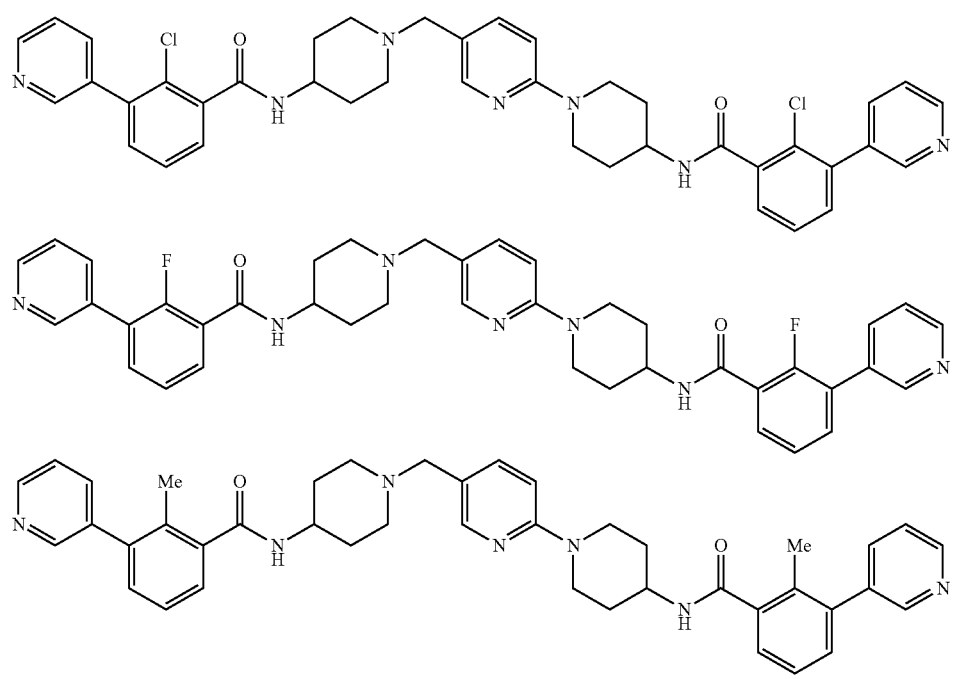

-continued
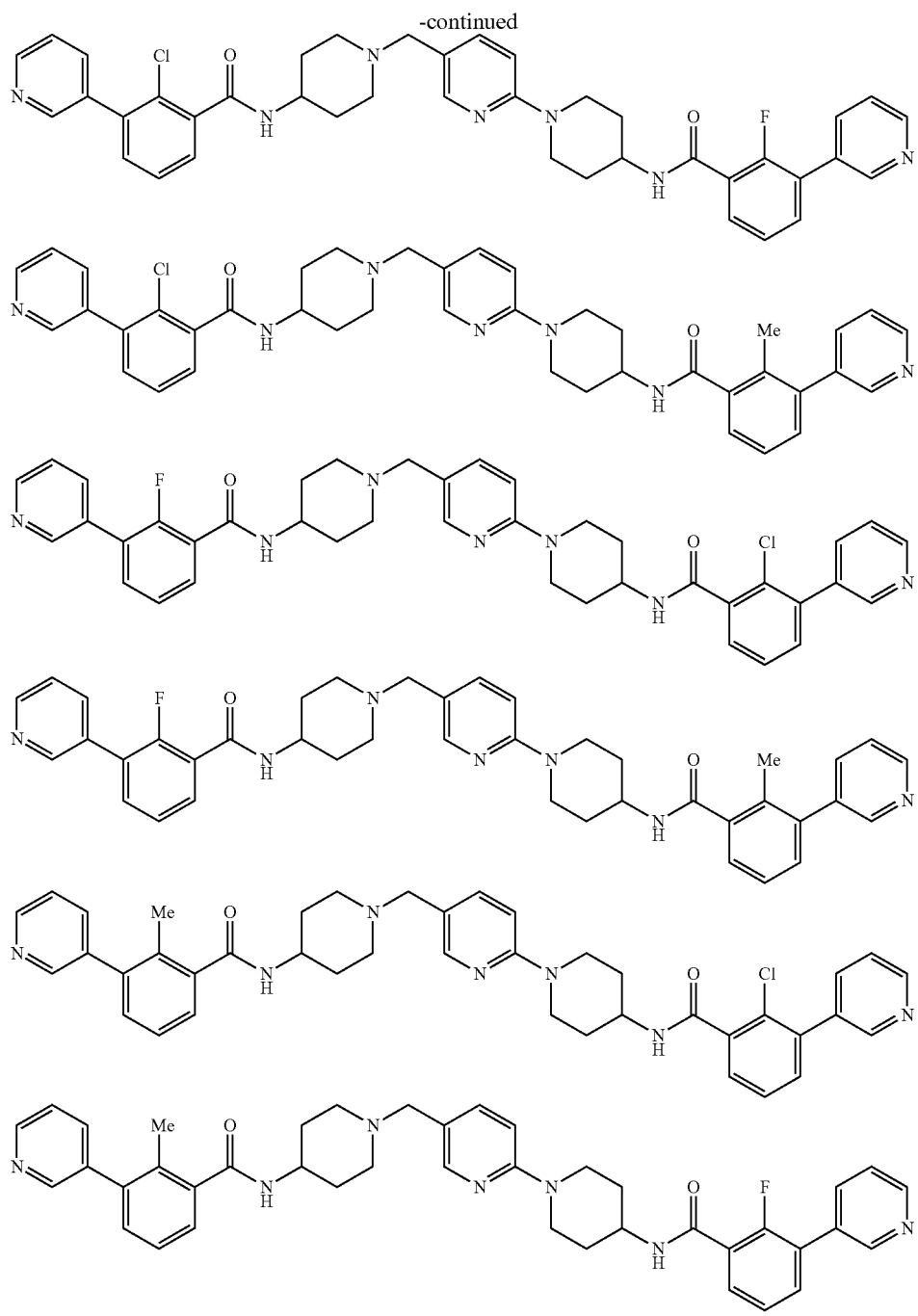
Scheme 5
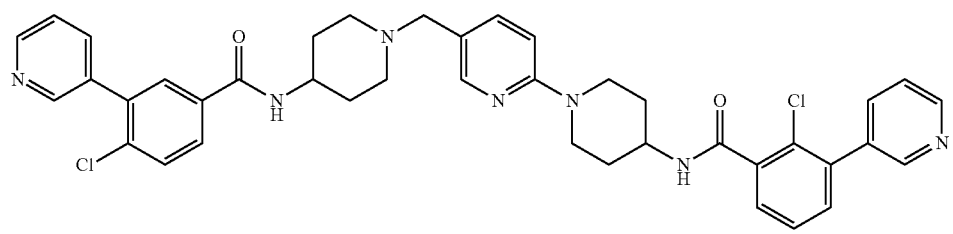

-continued
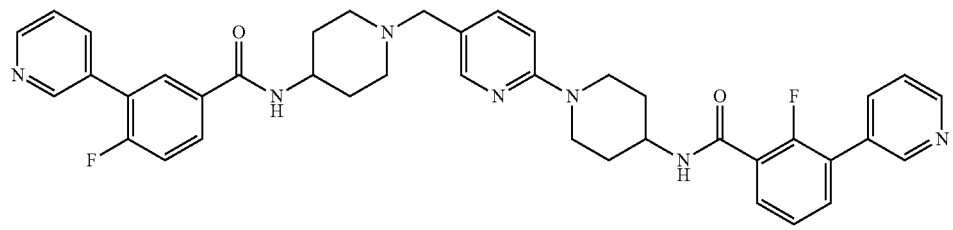
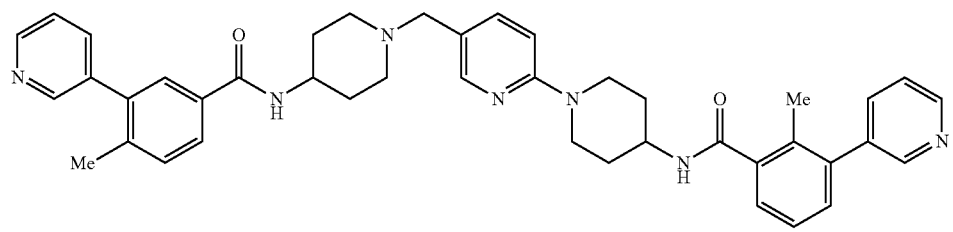
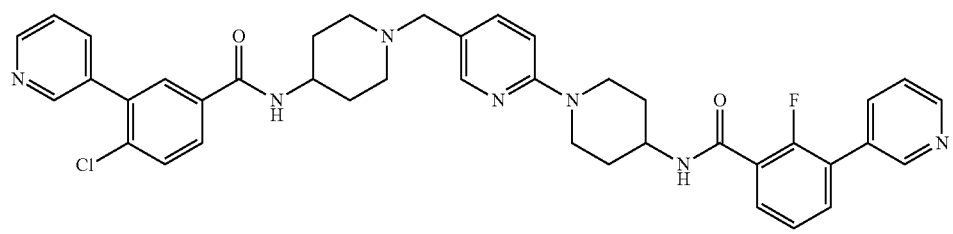
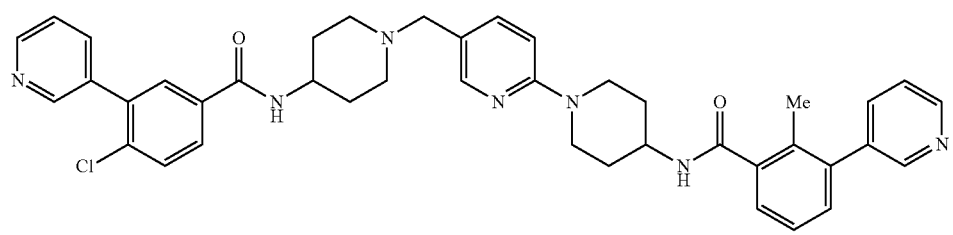
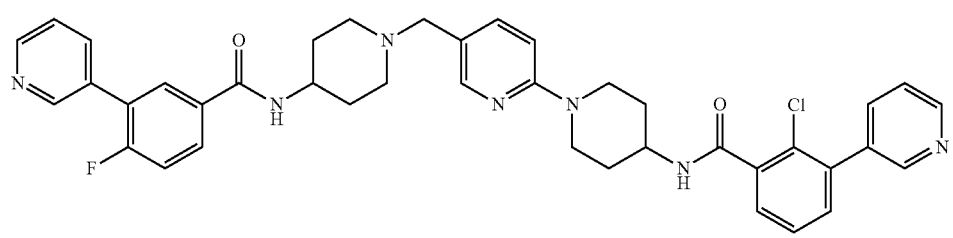
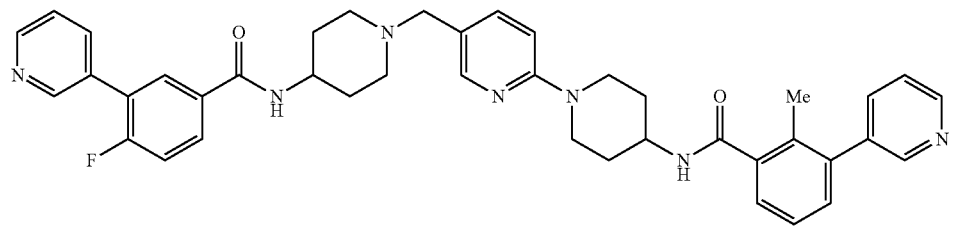
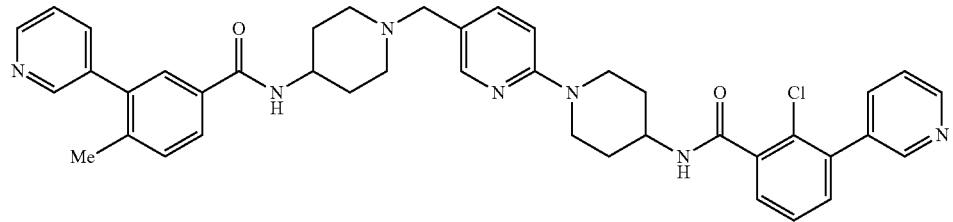

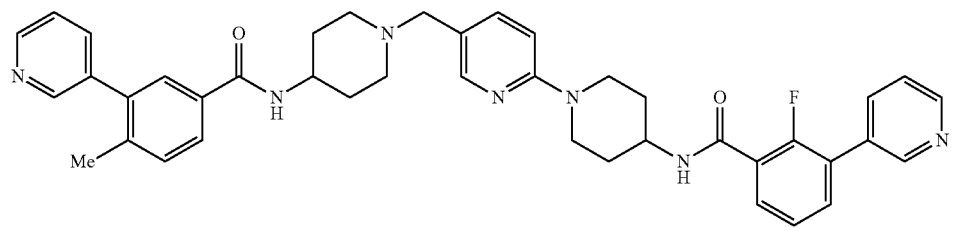
Scheme 6
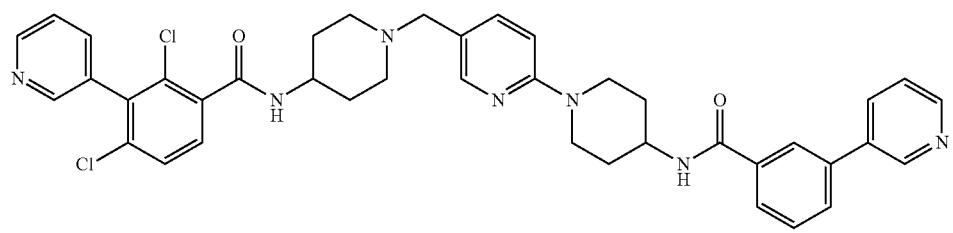
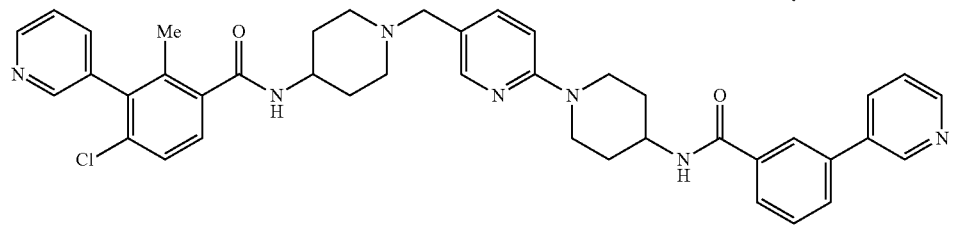
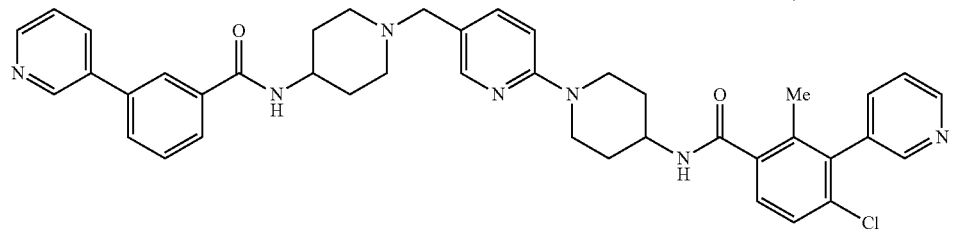
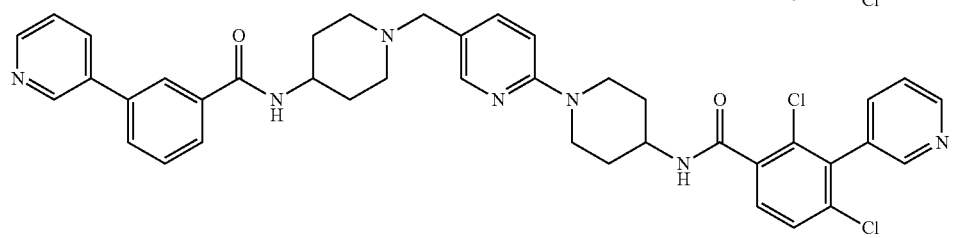
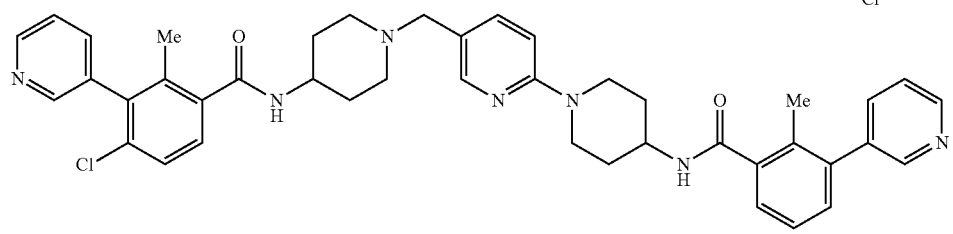
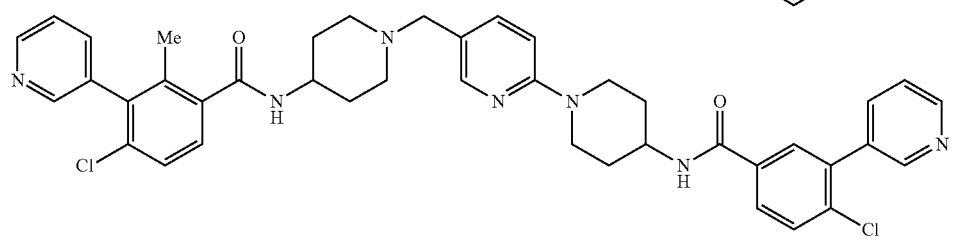

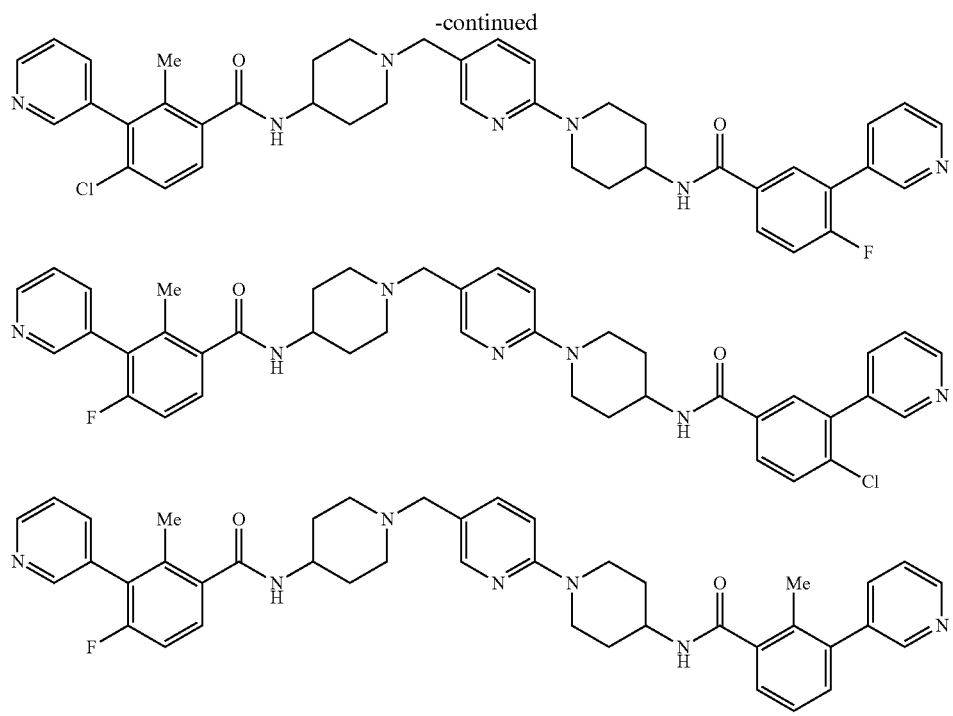
Scheme 7
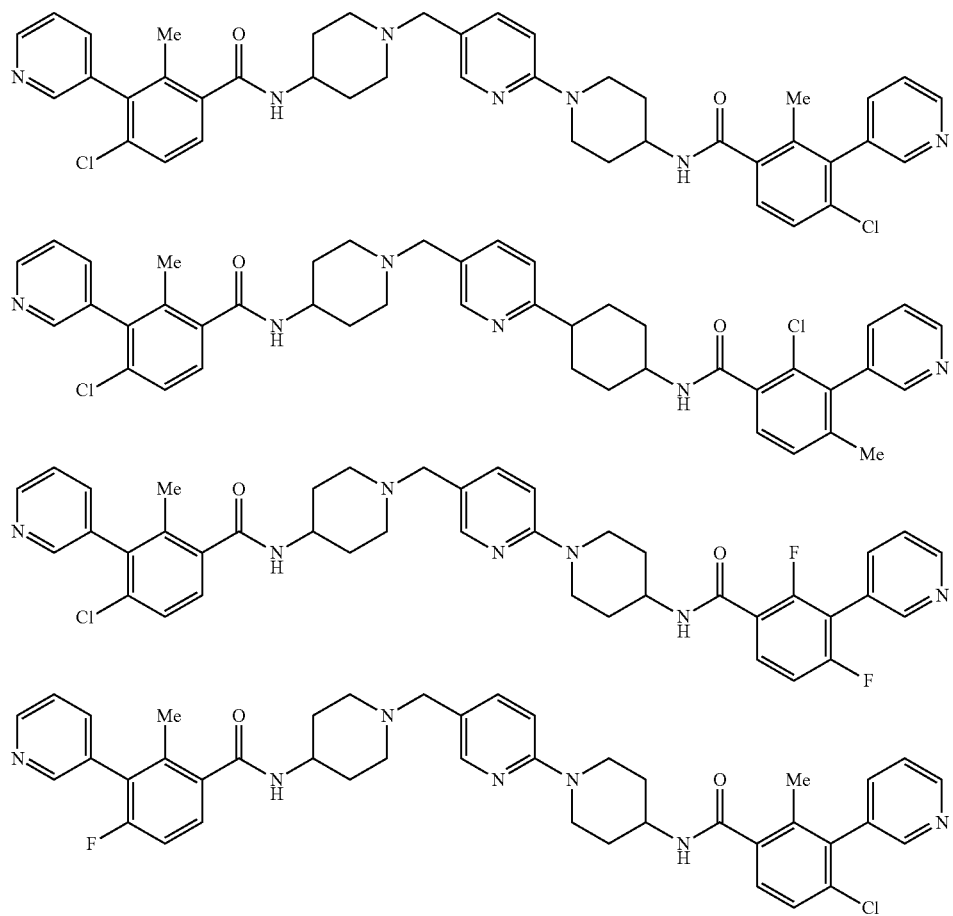

-continued
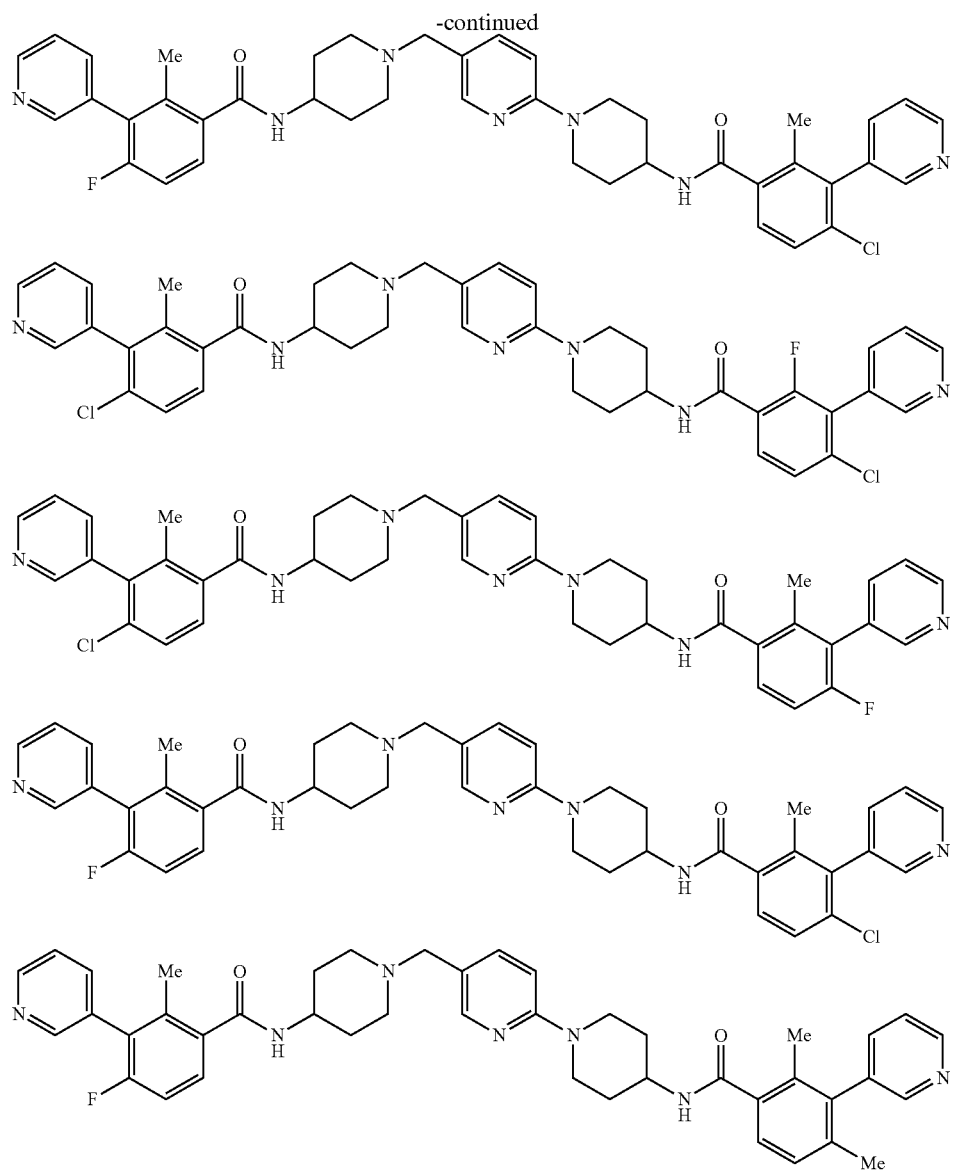
Scheme 8
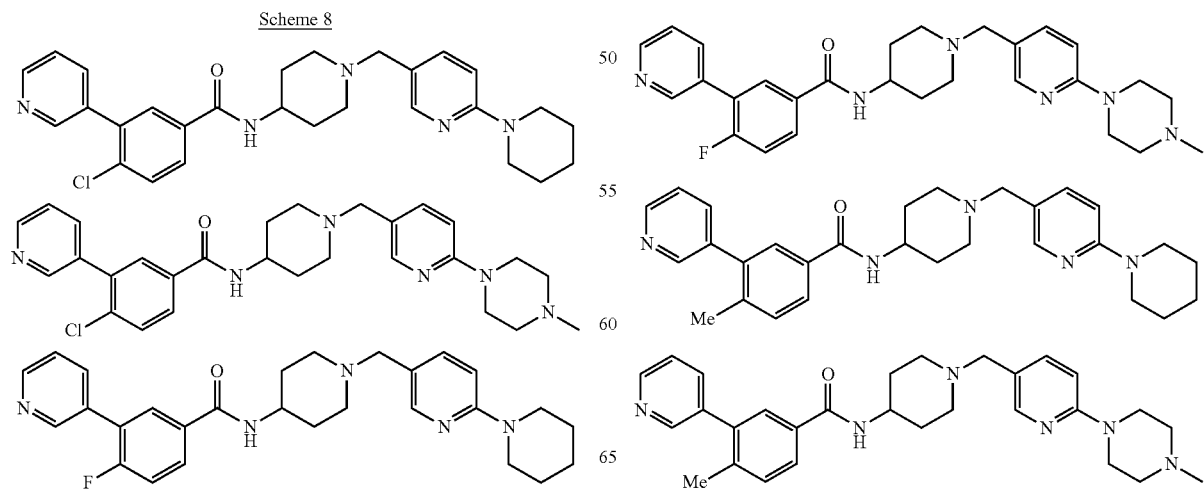

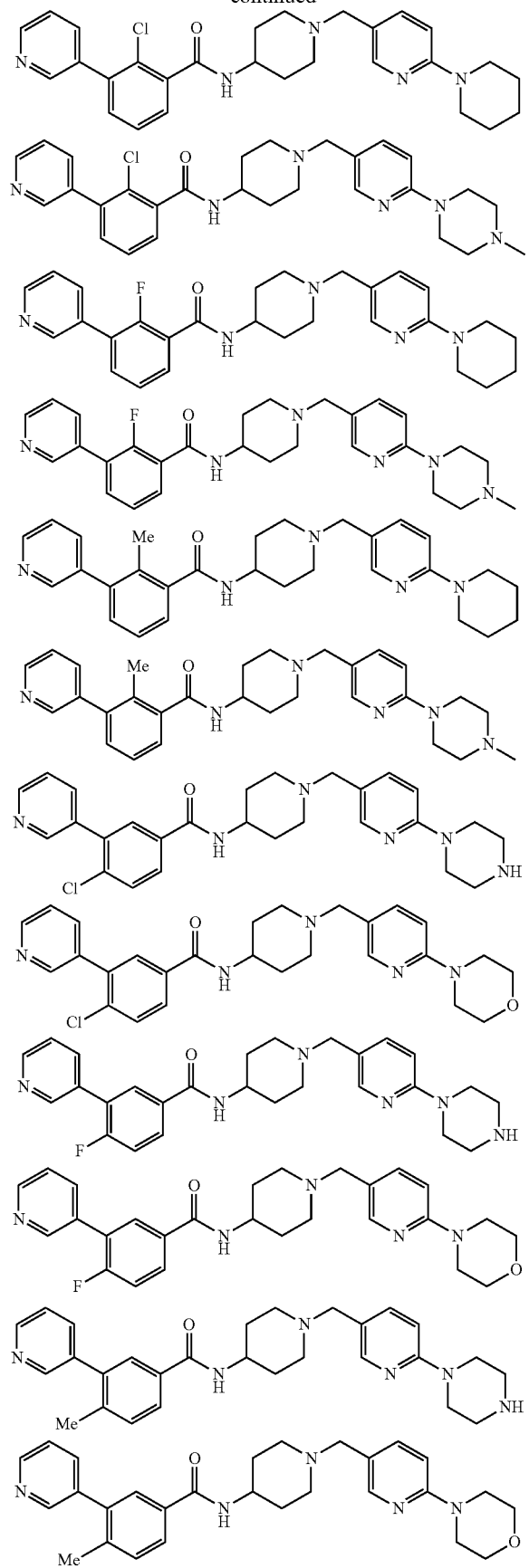
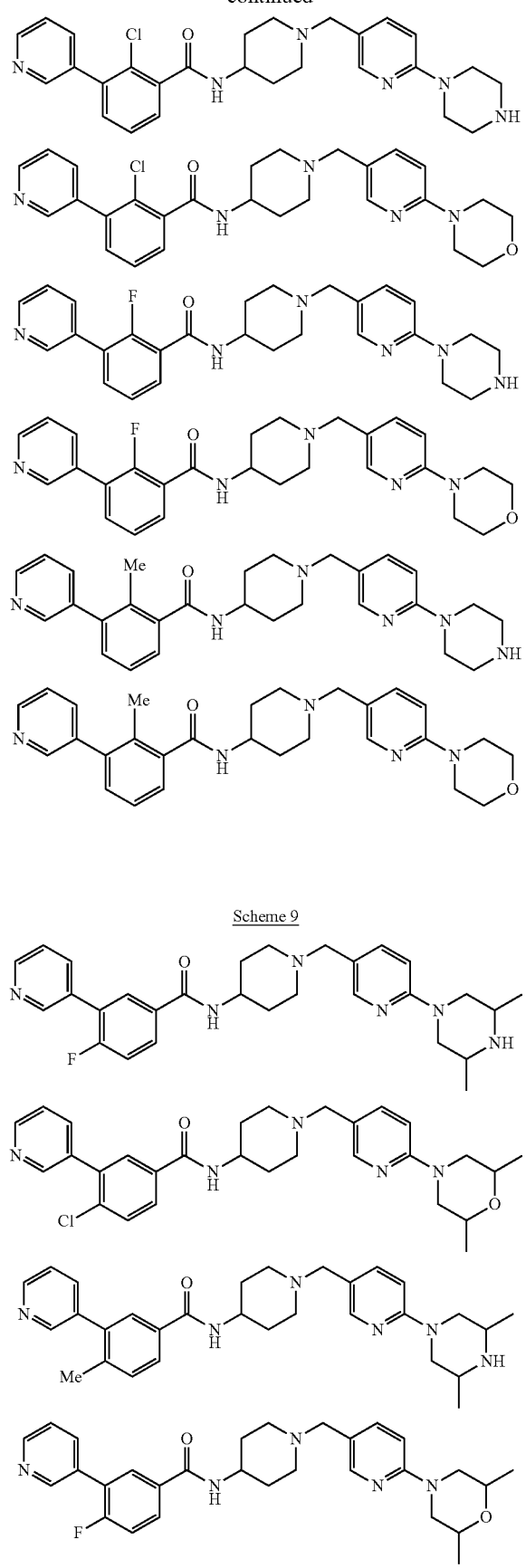
Scheme 9

47
-continued
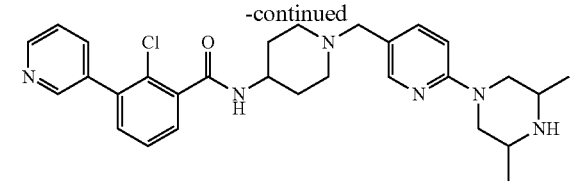
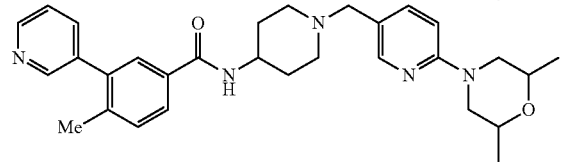
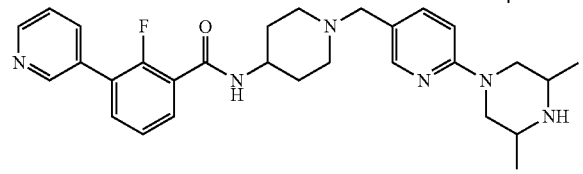
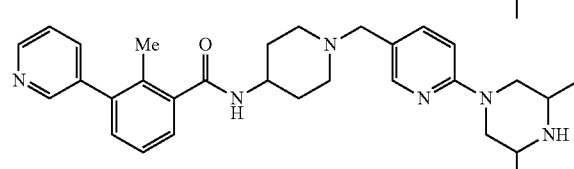
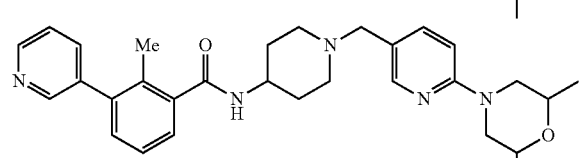
Scheme 10
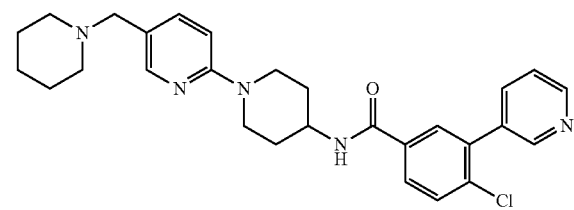
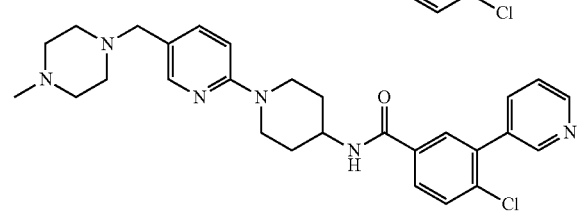
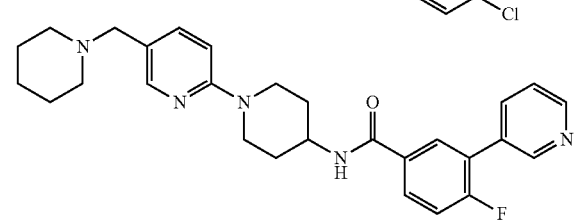
48
-continued
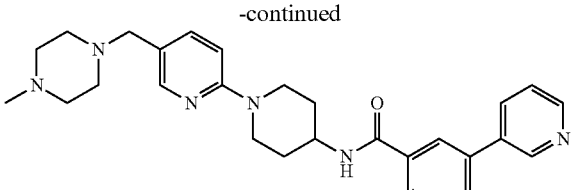
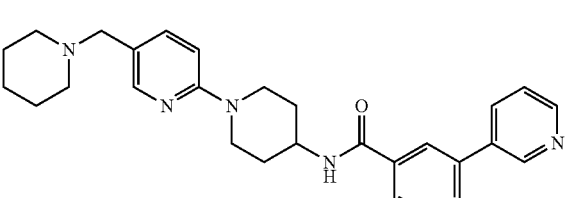
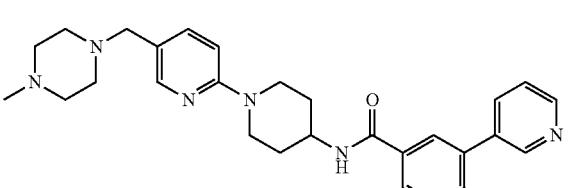
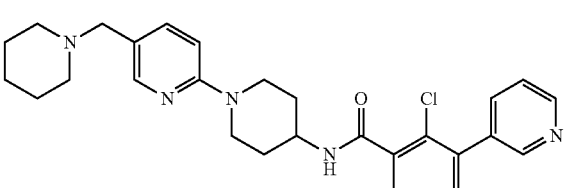
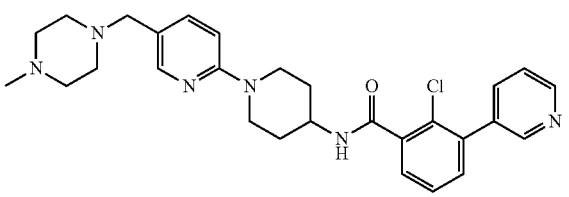

49
-continued
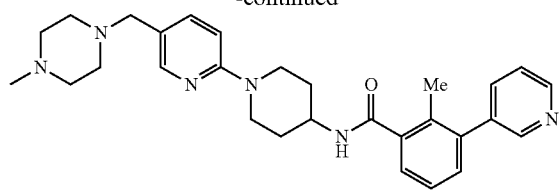
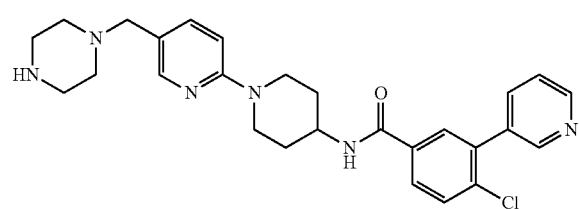
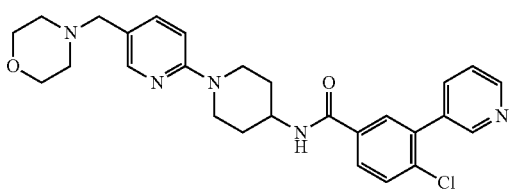
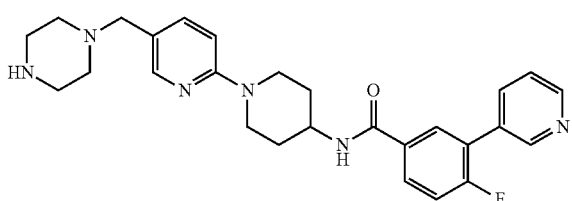
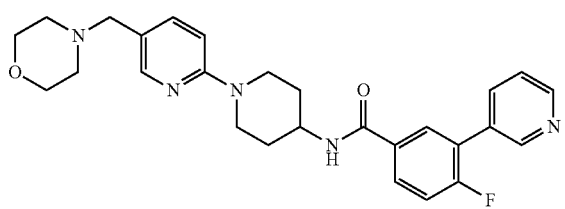
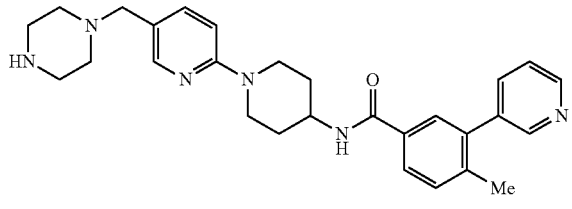
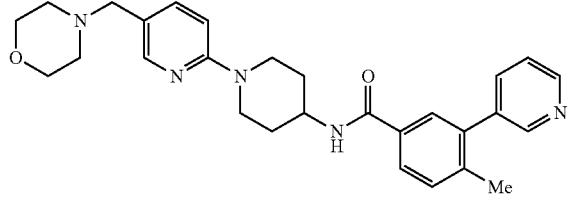
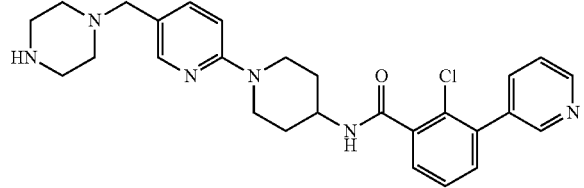
50
-continued
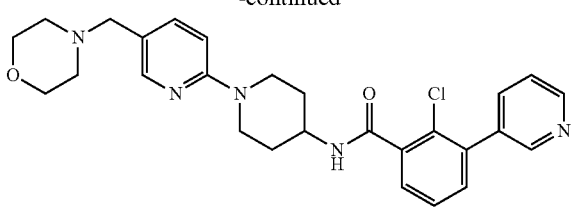
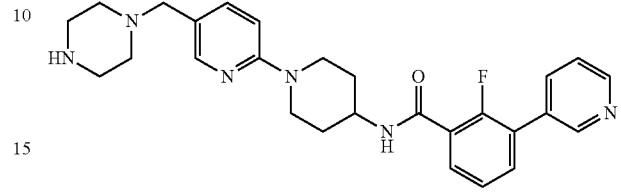
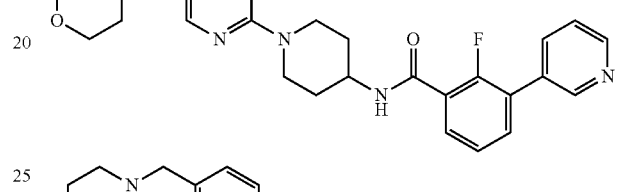
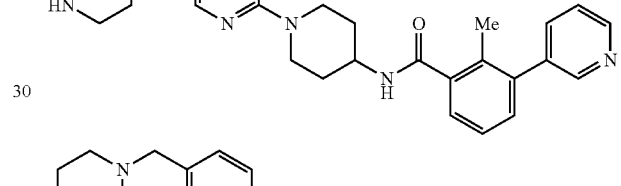
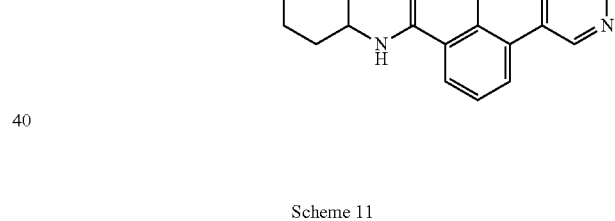
Scheme 11
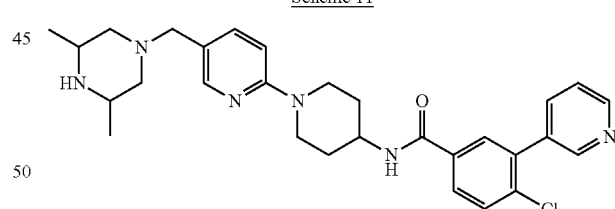
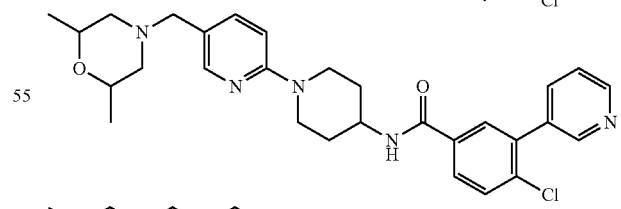

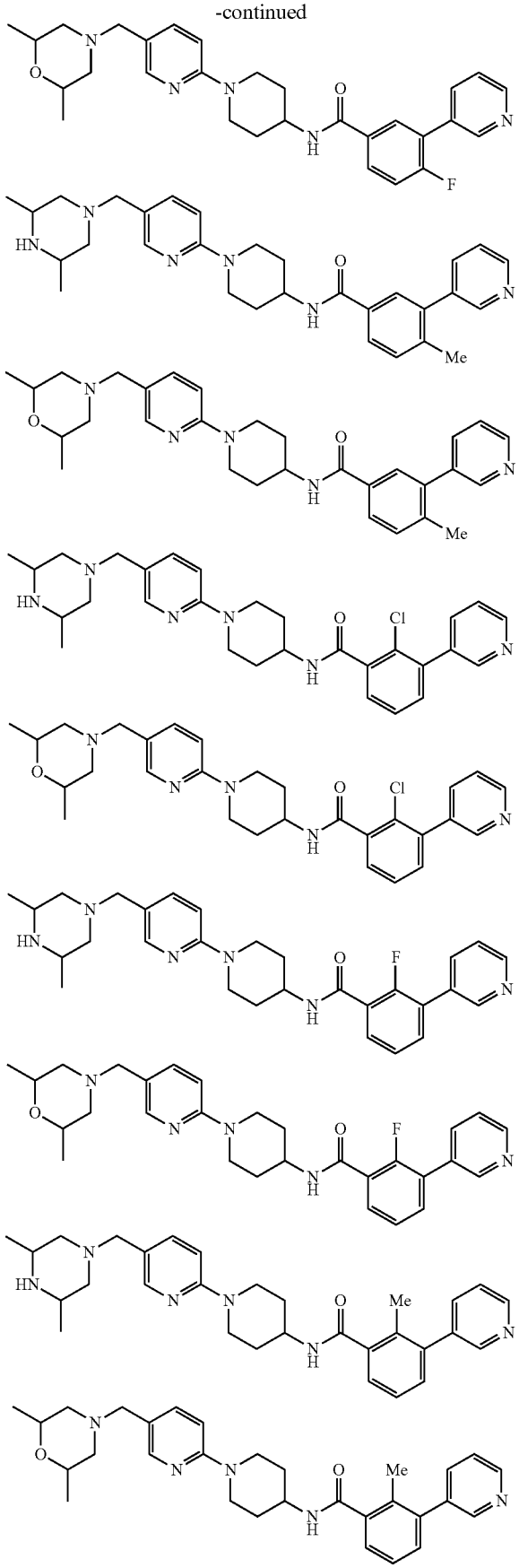
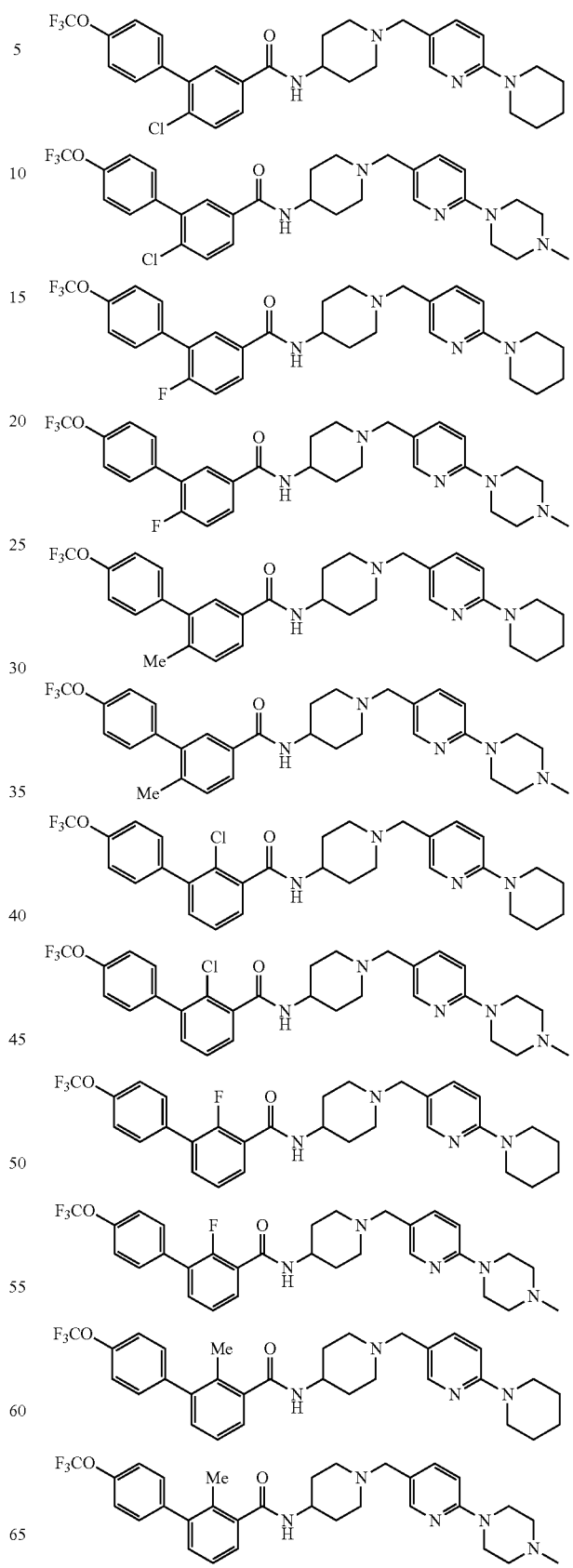
Scheme 12

-continued
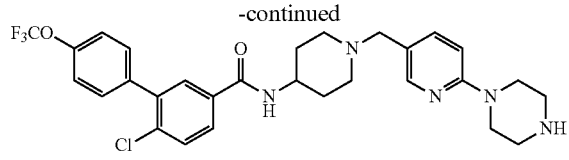
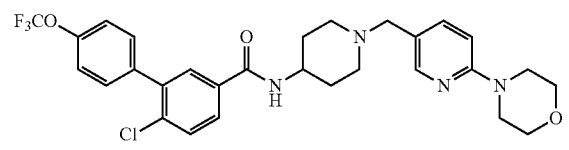
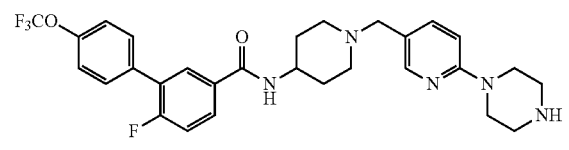
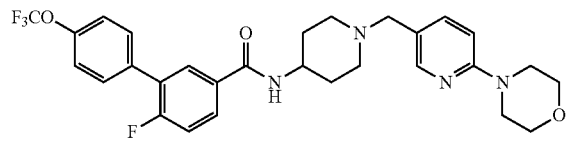
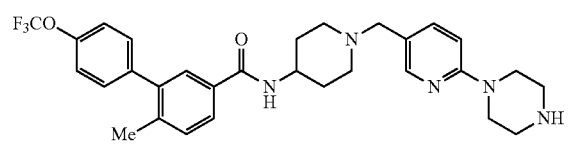
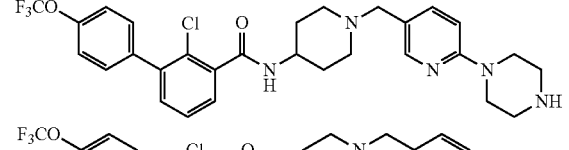
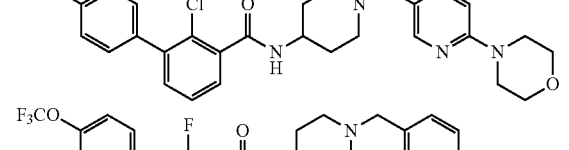
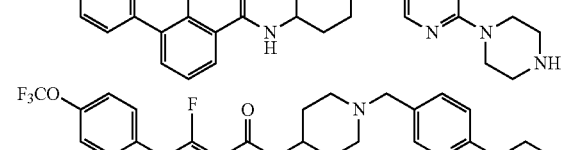
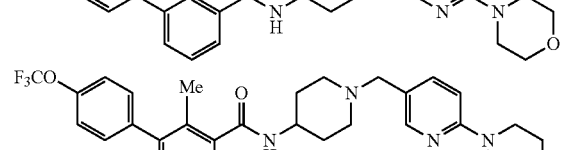
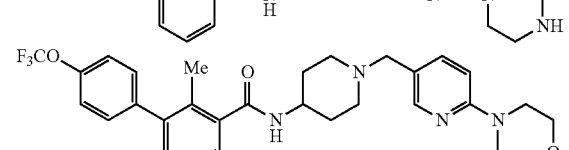
Scheme 13
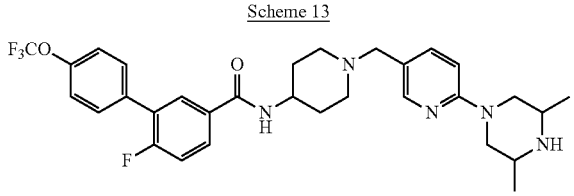
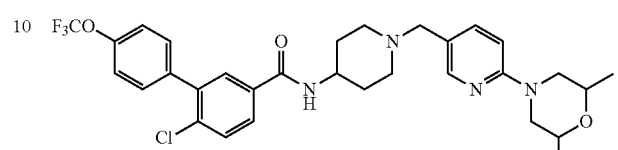
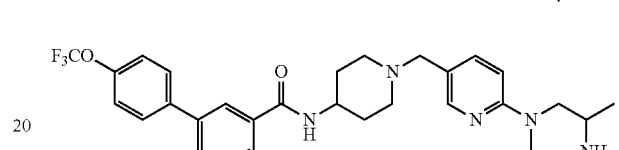
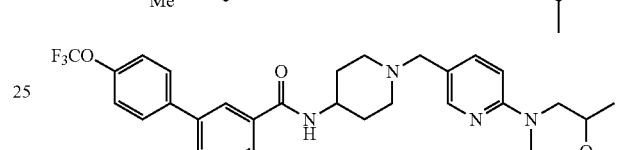
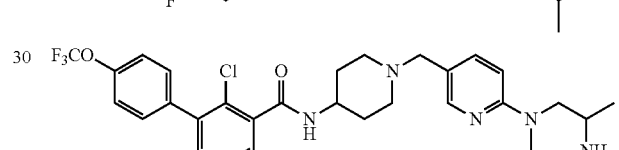
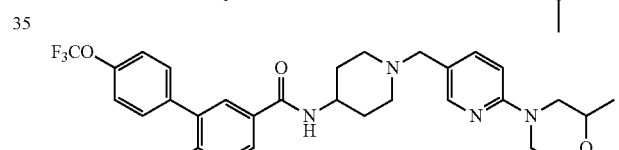
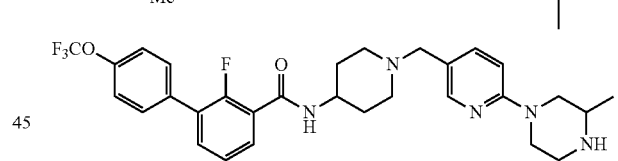
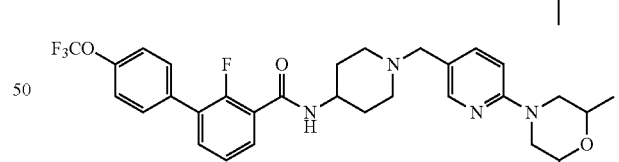
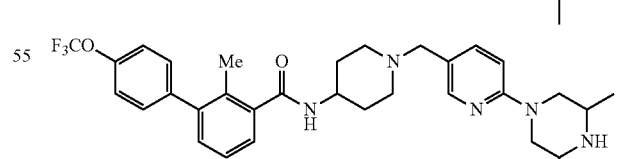
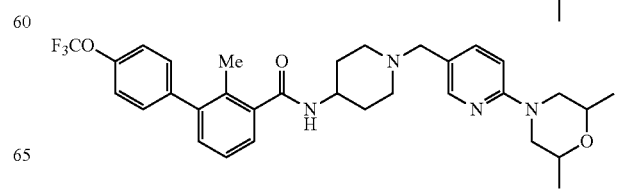

Scheme 14
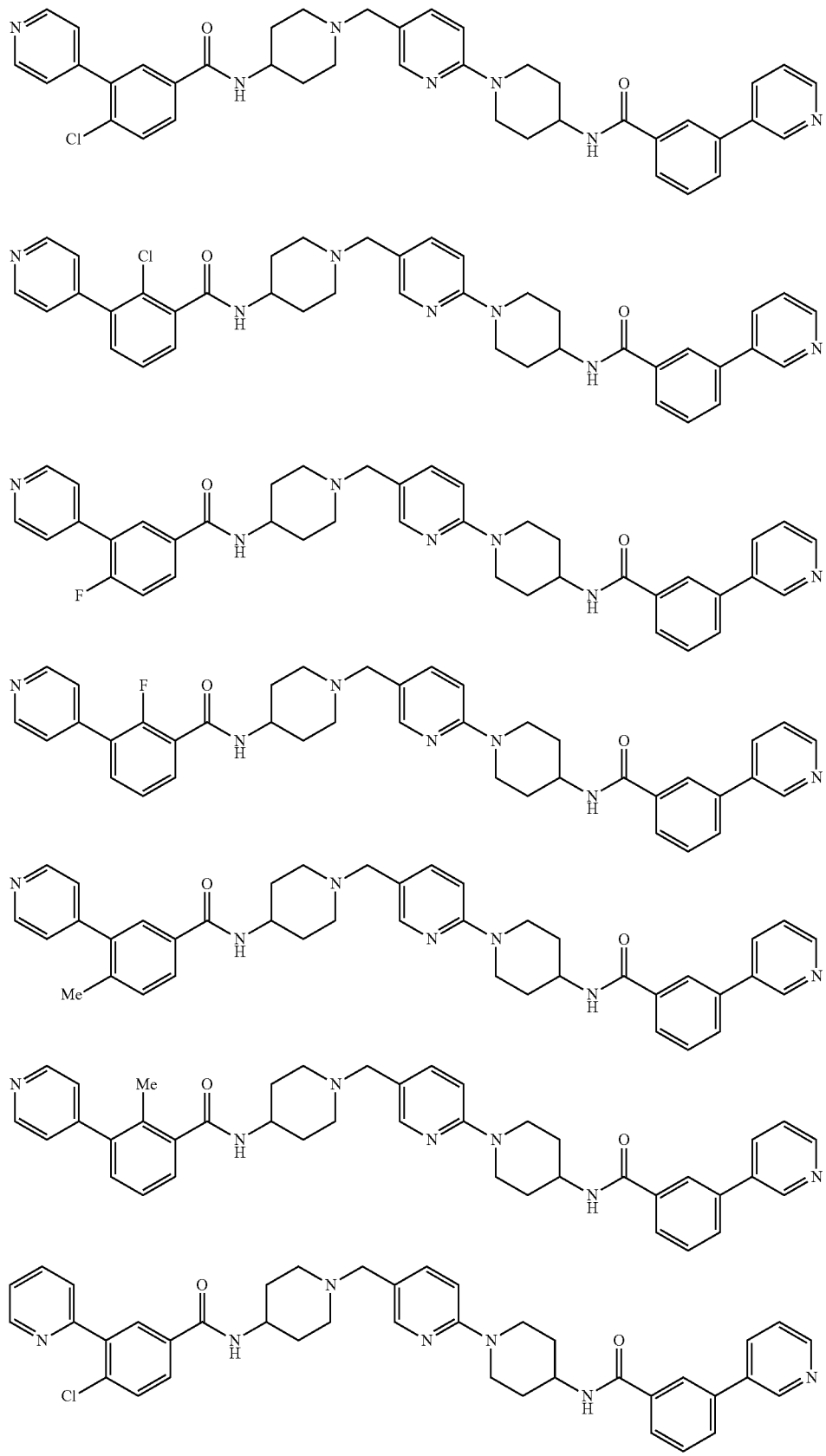

-continued
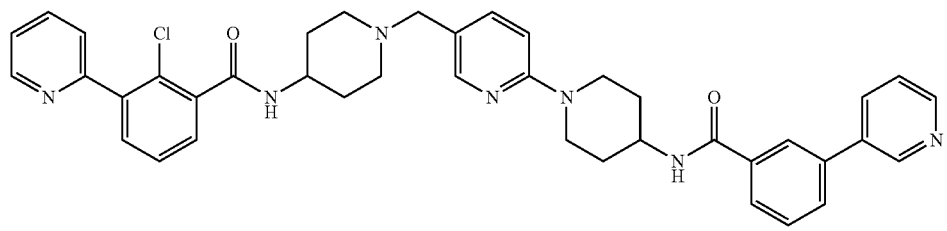
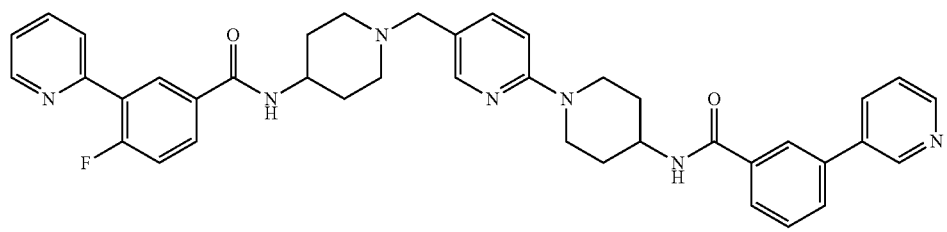
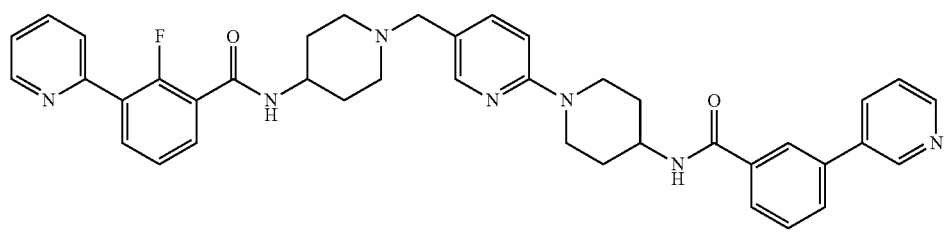
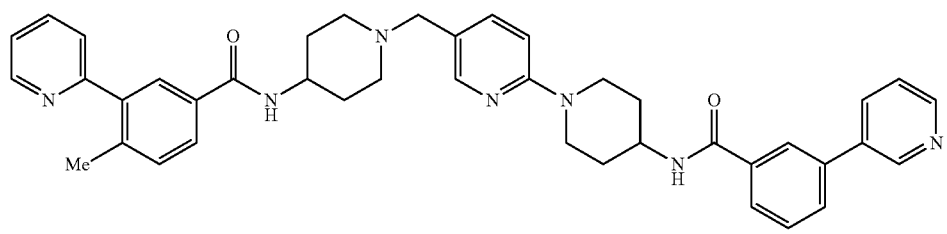
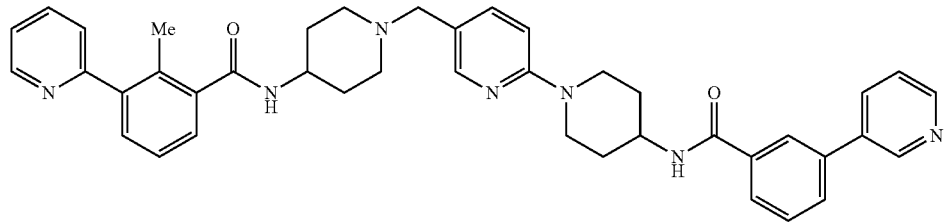
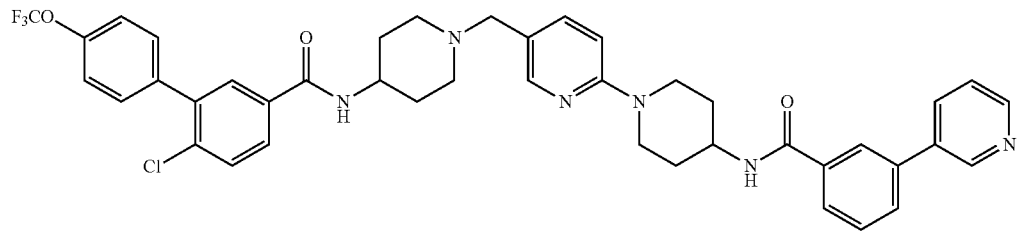
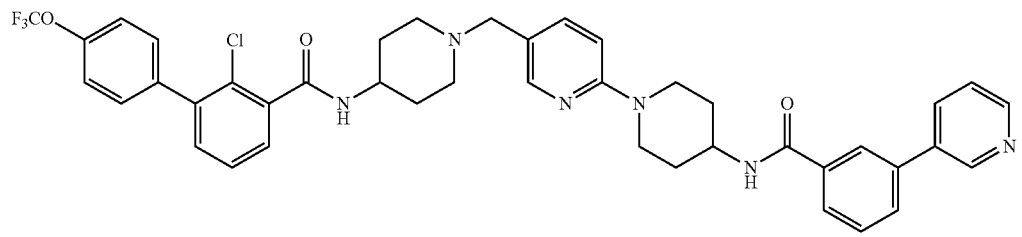

-continued
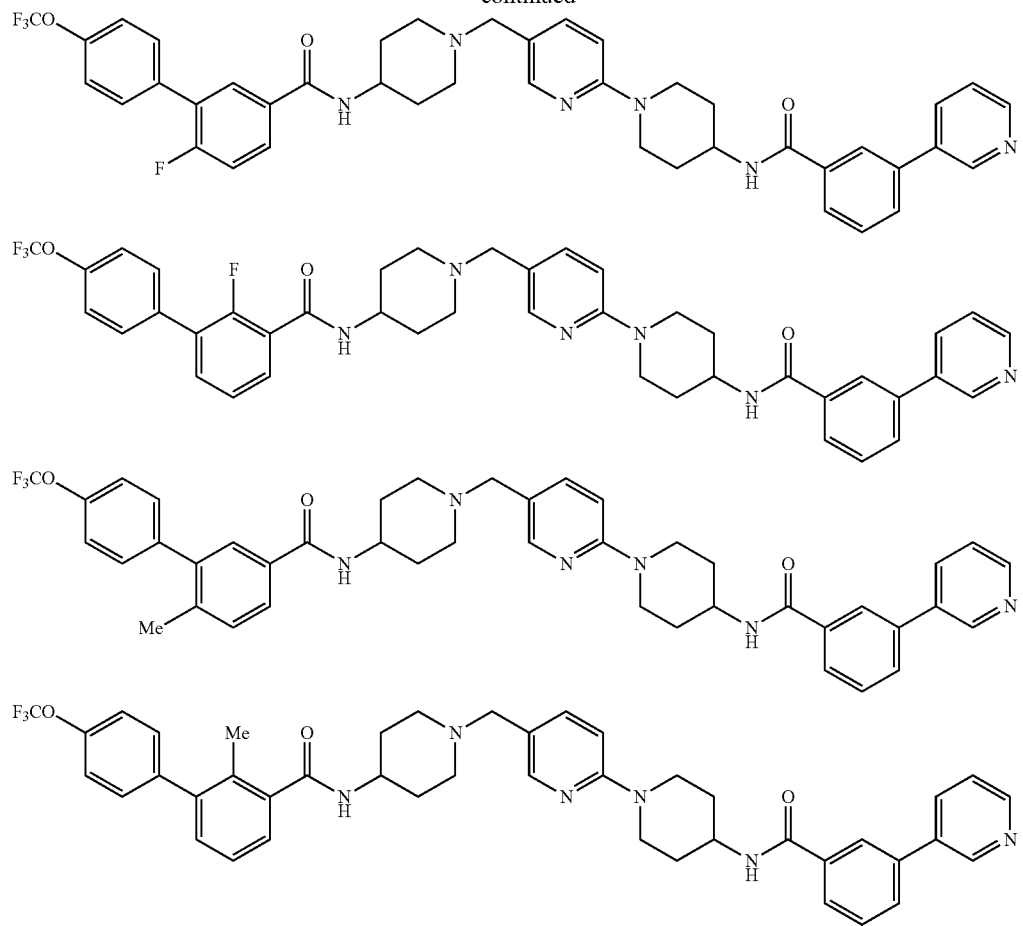
Scheme 15
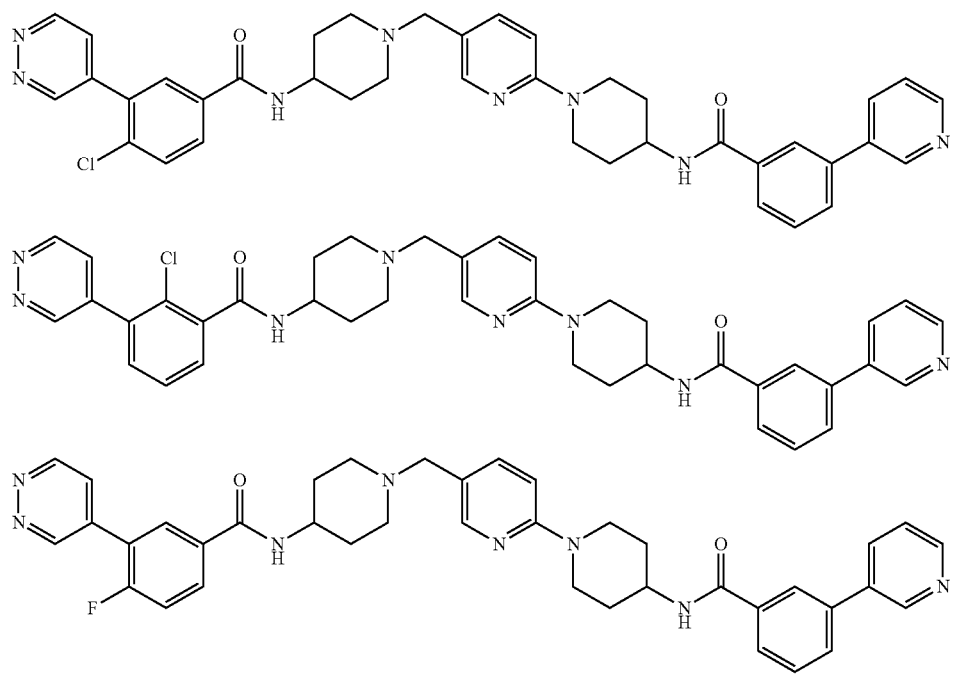

-continued
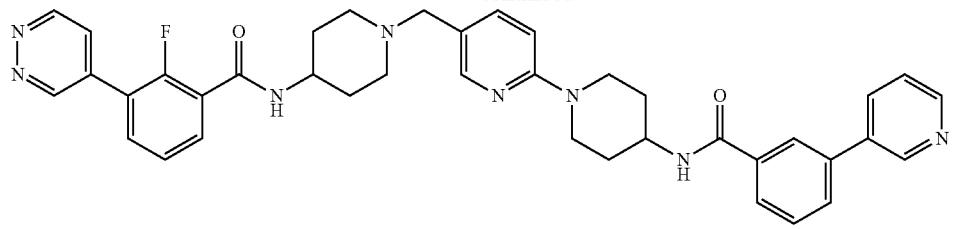
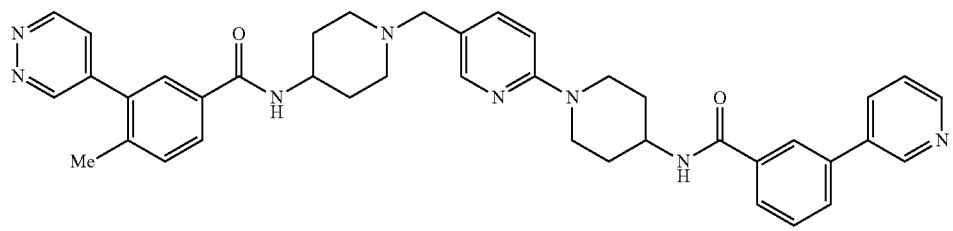
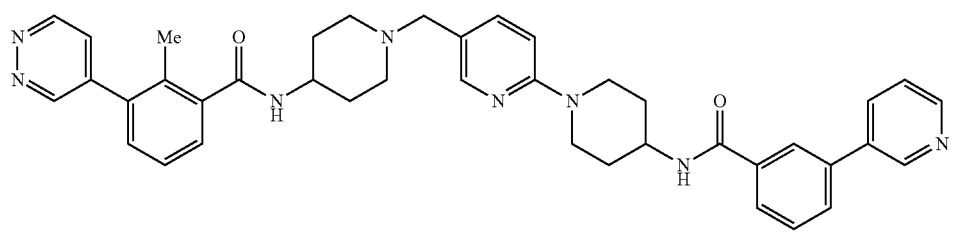
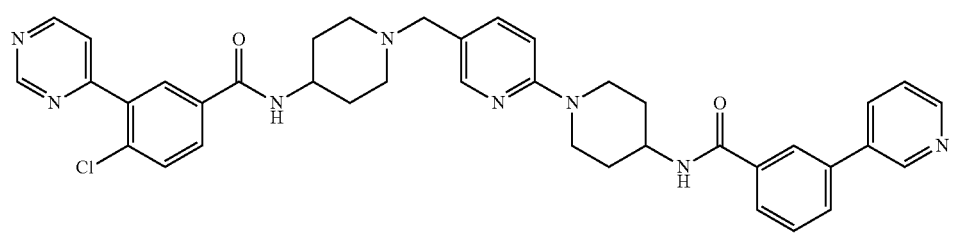
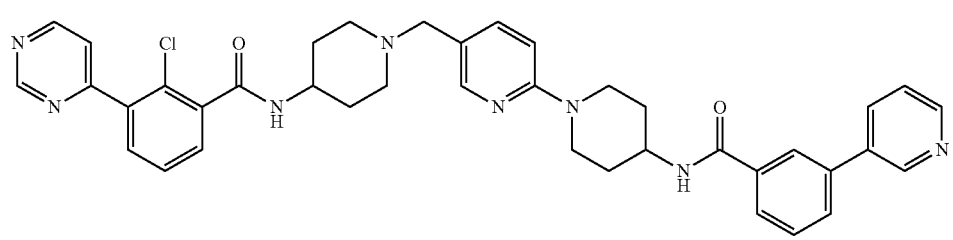
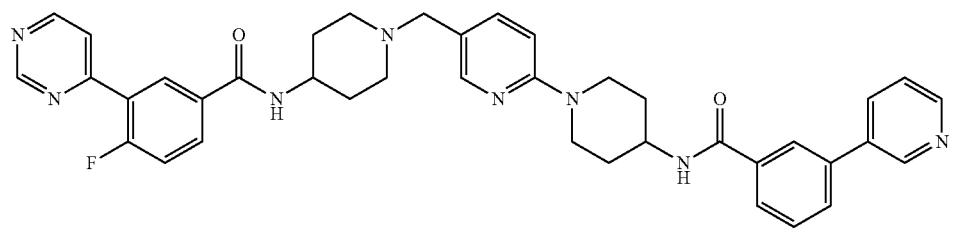
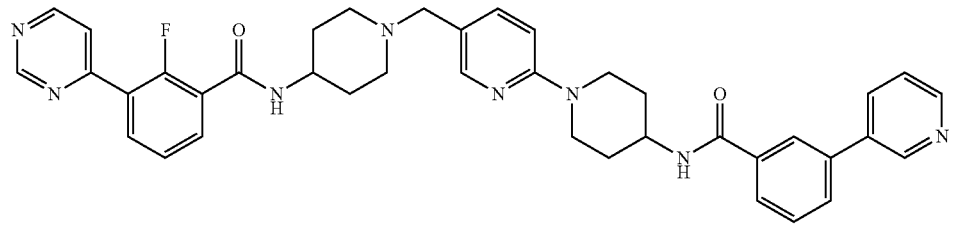

-continued
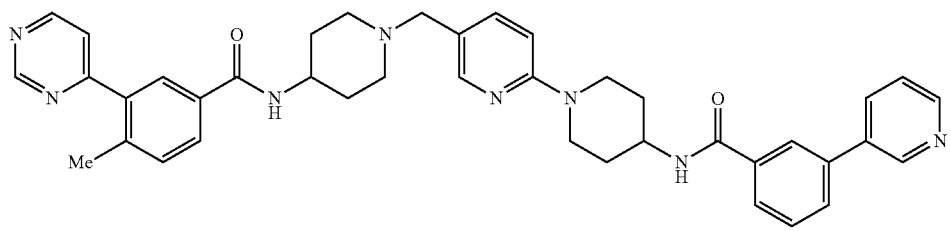
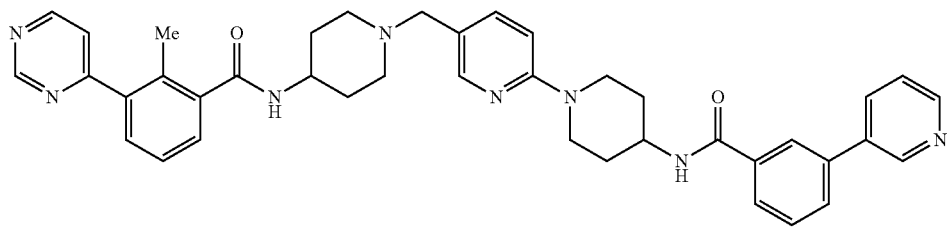
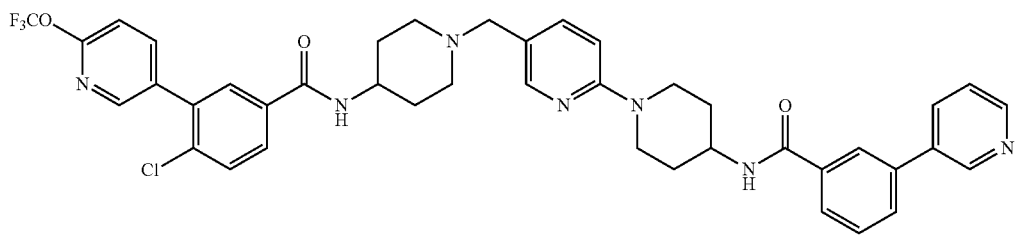
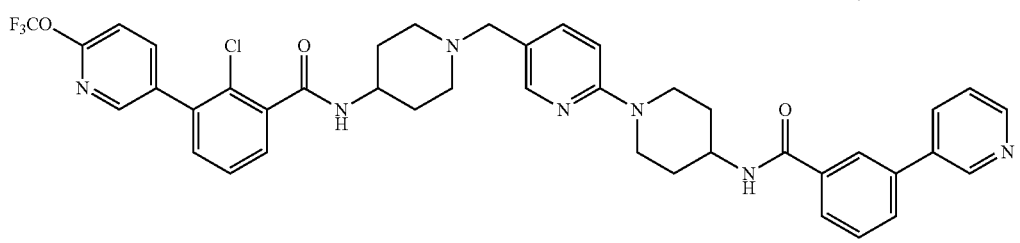
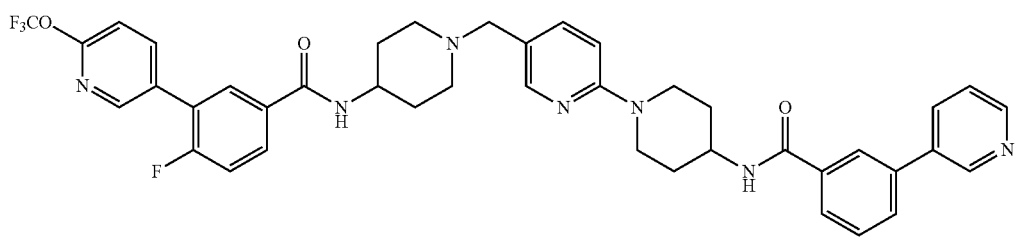
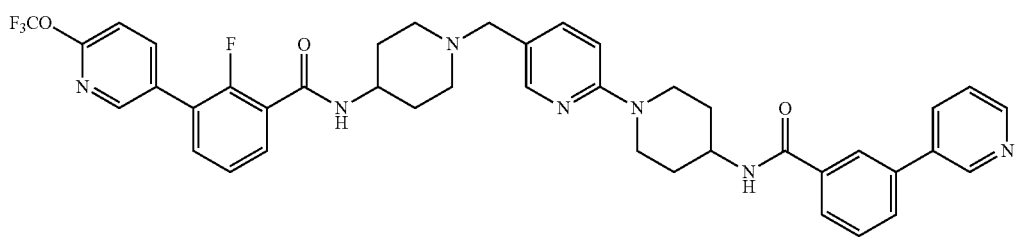
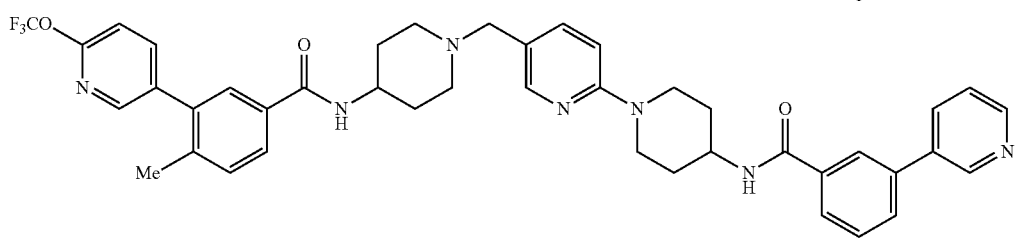

-continued

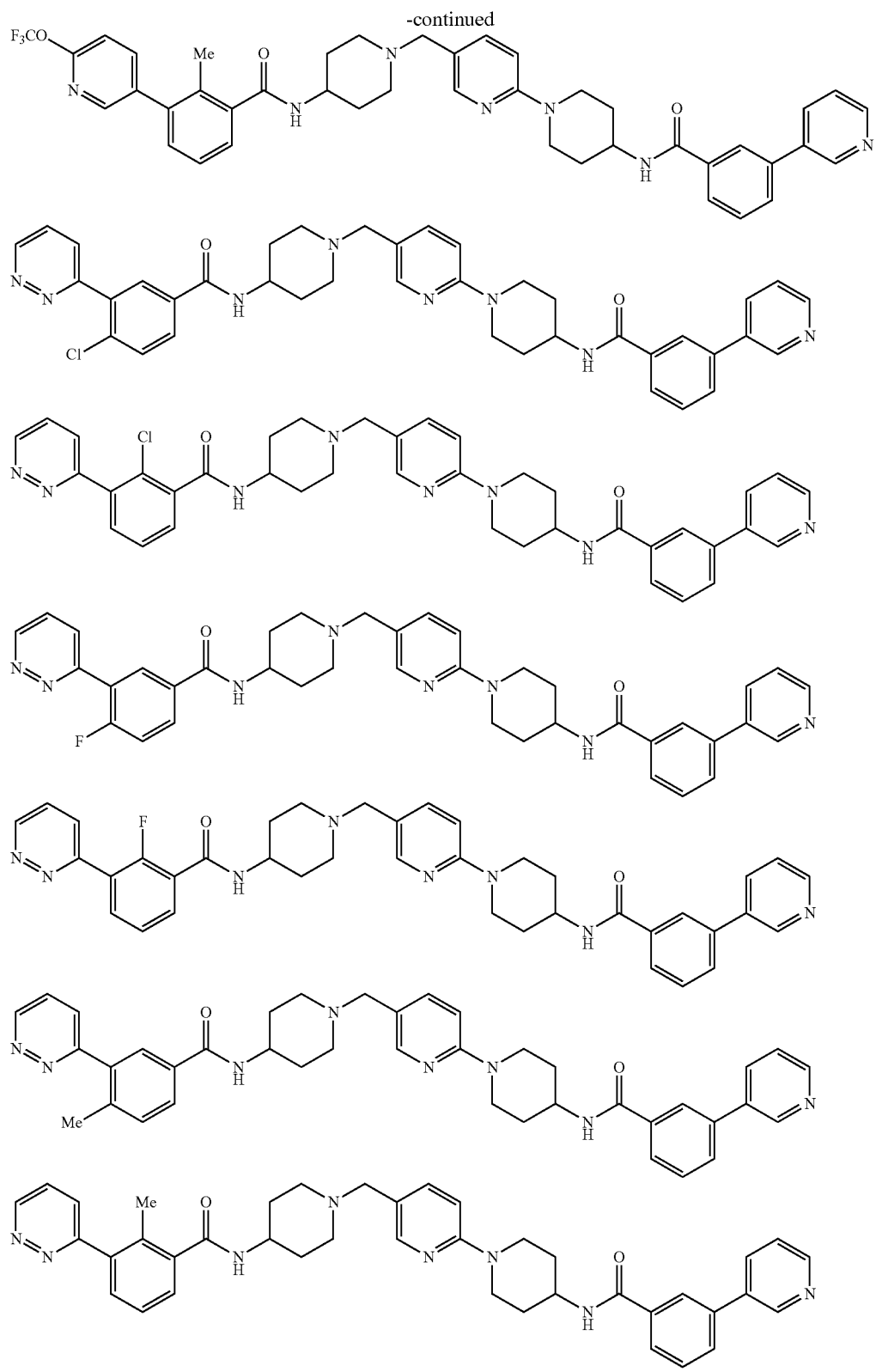

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and *acacia* or tragacanth; and pastilles comprising the compound in an inert base such as gelatin and glycerin or sucrose and *acacia*.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Pharmacology and Methods of Treatment.

The compounds of the present invention can be used in like manner as those described in U.S. Pat. No. 8,178,563 to Gao et al., the disclosure of which is incorporated herein by reference. Thus the present invention makes available methods and compounds for inhibiting activation of the hedgehog signaling pathway, e.g., to inhibit aberrant growth states resulting from phenotypes such as Ptc loss-of-function, hedgehog gain-of-function, smoothened gain-of-function or Gli gain-of-function, comprising contacting the cell with a compound of Formula I, in a sufficient amount to agonize a normal Ptc activity, antagonize a normal hedgehog activity, antagonize smoothened activity, or antagonize Gli activity e.g., to reverse or control the aberrant growth state.

Members of the Hedgehog family of signaling molecules mediate many important short- and long-range patterning processes during vertebrate development. Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation. The effects of developmental cell interactions are varied: responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation.

The vertebrate family of hedgehog genes includes three members that exist in mammals, known as Desert (Dhh), Sonic (Shh) and Indian (Ihh) hedgehogs, all of which encode secreted proteins. These various Hedgehog proteins consist of a signal peptide, a highly conserved N-terminal region, and a more divergent C-terminal domain. Biochemical studies have shown that autoproteolytic cleavage of the Hh precursor protein proceeds through an internal thioester intermediate which subsequently is cleaved in a nucleophilic substitution. It is likely that the nucleophile is a small lipophilic molecule which becomes covalently bound to the C-terminal end of the N-peptide, tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities.

An inactive Hedgehog signaling pathway is where the transmembrane protein receptor Patched (Ptc) inhibits the activity of Smoothened (Smo), a seven transmembrane protein. The transcription factor Gli, a downstream component of Hh signaling, is prevented from entering the nucleus through interactions with cytoplasmic proteins, including Fused and Suppressor of fused (Sufu). As a consequence, transcriptional activation of Hedgehog target genes is repressed. Activation of the pathway is initiated through binding of any of the three mammalian ligands (Dhh, Shh or Ihh) to Ptc. Ligand binding results in a reversal of the repression of Smo, thereby activating a cascade that leads to the translocation of the active form of the transcription factor Gli to the nucleus. Nuclear Gli activates target gene expression, including Ptc and Gli itself.

Increased levels of Hedgehog signaling are sufficient to initiate cancer formation and are required for tumor survival. These cancers include, but are not limited to, prostate cancer ("Hedgehog signalling in prostate regeneration, neoplasia and metastasis", Karhadkar S S, Boa G S, Abdallah N, Dhara S, Gardner D, Maitra A, Isaacs J T, Berman D M, Beachy P A., Nature. 2004 Oct. 7; 431(7009):707-12; "Inhibition of prostate cancer proliferation by interference with SONIC HEDGEHOG-GLI1 signaling", Sanchez P, Hernandez A M, Stecca B, Kahler A J, DeGueme A M, Barrett A, Beyna M, Datta M W, Datta S, Ruiz i Altaba A., Proc Natl Acad Sci USA. 2004 Aug. 24; 101(34):12561-6), breast cancer ("Hedgehog signaling pathway is a new therapeutic target for patients with breast cancer", Kubo M, Nakamura M, Tasaki A, Yamanaka N, Nakashima H, Nomura M, Kuroki S, Katano M., Cancer Res. 2004 Sep. 1; 64(17):6071-4), medulloblastoma ("Medulloblastoma growth inhibition by hedgehog pathway blockade", Berman D M, Karhadkar S S, Hallahan A R, Pritchard J I, Eberhart C G, Watkins D N, Chen J K, Cooper M K, Taipale J, Olson J M, Beachy P A., Science. 2002 Aug. 30; 297(5586):1559-61), basal cell carcinoma ("Identification of a small molecule inhibitor of the hedgehog signaling pathway: effects on basal cell carcinoma-like lesions", Williams J A, Guicherit O M, Zaharian B I, Xu Y, Chai L, Wichterle H, Kon C, Gatchalian C, Porter J A, Rubin L L, Wang F Y., Proc Natl Acad Sci USA. 2003 Apr. 15; 100(8):4616-21; "Activating Smoothened mutations in sporadic basal-cell carcinoma", Xie J, Murone M, Luoh S M, Ryan A, Gu Q, Zhang C, Bonifas J M, Lam C W, Hynes M, Goddard A, Rosenthal A, Epstein E H Jr, de Sauvage F J., Nature. 1998 Jan. 1; 391(6662):90-2), pancreatic cancer ("Hedgehog is an early and late mediator of pancreatic cancer tumorigenesis", Thayer S P, di Magliano M P, Heiser P W, Nielsen C M, Roberts D J, Lauwers G Y, Qi Y P, Gysin S, Fernandez-del Castillo C, Yajnik V, Antoniu B, McMahon M, Warshaw A L, Hebrok M., Nature. 2003 Oct. 23; 425(6960):851-6; "Widespread requirement for Hedgehog ligand stimulation in growth of digestive tract tumours", Berman D M, Karhadkar S S, Maitra A, Montes De Oca R, Gerstenblith M R, Briggs K, Parker A R, Shimada Y, Eshleman J R, Watkins D N, Beachy P A., Nature. 2003 Oct. 23; 425(6960):846-51), and small-cell lung cancer ("Hedgehog signalling within airway epithelial progenitors and in small-cell lung cancer", Watkins D N, Berman D M, Burkholder S G, Wang B, Beachy P A, Baylin S B., Nature. 2003 Mar. 20; 422(6929):313-7).

In accordance with the foregoing, the present invention further provides a method for preventing or treating any of the diseases or disorders described above in a subject in need of such treatment, which method comprises administering to said subject a therapeutically effective amount of a compound of Formula I or a pharmaceutically acceptable salt thereof. For any of the above uses, the required dosage will vary depending on the mode of administration, the particular condition to be treated and the effect desired.

4. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art. In some embodiments, a dosage from about 0.1 or 1.0 to about 250 or 500 mg/kg is used, with all weights being calculated based upon the weight of the active compound, including the cases where a salt is employed. The dosage may be administered one any suitable schedule, including but not limited to once, twice, or three times a day. The duration daily dosage may be from one or two days, or one or two weeks, to two, three, or four months, or more, depending on the condition being treated.

Compounds of the invention may be administered directly, or as prodrugs thereof. Pharmaceutically acceptable prodrugs as used herein refers to those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

The present invention is explained in greater detail in the following non-limiting Examples. The following abbreviations are used herein: Smo, Smoothened; Hh, Hedgehog; Ptc, Patched; Shh, Sonic Hedgehog; β-Arr2, β-Arresting; β-Arr2-GFP, β-Arrestin2-Green Fluorescent Protein chimera; Gli, Glioma-associated oncogene; GPCR; G-Protein-Coupled Receptor; V2R, Vasopressin2 receptor; HTS, High-Throughput Screening; WT; wild-type; PBS, phosphate-buffered saline; GCP, Granular Cell Precursor; HBBS, Hanks Balanced Salt Solution; DCC, N,N-Dicyclohexylcarbodiimide; TFA, Trifluoroacetic acid; HOBt, N-Hydroxybenzotriazole; DBU, 1,8-Diazabicyclo[5.4.0]undec-7-ene.

EXPERIMENTAL

Activated Smo shares important similarities with canonical G protein-coupled receptors (GPCRs), including an ability to undergo GPCR kinase-mediated phosphorylation and to recruit β-arresting (βarr2) proteins for endocytosis and signaling.

In our previous worker, we found that βarr2 binds Smo at the plasma membrane in an activation-dependent manner, and that the Smo antagonist cyclopamine inhibits the activity of Smo by preventing its phosphorylation and interaction with βarr2. These findings enabled the development of a versatile cell-based highthroughput imaging-based screening platform capable of identifying either agonists or antagonists of the pathway by the presence or absence of cyclopamine, respectively, in the assay. These assay formats led to the discovery of Smo agonist activity in a select subset of commonly used glucocorticoid medications[28] and Smo antagonist activity in piperonyl butoxide[29], a pesticide synergist present in over 1500 products[30] recently associated with delayed learning in children[31] and one of the top 10 chemicals detected in indoor dust[32]. Here, we report the use of this platform to search systematically for Smo inhibitors in small molecule chemical libraries. This effort resulted in the discovery of a number of active hits, including a low nanomolar Smo antagonist (compound A8) that binds to Smo receptors, inhibits the transcriptional activity of Gli, inhibits cell proliferation of neural precursor cells and prevents Hh-signaling dependent hair growth in mice. In contrast to GDC-0449, compound A8 binds the Smo mutant D473H recently associated with medulloblastoma disease progression and resistance to GDC-0449[17,25,33], thereby providing the basis of a strategy to treat resistant disease.

Materials and Methods

Reagents:

A library of 5740 compounds (Tripos Gold) were used for high-throughput screening. β-arresting green fluorescent protein (βarr2-GFP), wild-type Smo, Smo-663 mutant, and Gli-luciferase reporter have been previously described[27,28]. The Smo-D473H mutant construct was generated using the QuikChange site-directed mutagenesis kit (Stratagene). Purified Sonic Hedgehog was obtained from StemRD.

Cyclopamine was purchased from Toronto Research Chemicals. [$_3$H]-cyclopamine was purchased from American Radiolabeled Chemicals. GDC-0449 (Vismodegib), LDE-225 (NVP-LDE225, Erismodegib) and select hits identified from screening were synthesized by the Small Molecule Synthesis Facility at Duke University.

Primary High-Throughput Screening Assay:

U2OS cells stably expressing a chimera Smo-633 receptor and βarr2-GFP were used in HTS screening. Smo-633 was used in this assay because it produces a stronger signal than WT Smo in the βarr2-GFP translocation assay, but is otherwise pharmacologically similar[27,34]. The antagonist mode screening protocol used here to identify antagonists of Smo is similar to the protocol to identify Smo agonists described previously with the exception that cyclopamine pretreatment was not used prior to the addition of test compounds[28].

Smo Receptor Binding:

For competitive binding assays, U2OS cells overexpressing wild-type Smo or Smo-D473H mutant receptors were grown in 24-well plates and fixed with 4% (v/v) formaldehyde/PBS for 20 min at room temperature (RT). Cells were subsequently incubated for 2 h at RT in binding buffer (Hanks Balanced Salt Solution (HBSS) without $Ca_{2+}$ and $Mg_{2+}$) containing 25 nM of [$_3$H]-cyclopamine and a range of different concentrations of cyclopamine, GDC-0449, LDE-225 or A8 (from 0-10 μM). Cells were then washed with binding buffer and the bound [$_3$H]-cyclopamine was extracted in 200 μl of 0.1N NaOH and neutralized with 200 μl of 0.1N HCl. The amount of [$_3$H]-cyclopamine in the extracts was measured using a scintillation counter.

Gli-Luciferase Reporter Assay:

The Gli-luciferase assay was conducted in Shh-LIGHT2 cells, a clonal NIH3T3 cell line stably incorporating Gli-dependent firefly luciferase and constitutive Renilla luciferase reporters[35]. Cells were treated with purified Sonic Hedgehog protein (50 ng/mL) together with the corresponding compounds for 2 days. The reporter activity was determined by using the Dual-Luciferase Reporter Assay System (Promega).

Cell Proliferation:

Primary neuronal granular cell precursor (GCP) cells were obtained from the cerebellum of 7-day postnatal C57BL/6 mice and labeled with [$_3$H]-thymidine. Proliferation assays were performed as previously described[28].

Animal Studies:

Eight-week-old C57BL/6 female mice were shaved on the dorsal surface and depilated with Nair® (Carter-Wallace, New York, N.Y.). Briefly, the bottom half of the shaved area was treated with Nair for 2 min, and the depilated area rinsed with water to remove residual Nair. Compound A8 was dissolved in a vehicle of 95% acetone/5% DMSO at a concentration of 0.5 mM, and 30 μl of A8 solution or the vehicle were applied topically to the depilated area of mice daily for two weeks. Mice were anesthetized briefly using 3% isoflurane anesthetic inhalant during all procedures. Five mice were included in each treatment group. All animals were treated in accordance with protocols approved by Institutional Animal Care and Use Committee at Duke University.

Results

Identification of Compound A8 from Screening.

To identify novel Smo inhibitors, we screened chemical libraries using our confocal imaging, cell-based platform assay as the primary high-throughput screening assay. This assay derived from our discovery that co-expression of Smo and βarr2-GFP in cells results in an activation dependent translocation of βarr2-GFP into endocytic vesicles. βarr2-GFP distributes homogenously throughout the cytoplasm when expressed alone in cells (FIG. 1A)[28]. In marked contrast, cells co-expressing Smo-633 and βarr2-GFP localize βarr2-GFP into intracellular esicles as aggregates (FIG. 1B). Addition of a Smo antagonist, such as cyclopamine, inhibits the aggregation of βarr2-GFP, as demonstrated by the disappearance of intra-vesicular aggregates (FIG. 1C). Thus, small molecule inhibitors of Smo are identified by the loss of the punctate pattern. Upon screening of a library of 5740 compounds from Tripos, Inc. at a concentration of 5 μM, we identified 32 hit compounds that inhibited the formation of intracellular βarr2-GFP aggregates similar to that observed with cyclopamine treatment[36]. Hit compounds in this assay were confirmed by further evaluation in Gli-reporter and [$_3$H]-cyclopamine competition assays, and by testing new solid samples of the hit compounds. At 1 μM concentration, the positive control cyclopamine and hit compounds showed strong inhibition of the Gli-reporter activity[36].

Figure 2:
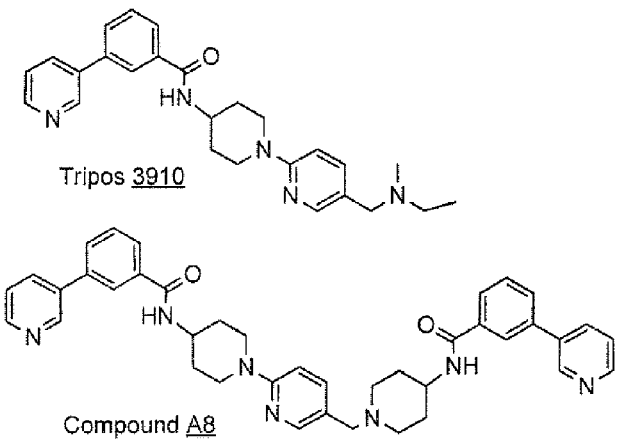
FIG. 2. Chemical structures of screening hits and synthesis of A8. (A) Structures of Tripos 3910 and Compound A8. (B) Synthesis of Compound A8.
Figure 2:
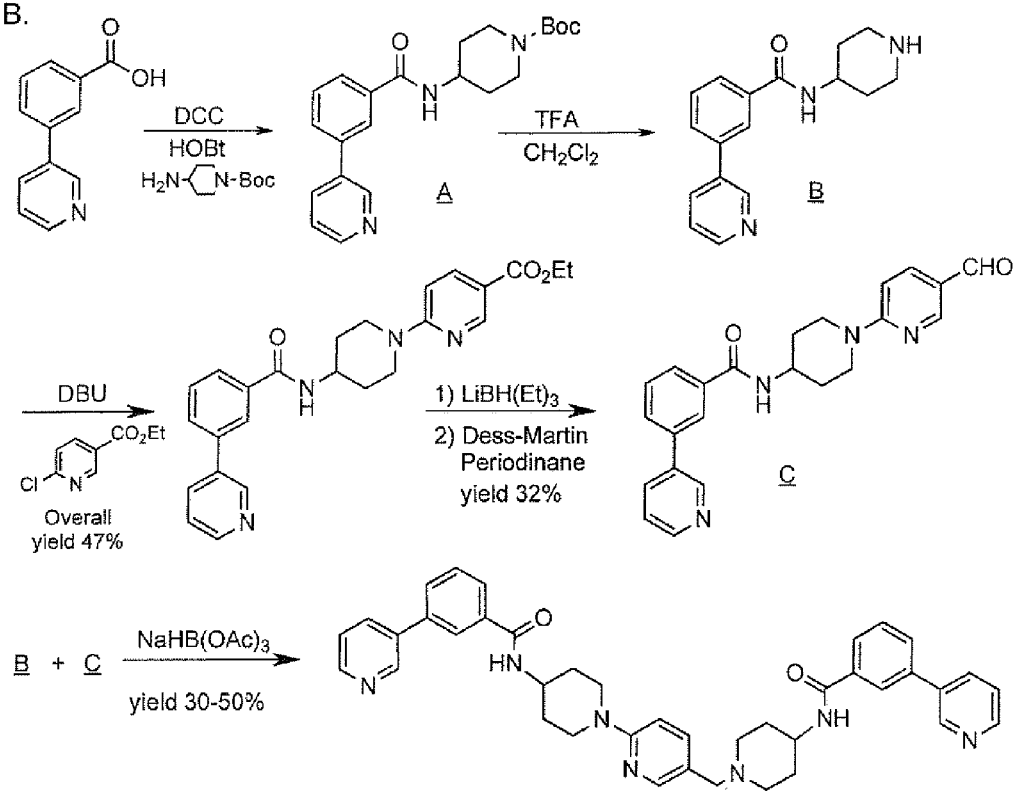

Of the hits obtained from screening, one hit compound (Tripos 3910) (FIG. 2A) synthesized at Duke based on the structure assigned to the material by Tripos, had substantially reduced Smo antagonist activity compared to the previous test samples. Reduced activity associated with this structure was confirmed upon subsequent purification of the Tripos sample in which the major component in the library sample agreed for structure and was less active. Instead, the active substance was found to be a small impurity isolated from the library sample. Storage of the active impurity at room temperature in a DMSO or methanolic solution for 1 week retained activity. Subsequent characterization of this impurity by high-resolution mass spectrometry (HRMS) and by extensive NMR analysis allowed assignment of structure to the impurity as shown for Compound A8 (FIG. 2A). Confirmation of the structural assignment was achieved by synthesis of authentic material using the route described in FIG. 2B. Synthesized material matched the isolated material from the library sample by extensive NMR analysis, HRMS, TLC and HPLC. The activity of the synthesized material was confirmed upon testing the synthesized material in the primary Smo/βarr2-GFP assay (FIG. 1D).

Compound A8 is a Competitive Antagonist of Smo.

Figure 3:
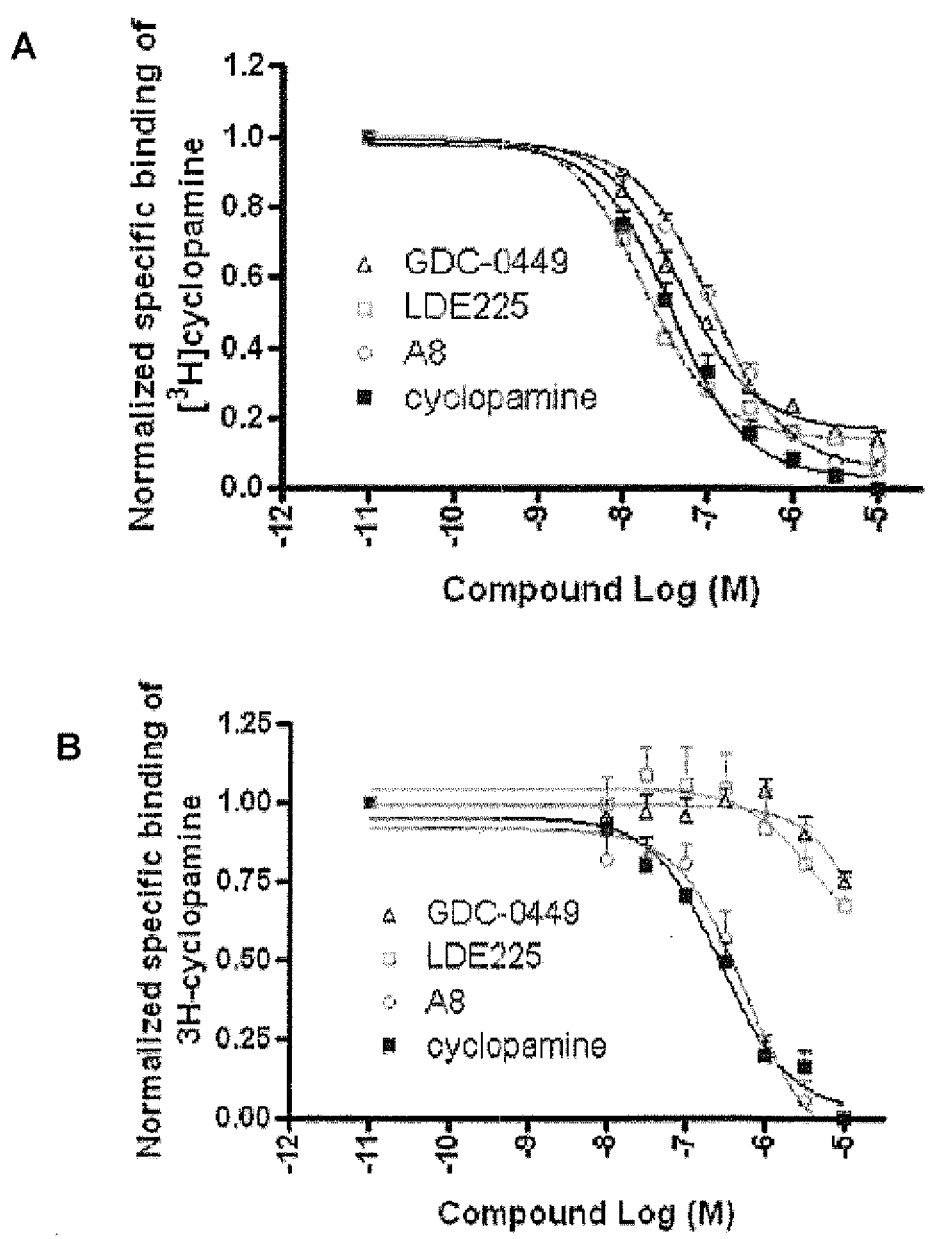
FIG. 3. Compound A8 competitively displaces [$_3$H]-cyclopamine binding to wild-type Smo and mutant Smo-D473H. Competitive binding of [$_3$H]-cyclopamine with Smo antagonists was performed in fixed U2OS cells overexpressing wild-type Smo (A) and Smo-D473H (B). Data were normalized to the maximal binding of [$_3$H]-cyclopamine over baseline. The displacement data were analyzed by fitting to a one-site competition curve using Graphpad Prism. Data were acquired in triplicates from three independent experiments and are presented as the mean±SEM.

To further characterize the binding of compound A8 to Smo, we tested the ability of A8 to competitively displace [$_3$H]-cyclopamine from Smo in U2OS cells overexpressing wild-type Smo. Cyclopamine, GDC-0449, LDE-22537 and A8 completely displaced 25 nM of [$_3$H]-cyclopamine from Smo with similar affinities, Ki=12.7±1.7 nM, 16.2±2.1 nM, 6.0±1.4 nM and 37.9±3.7 nM, respectively (FIG. 3A). Given the importance of mutations in resistance to anticancer therapies, we tested whether A8 is capable of binding to a mutant Smo receptor (Smo-D473H) recently associated with clinical resistance and disease progression to GDC-0449 therapy[17,25,33]. To this end, we used U2OS cells overexpressing Smo-D473H receptors, and consistent with the previous report, GDC-0449 was largely ineffective at competing for binding the mutant receptors and only partially displaced [$_3$H]-cyclopamine at high concentration (10 μM) (FIG. 3B). Another leading Smo antagonist in clinical trials, LDE-225 (Erismodegib), was also largely ineffective. However, both A8 and cyclopamine were able to completely displace [$_3$H]-cyclopamine from Smo-D473H receptors with $K_i$s of 478±123 nM and 232±53 nM, respectively (FIG. 3B). Taken together, these results suggest that A8 competes with cyclopamine for the same binding site on Smo and binds both wild-type Smo and the Smo-D473H mutant receptor.

Compound A8 Inhibits Gli Activity and Proliferation of Mouse Cerebellar Granular Cell Precursor (GCP) Cells.

We next examined the inhibitory effect of compound A8 on Hh signaling. Since activation of Smo is known to increase the transcriptional activity of Gli, a Gli-luciferase reporter assay was used to measure inhibition of Smo activation[38]. As expected of an inhibitor of hedgehog signaling targeting Smo, compound A8 effectively inhibited Shh-induced Gli reporter activity ($IC_{50}$=2.6±0.4 nM) (FIG. 4A), Inhibition by A8 was comparable to that of GDC-0449 ($IC_{50}$=1.5±0.2 nM) and considerably more potent than Cyclopamine ($IC_{50}$=484±122 nM).

Figure 4:
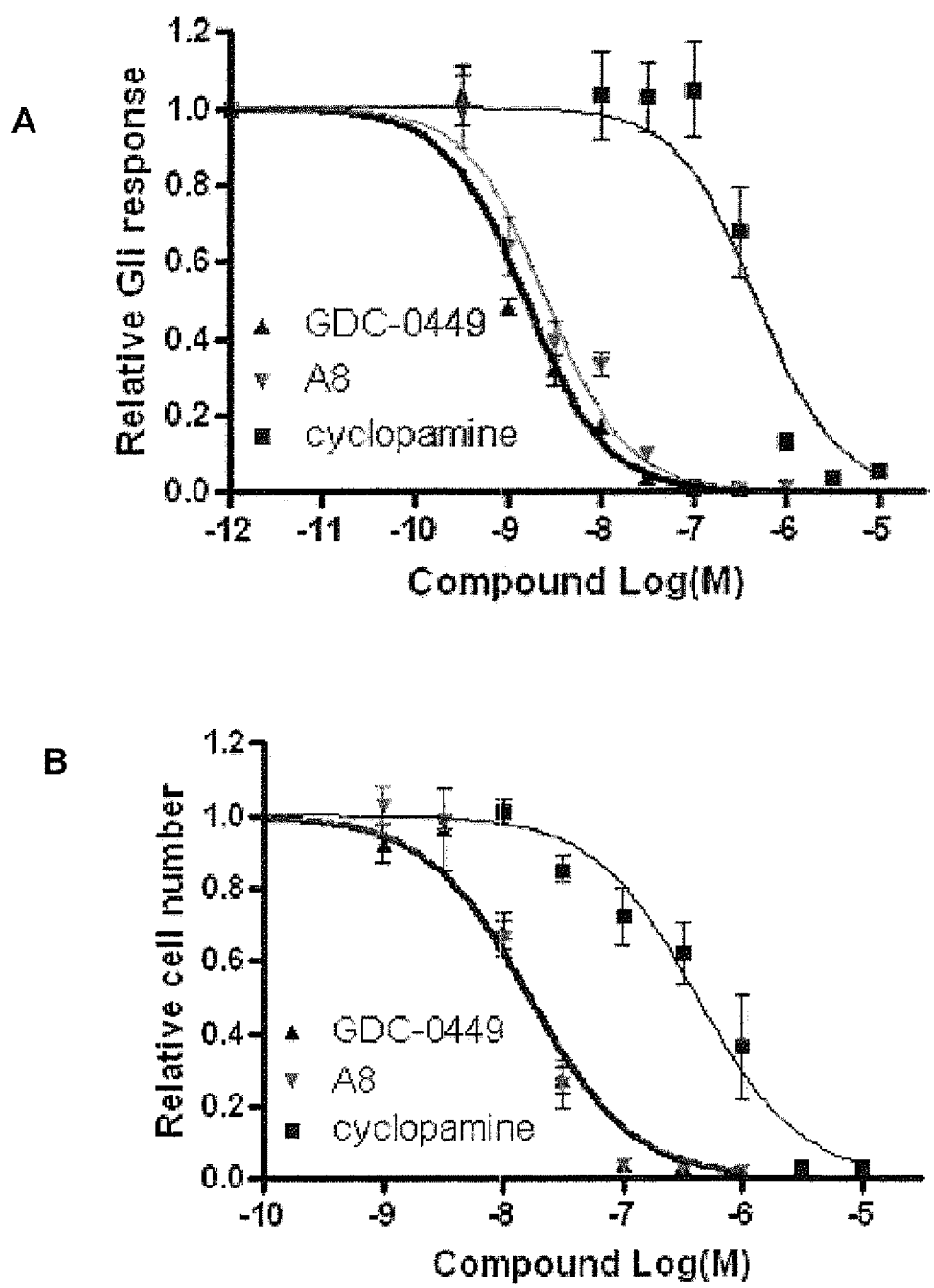
FIG. 4. Compound A8 inhibits Gli-reporter activity and GCP proliferation. (A) Gli-luciferase response in Shh-LIGHT2 cells treated for 30 hours with Shh in the absence or presence of increasing concentrations of cyclopamine (Cyc), GDC-0449, or A8. (B) GCP cells were treated for 48 hours with Shh in the absence or presence of increasing concentrations of Cyc, GDC-0449, or A8. Cells were then exposed to [$_3$H]-thymidine for 16 h and [$_3$H]-thymidine incorporation was measured. Data were fit using Graphpad Prism (mean±SEM, n=3).

Proliferation of cerebellar GCP cells requires Hh signaling[39]. Thus, a mouse GCP proliferation assay was performed to assess the hedgehog growth-inhibiting effects of compound A8[28]. We found that compound A8 and GDC-0449 were potent inhibitors of GCP proliferation with $IC_{50}$s of 16.6±2.3 nM and 16.4±2.5 nM, respectively (FIG. 4B). Consistent with the finding that higher concentration of cyclopamine was needed to inhibit Gli activity compared to A8 and GDC-0449 (FIG. 4A), cyclopamine was also a less potent inhibitor of GCP proliferation ($IC_{50}$=414±73 nM). Collectively, these results indicate that A8 is a potent inhibitor of Smo activity and is capable of inhibiting Hh-dependent Gli transcription and cell proliferation in vitro.

Compound A8 Inhibits Hair Regrowth in Mouse.

Hedgehog signaling plays a key role in regulating hair follicle growth[40]. To determine the efficacy of the novel Smo inhibitor A8 in suppressing Hh signaling in vivo, we used a model of hedgehog inhibition that examines inhibition of hair-growth[41-43]. Eight-week old Female C57BL mice in telogen phase of the hair cycle were used in these experiments[44]. Chemical depilation with Nair® induces anagen phase and regrowth of hair by activating the Hh signaling pathway. In our experiments, most of the hair on the back of vehicle treated mice grew back 2 weeks after removal with Nair (data not shown). In contrast, Hh-induced hair growth was largely inhibited in the A8 treated group, suggesting that A8 also functions as an inhibitor of Hh signaling in vivo (data not shown).

DISCUSSION

Following the discovery of oncogenic Ptc mutations, increasing numbers of studies have demonstrated hyperactivation of Hh signaling plays a critical role in promoting the development and progression of various cancers[21]. As a result, a number of small molecule inhibitors of Hh signaling targeting Smo have progressed into clinical trials, one of which was recently approved. Unfortunately, drug resistance has already been described in which mutation of the target decreases affinity of the drug to the target, a common resistance mechanism seen with other recent anticancer drugs. Thus there is a need for potent inhibitors of wild-type Smo with activity against a spectrum of mutations in Smo. This need has prompted recent reports of second generation inhibitors that offer a degree of activity against relevant mutations in Smo[45-48]. In the work described herein, we utilized a robust and versatile cell-based assay platform based on Smo receptor biochemistry developed in our lab. This assay allowed the identification a lead compound with nanomolar inhibitory activity against wild-type Smo also capable of binding a mutated form of Smo associated with clinical resistance.

The Smo/βArr2-GFP high throughput assay platform exploited here is based on our discovery that activated wild-type Smo or Smo-633 binds βarr2-GFP and changes its cellular distribution[27,28]. Addition of a Smo antagonist, such as cyclopamine inhibits the aggregation of Smo-633 with βarr2-GFP. Upon screening small molecule chemical libraries at a concentration of 5 μM, hits were identified by the disappearance of βarr2-GFP intra-vesicular aggregates in cells, similar to the disappearance of aggregates observed with cyclopamine. To control for receptor specificity and to rule-out non-specific mechanisms, hits were cross-screened in the same assay format using the vasopressin2 receptor (V2R), a different seven-transmembrane receptor. In this control assay, cells transfected with V2R and βarr2-GFP are stimulated with the agonist arginine vasopressin. Stimulation causes βarr2-GFP to aggregate and produces a punctuate pattern in cells. Aggregation of V2R and βarr2-GFP is not inhibited by the Smo antagonist cyclopamine[29]. This control assay helps ensure the mechanism of inhibition is Smo receptor specific and allows molecules with non-specific mechanisms of inhibition to be ruled-out. Only compounds that inhibited aggregation of Smo and did not inhibit aggregation of V2R were evaluated in confirmatory assays.

The Smo/βArr2-GFP assay is a versatile assay platform that provides the ability to screen for antagonists or agonists by a small change in the screening protocol. Screening in the antagonist mode is as described above. Screening in the agonist mode is accomplished by the addition of 0.1 μM of cyclopamine to the cells prior to screening test libraries[28]. In the agonist mode, active compounds are identified by the appearance of a green punctate pattern in the cells. The ability to screen cells in an agonist or antagonist mode provides significant advantages to chemical genetic screening approaches while also providing a cellular context to identify molecules with unique mechanisms of action. The follow-up assays used here clearly demonstrate the ability of this innovative assay format to identify authentic inhibitors of Smo that inhibit hedgehog signaling.

CONCLUSIONS

In summary, a novel high-throughput, cell-based assay platform based on a fundamental finding that activated Smo causes the translocation of βArr2 was capable of identifying Smo antagonists in chemical screening libraries. Here, the assay identified a potent inhibitor of hedgehog signaling and is capable of binding both wild-type and a mutated form of Smo associated with clinically resistance in medulloblastoma.

Synthesis and Characterization of Compound A8

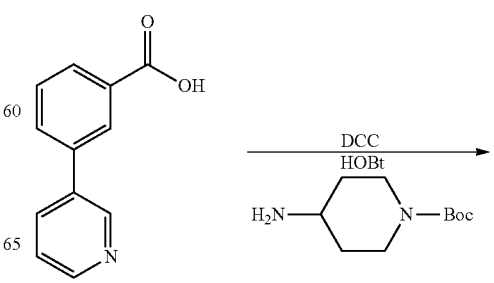

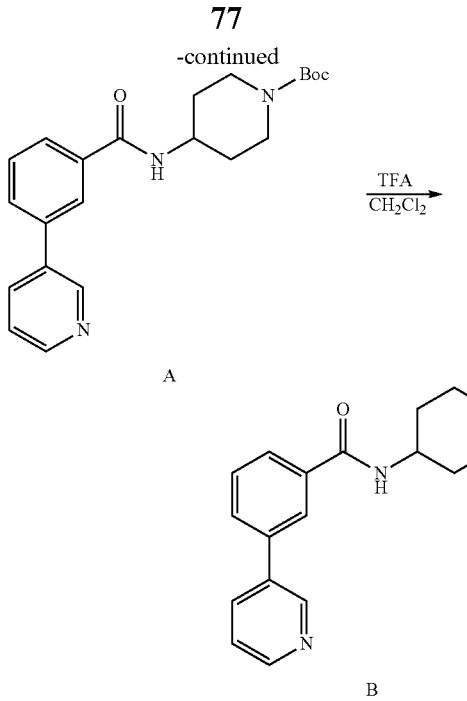

A

B

Synthesis of Amine B

To a flask containing 6.4 g (32.1 mmol) of 3-pyrid-3-ylbenzoic acid (Maybridge), 4.6 g (34 mmol) HOBt-hydrate, was added dry THF (40 mL) and methylene chloride (400 mL). To the heterogeneous mixture was added 6.88 g (33.4 mmol) Dicyclohexylcarbodiimide (DCC), followed by 6.75 g (33.7 mmol) of 4-Amino-1-Boc-piperidine (Aldrich). The reaction mixture became nearly homogeneous before a fine white precipitate is observed. The reaction was followed by TLC (5% MeOH/CH2Cl2) until complete. Upon completion, the reaction mixture was filtered and the filtrate concentrated to dryness. The residue was triturated with hot EtOAc (180 mL), filtered and the solids washed with cold EtOAc. The filtrate was then concentrated to dryness, and re-dissolved in 30-40 mL CH2Cl2 before adding 21 g of SiO2 and concentrating the mixture to dryness. The solids were eluted on 220 g of SiO2 starting with 1:1 EtOAc/CH2Cl2 and increasing to 100% EtOAc. The desired fractions were combined, heptane was added, and the solution concentrated to give 10.4 g (85%) of the Boc-piperidine Amide A as a white solid.

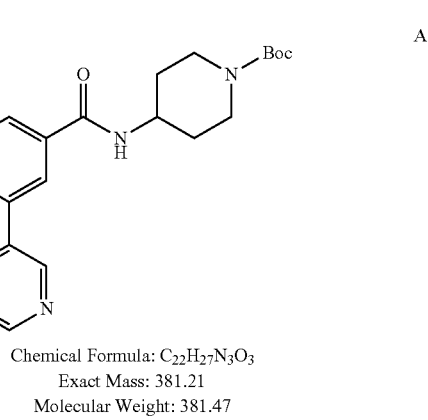

Chemical Formula: $C_{22}H_{27}N_3O_3$
Exact Mass: 381.21
Molecular Weight: 381.47

A $^1$HNMR (300 MHz, CDCl3)=8.85 (s, 1H), 8.61 (dd, J=4.7, 3.1 Hz, 1H), 7.98 (s, 1H), 7.90 (m, 1H), 7.72 (m, 2H), 7.54 (t, J=8 Hz, 1H), 7.38 (m, 1H), 6.17 (d, J=8 Hz, 1H), 4.14 (br m, 3H), 2.91 (t, J=7 Hz, 2H), 2.05 (d, J=7 Hz, 2H), 1.49 (s, 9H). MS(ESI+)=382 (M+1), 282 (M−Boc+1).

To a flask equipped with a gas outlet was added 10.5 g Boc-piperidine Amide A under an argon atmosphere and 630 mL of dry CH2Cl2. To this solution under a slow stream of argon was added 42 mL of trifluoroacetic acid. The progress of the reaction was followed by TLC (5% MeOH/CH2Cl2). After ca. 3 hrs., ca. 50 mL of 10M NaOH was added slowly to the reaction mixture as the mixture was cooled in an ice-bath. After the addition of NaOH was complete, water and brine were added. The CH2Cl2 layer was separated, and the aqueous layer extracted extensively with CH2Cl2 (ca. 5-6 times), until no product was observed in the CH2Cl2 layer by TLC (20% MeOH/Ch2Cl2). The CH2Cl2 layers were combined, dried over Na2SO4 and filtered. To this solution was added heptane, and the solution concentrated to give 8.1 g (1.04%) of Amine B as a white solid. This material was split, with 1.9 g retained for later coupling, and the remainder taken on directly into the next step.

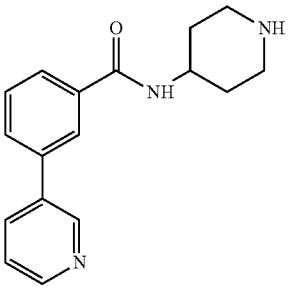

B

Chemical Formula: $C_{17}H_{19}N_3O$
Exact Mass: 281.15
Molecular Weight: 281.35

$^1$HNMR (300 MHz, CDCl3)=8.85 (d, J=1.8 Hz, 1H), 8.61 (dd, J=5, 1.5 Hz, 1H), 7.99 (t, 1.8 Hz, 1H), 7.90 (dt, J=8, 1.8 Hz, 1H), 7.73 (m, 2H), 7.54 (t, J=8 Hz, 1H), 7.38 (m, 1H), 6.15 (d, J=8 Hz, 1H), 4.11 (m, 1H), 3.12 (m, 2H), 2.79 (dt, J=11, 2.6 Hz, 2H), 2.07 (d, J=9 Hz, 2H), 1.45 (m, 3H). MS(ESI+) m/z=282 (M+1)

Synthesis of Aldehyde C

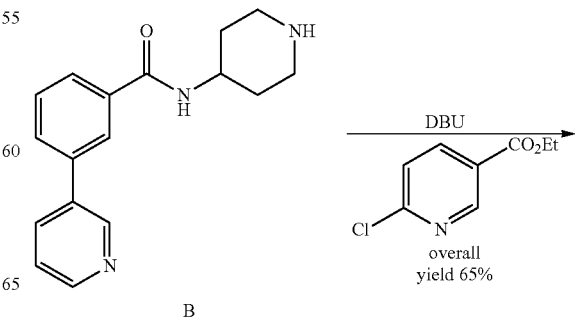

B overall yield 65%

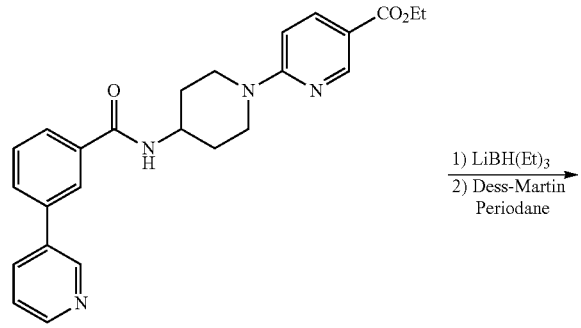

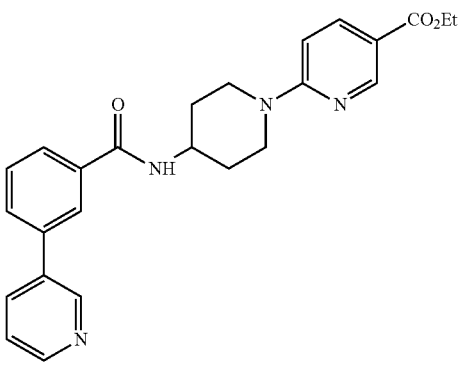

Chemical Formula: $C_{25}H_{26}N_4O_3$
Exact Mass: 430.20
Molecular Weight: 430.50

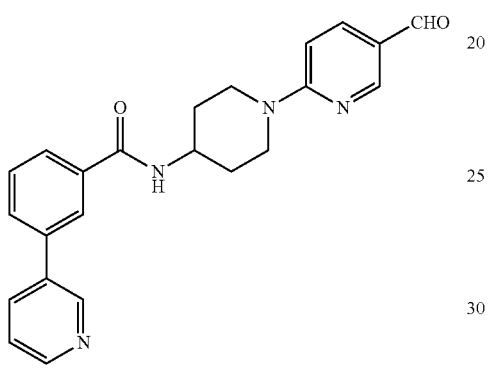

C $^1$HNMR (300 MHz, CDCl3)=8.80 (br s, 1H), 8.77 (br s, 1H), 8.58 (d, J=4.8, 1H), 8.00 (d, J=2 Hz, 1H), 7.97 (br s, 1H), 7.87 (m, 1H), 7.7 (m, 2H), 7.51 (t, J=8 Hz, 1H), 7.34 (m, 1H), 6.60 (d, J=9 Hz, 1H), 6.36 (d, J=8 Hz, 1H), 4.45 (d, 1=13 Hz, 2H), 4.31 (q, J=7 Hz, 3H), 3.11 (t, J=12 Hz, 2H), 2.15 (d, J=10 Hz, 2H), 1.54 (m, 2H), 1.35 (t, J=7 Hz, 3H). MS(ESI+) m/z=431 (M+1).

To a flask equipped with a short-path distillation head was added 6.2 g (ca. 22.06 mmol) of Amine B, 135 mL acetonitrile, 50 mL absolute EtOH (200 pf). The mixture was heated and ca. 10 mL of solvent was distilled-off to remove water. To the remaining solution under an argon atmosphere was added 4.29 g (23.17 mmol) of the ethyl 6-chloropyridine-3-carboxylate (Aldrich), followed by 4.6 mL (30.89 mmol) DBU, and the reaction mixture heated between 70-80° C. until complete by TLC (2% MeOH/CH2Cl2, 20% MeOH/CH2Cl2) with additional chloropyridine added if needed to drive reaction to completion. After completion, the reaction mixture was cooled to room temperature and concentrated to dryness. The residue was dissolved in CH2Cl2 (150 mL) (some precipitate remains), and the CH2Cl2 suspension was washed 3×100 mL with a 1:1 solution of saturated ammonium chloride/H2O solution. The aqueous layers were combined and washed with CH2Cl2 (4×50 mL). The CH2Cl2 layers were combined and dried with Na2SO4, filtered, and concentrated to a white solid. To the solid was added CH2Cl2 (50 mL), MeOH (ca. 5 mL) and 11 g SiO2, and the resultant mixture concentrated. The solid was purified on a column of 220 g SiO2 packed in 2% MeOH/CH2Cl2 by eluting with a gradient of 2-9% MeOH/CH2Cl2. The desired fractions were concentrated and dried under high-vacuum overnight to give 6.2 g (65%) of the amine-pyridylester adduct.

To a dry 3-necked round-bottomed flask equipped with a low-temperature thermometer was added under an argon atmosphere, 1.05 g (2.44 mmol) of the amine-pyridylester adduct and 50 mL of dry THF. The mixture was cooled to −72° C. and 14.7 mL (14.7 mmol) of 1M lithium triethylborohydride in THF was added slowly along the inside walls of the flask over a period of ca. 30 min. The reaction mixture became a deep red color. After stirring for an additional 10 min, TLC (6% MeOH/CH2Cl2) indicated the starting material was mostly consumed. After 2 hours, ca. 1-1.5 mL of dimethylethyl amine was added and the mixture stirred for ca. 3-5 min. The cold reaction mixture was then poured quickly into a saturated solution of ammonium chloride at 15° C. The red color dissipates giving way to a yellow suspension. To the mixture was added EtOAc (100 mL). The pH of the aqueous layer was 8. The mixture was stirred for 5-10 min, before the aqueous layer was separated and washed with 1×50 mL EtOAc. The EtOAc layers were then combined and washed consecutively with saturated ammonium chloride, then brine, and dried with Na2SO4. The EtOAc solution was filtered, and to this solution was added a total of 13-15 mL of SiO2, and the resultant suspension was concentrated to dryness. The solids were purified by eluting them from a column of 100 mL SiO2 packed in 5% MeOH/CH2Cl2, with a gradient of 5-10% MeOH/CH2Cl2. The desired fractions were combined, heptane was added, and the solution concentrated to give 0.44 g (46%) of the benzylic alcohol intermediate.

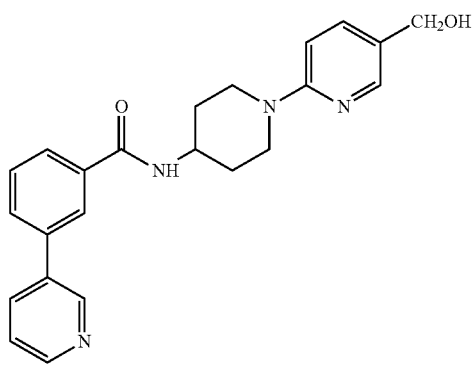

Chemical Formula: C$_{23}$H$_{24}$N$_4$O$_2$
Exact Mass: 388.19
Molecular Weight: 388.46

$^1$HNMR (CDCl3, 500 MHz)=8.84 (d, J=2.7, 1H), 8.62 (dd, J=4.8, 1.7 Hz, 1H), 8.16 (d, J=2.6 Hz, 1H), 7.98 (br s, 1H), 7.91 (dt, J=8.4 Hz, 2.6, 1H), 7.75 (d, J=8.6 Hz, 1H), 7.74 (d, J=8.6 Hz, 1H), 7.56 (d, J=7.6, 1H), 7.53 (d, J=2.7 Hz, 1H), 7.41 (dd, J=8, 3 Hz, 1H), 6.73 (d, J=9 Hz, 1H), 6.14 (d, J=7 Hz, 1H), 4.56 (s, 1H), 4.3 (m, 4H), 3.08 (dt, J=12, 3 Hz, 2H), 2.16 (d, J=12 Hz, 2H), 1.6 (m, partially obscured by H2O peak). MS(ESI+) m/z=371 (M+1−H2O)

To 0.283 g (0.73 mmol) of benzylic alcohol in 30 mL of dry CH2Cl2 was added 0.4 mL anhydrous pyridine. To this solution was added dropwise over ca. 1 min, 3 mL of a 0.3M solution of Dess-Martin periodinane (DMP) (Aldrich). The reaction mixture became a fine suspension before producing a golden color. The reaction progress was followed by TLC (8% MeOH/CH2Cl2). After ca. 30 min, a 1:1:1 solution of 10 mL 5% sodium thiosulfate, 10 mL saturated sodium bicarbonate and 10 mL H2O were added and the resultant mixture stirred rapidly for 20 min. The CH2Cl2 layer was separated and the aqueous layer was washed 3 times with CH2Cl2. The CH2Cl2 layers were combined and washed 3 times with water (pH-9-10), dried with Na2SO4, and filtered. Heptane was added to the filtrate and the solution was concentrated to a residue that was placed under high vacuum to remove residual pyridine. The residue was then chromatographed on SiO2 with a gradient of 3-5% MeOH/CH2Cl2. The desired fractions were combined, heptane was added and the solution concentrated to give 0.190 g (68%) of the aldehyde C as a white foam.

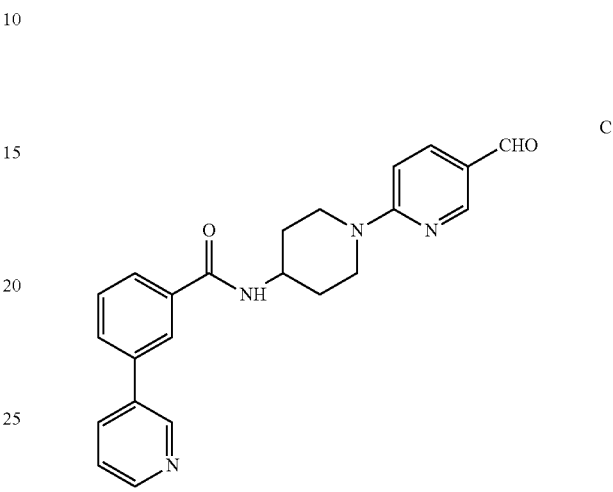

Chemical Formula: C$_{23}$H$_{22}$N$_4$O$_2$
Exact Mass: 386.17
Molecular Weight: 386.45

$^1$HNMR (CDCl3, 500 MHz)=9.79 (s, 1H), 8.86 (d, J=2 Hz, 1H), 8.63 (dd, J=4.8, 2 Hz, 1H), 8.57 (d, J=2 Hz, 1H), 7.99 (t, J=2 Hz, 1H), 7.94 (dd, J=9, 2 Hz, 1H), 7.91 (dt, J=8, 2 Hz, 1H), 7.74 (m, 2H), 7.56 (t, J=8.7 Hz, 1H), 7.40 (m, 1H), 6.73 (d, J=8.6 Hz, 1H), 6.15 (d, J=8 Hz, 1H), 4.57 (d, J=14.5 Hz, 2H), 4.37 (m, 1H), 3.21 (dt, J=12.6, 2.6 Hz, 2H), 2.23 (m, 2H), 1.6 (H20 peak obscures peaks). MS (ESI+) m/z=387 (M+1)

Compound A8

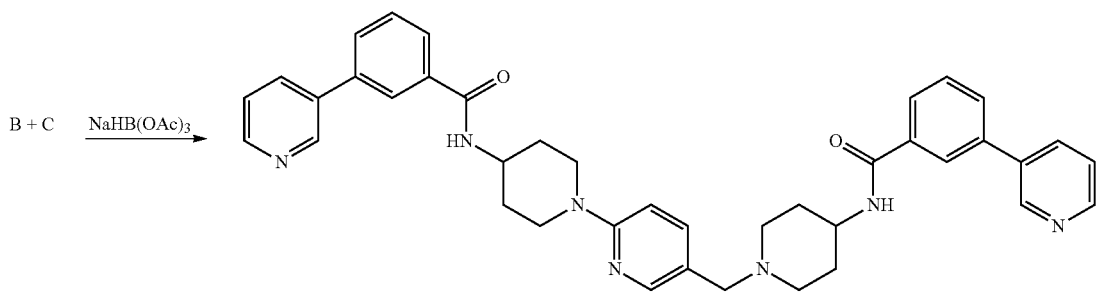 [SMILES: O=C(NC1CCN(Cc2ccc(N3CCC(NC(=O)c4cccc(-c5cccnc5)c4)CC3)nc2)CC1)c1cccc(-c2cccnc2)c1 ; "NaHB(OAc)3"]

To a dry flask was added 0.166 g (0.59 mmol) amine B, 0.190 g (0.49 mmol) of aldehyde C and 8 mL dry CH2Cl2 under an argon atmosphere. After stirring overnight at room temperature, 0.154 g (0.73 mmol) of sodium triacetoxyborohydride was added in one portion. The reaction progress was monitored by TLC (16% MeOH/CH2Cl2) with additional triacetoxyborohydride added as needed to drive the reaction to completion if needed. Upon completion, acetone was added and the mixture stirred for ca. 5 min. To the reaction mixture was added water, saturated NaHCO3, and ammonium hydroxide to adjust to pH of 9-10. The aqueous layer was extracted ca. 5 times with CH2Cl2 until no product remained in the CH2Cl2 layer. The CH2Cl2 layer was dried over Na2SO4, filtered and concentrated. The product A8 can be purified on SiO2 by eluting with a gradient of 5-16% MeOH/CH2Cl2 to give compound A8 as the free base or can be purified by reverse phase HPLC using a gradient of acetonitrile/water with 0.2% formic acid to give compound A8 as formic acid salt. Isolated yields ranged from 36-50%. HRMS(ESI+)=m/z=652.3417 (C40H42N7O2) (calc 652.33998 delta mass=−1.6 ppm).

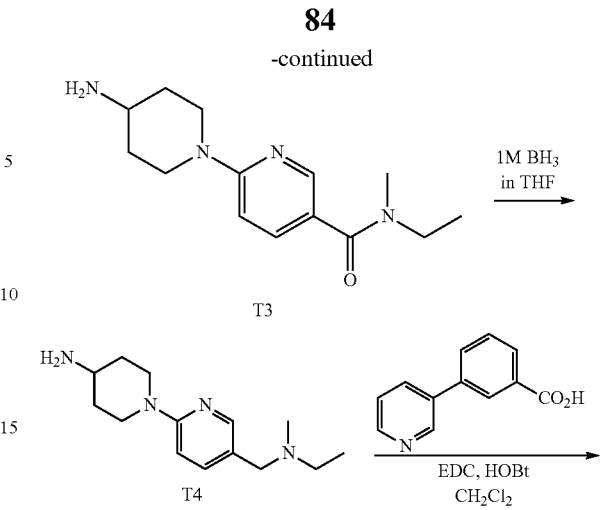

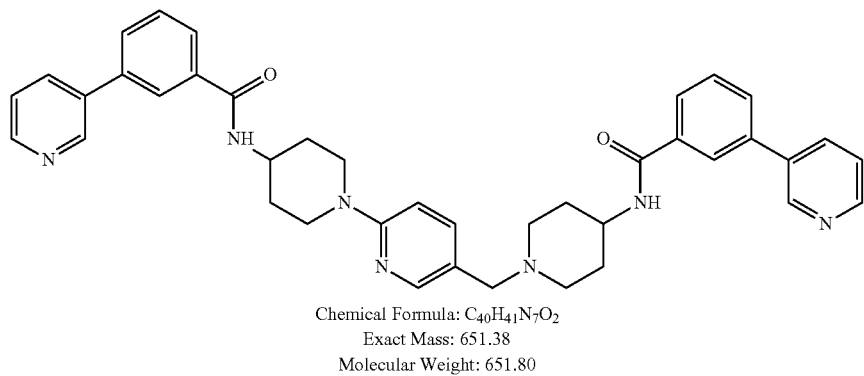 [SMILES: O=C(NC1CCN(Cc2ccc(N3CCC(NC(=O)c4cccc(-c5cccnc5)c4)CC3)nc2)CC1)c1cccc(-c2cccnc2)c1]

Chemical Formula: $C_{40}H_{41}N_7O_2$
Exact Mass: 651.38
Molecular Weight: 651.80

Synthesis of Tripos 3910 (4014-3910)

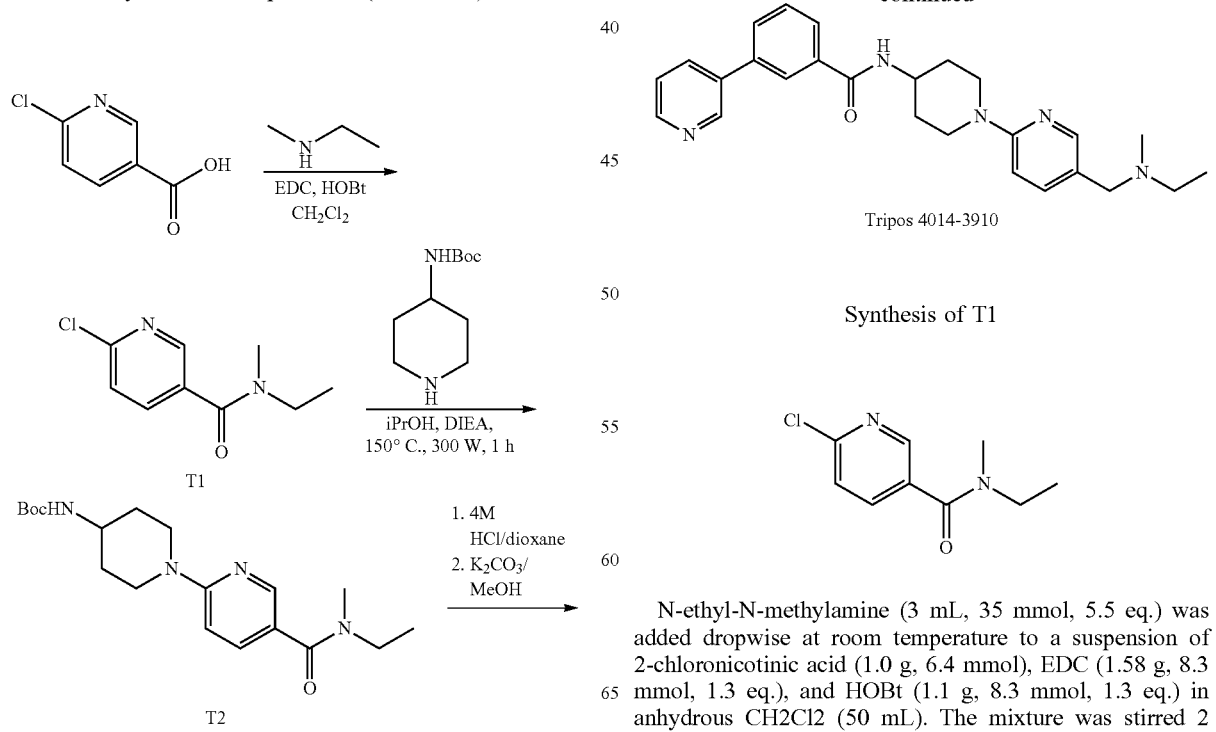

Tripos 4014-3910

Synthesis of T1

N-ethyl-N-methylamine (3 mL, 35 mmol, 5.5 eq.) was added dropwise at room temperature to a suspension of 2-chloronicotinic acid (1.0 g, 6.4 mmol), EDC (1.58 g, 8.3 mmol, 1.3 eq.), and HOBt (1.1 g, 8.3 mmol, 1.3 eq.) in anhydrous CH2Cl2 (50 mL). The mixture was stirred 2 hours at room temperature. Silica gel (~2 g) was added and the mixture was concentrated to dryness under reduced pressure. Flash column chromatography (RediSepRf SiO2 (40 g), 2% MeOH in CH2Cl2) gave the amide as a clear amber oil (950 mg, 75%). The sample exits as an equilibrating mixture of rotamers in solution.

$^1$H NMR (CDCl3, 300 MHz): δ 8.33 (s, 1H), 7.62 (s, 1H), 7.29 (s, 1H), 3.46 (m, 2H), 3.18 (m, 2H), 2.96 (s, 3H), 2.86 (s, 3H), 1.11 (m, 3H), 1.06 (m, 3H). 13C NMR (CDCl3, 75 MHz): δ 168.0, 167.4, 148.2, 147.6, 137.9, 137.5, 131.5, 124.4, 46.2, 42.7, 37.0, 32.6, 13.9, 12.2. EIMS m/z: 199 ([M+1-]+), 221 ([M+Na]+).

Synthesis of T2

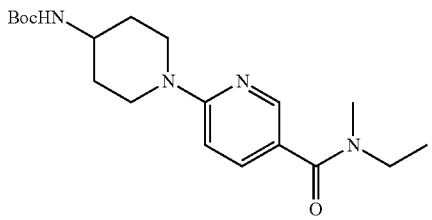 [SMILES: CCN(C)C(=O)c1ccc(N2CCC(NC(=O)OC(C)(C)C)CC2)nc1]

A mixture of N-ethyl-N-methyl-2-chloronicotinamide (0.61 g, 3.1 mmol), 4-(tert-butoxycarbonylamino)piperidine (1.8 g, 9 mmol, 3 eq.) and N,N-diisopropyl-N-ethylamine (1.2 mL, 7.1 mmol, 2.3 eq.) in EtOH (5 mL) was heated in a 10 mL microwave vessel at 150° C. (initial power setting of 300 W) for 3.5 hours. The mixture was cooled to room temperature. Silica gel (~2 g) was added and the mixture was concentrated to dryness under reduced pressure. Flash column chromatography (RediSepRf SiO2 (40 g), 2% MeOH in CH2Cl2) gave the product as a clear amber oil (0.86 g, 78%).

$^1$H NMR (CDCl3, 300 MHz): δ 8.22 (d, J=1.8 Hz, 1H), 7.54 (dd, J=1.8 Hz, 6.6 Hz, 1H), 6.59 (d, J=6.6 Hz, 1H), 4.46 (bs, 1H), 4.22 (d, J=9.9 Hz, 2H), 3.66 (s, 1H), 3.42 (bs, 2H), 3.04-2.95 (m, 2H), 2.99 (s, 3H), 1.98 (m, 2H), 1.46-1.30 (m, 4H), 1.41 (s, 9H), 1.15 (t, J=5.4 Hz, 3H). EIMS in/z: 363 ([M+H]+).

Synthesis of T3

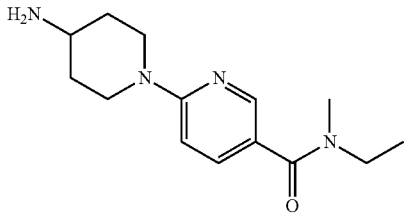 [SMILES: CCN(C)C(=O)c1ccc(N2CCC(N)CC2)nc1]

An ice bath cooled solution of the N-Boc protected amide (0.33 g, 0.90 mmol) in THF (2 mL) was treated with one portion of 4 M HCl in 1,4-dioxane (5 mL, 20 mmol, 22 eq.). Upon complete addition, the ice bath was removed and the mixture was stirred at room temperature for 1 hour. After this time analysis of the reaction mixture by TLC (5% MeOH in CH2Cl2) indicated complete consumption of starting material. The reaction mixture was concentrated to dryness under reduced pressure giving a white solid. The solid was suspended in THF (4 mL) and MeOH (20 mL) was added to dissolve all solids. Powdered K2CO3 (1 g) was added and the suspension was stirred overnight. The mixture was filtered and the silica gel (~1 g) was added to the filtrate. The filtrate was concentrated to dryness under reduced pressure. Flash column chromatography (RediSepRf SiO2 (40 g), 10% MeOH in CH2Cl2 containing 2% triethylamine) gave the product as a clear yellow oil (0.13 g, 55%). The sample which gave a single peak at multiple wavelengths with the correct mass-to-charge ration and was used immediately without further characterization. EIMS m/z: 363 ([M+H]+).

Synthesis of T4

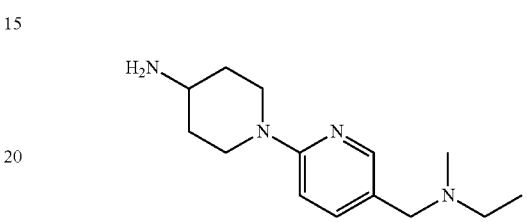

A solution of the amide (0.13 g, 0.49 mmol) in anhydrous THF (3.5 mL) was cooled in a NaCl bath. A solution of BH3 in THF (1M, 2.4 mL, 5 eq.) was added dropwise over 5 minutes. Upon complete addition, the cooling bath was removed and the mixture was stirred for 15 minutes at room temperature then heated to 45° C. (heat block temperature) for 18 hours. After this time analysis of the reaction mixture by TLC (10% MeOH in CH2Cl2) indicated complete consumption of starting material. The reaction was quenched by slow addition of MeOH and then the mixture was concentrated to dryness under reduced pressure. The resulting residue was stirred overnight in neat N,N-dimethyl-N-ethylamine (10 mL). The following morning, the reaction mixture was concentrated to dryness under reduced pressure giving the amine as a yellow oil (120 mg, 99%).

$^1$HNMR (CDCl3, 300 MHz): δ 7.93 (d, J=2.4 Hz, 1H), 7.36 (dd, J=2.4 Hz, 8.7 Hz, 1H), 6.57 (d, J=8.7 Hz, 1H), 4.13 (d, J=13.2 Hz, 2H), 3.48 (q, J=7.5 Hz, 1H), 3.27 (s, 2H), 2.86-2.75 (m, 4H), 2.67 (bs, 2H), 2.33 (q, J=7.2 Hz, 2H), 2.08 (s, 3H), 1.86-1.82 (m, 2H), 1.39-1.29 (m, 2H), 0.991 (t, J=7.2 Hz, 3H). 13C NMR (CDCl3, 75 MHz): δ 158.9, 148.6, 139.0, 122.7, 107.2, 58.6, 53.0, 50.8, 50.1, 49.2, 44.7, 41.4, 35.0, 12.4, 8.2. EIMS m/z: 249 ([M+H]+).

Synthesis of Tripos 4014-3910

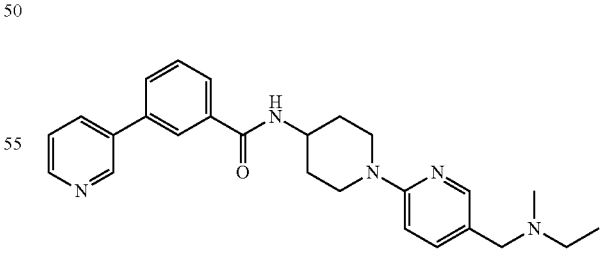

The amine (120 mg, 0.48 mmol) was dissolved in anhydrous CH2Cl2 (4 mL) then 3-(3'-pyridyl)benzoic acid (97 mg, 0.49 mmol), EDC (0.121 g, 0.64 mmol, 1.3 eq.), HOBt (86 mg, 0.64 mmol, 1.3 eq.) and N,N-diisopropyl-N-ethylamine (0.340 mL, 2.0 mmol, 4 eq.) were added sequentially. The mixture was stirred 24 hours at room temperature. Silica gel (~1 g) was added and the mixture was concentrated to dryness under reduced pressure. Flash column chromatography (RediSepRf SiO2 (24 g), 2% MeOH in CH2Cl2) gave Tripos 8 as a white amorphous solid (143 mg, 68%).

$^1$H NMR (CDCl3, 300 MHz): δ 8.86 (d, J=2.1 Hz, 1H), 8.61 (dd, J=1.5 Hz, 4.8 Hz, 1H), 8.08 (d, J=2.1 Hz, 1H), 8.01 (s, 1H), 7.91 (dt, J=2.1 Hz, 5.7 Hz, 1H), 7.83 (dd, J=2.4 Hz, 8.7 Hz, 1H), 7.78 (d, J=7.8 Hz, 1H), 7.70 (d, J=7.8 Hz, 1H), 7.54 (t, J=7.8 Hz, 1H), 7.38 (dd, J=4.8 Hz, 7.8 Hz, 1H), 6.72 (d, J=7.2 Hz, 1H), 6.32 (d, J=8.1 Hz, 1H), 4.25 (d, J=12.6 Hz, 2H), 3.83 (s, 2H), 2.99 (m, 2H), 2.85 (q, J=7.2 Hz, 2H), 2.48 (s, 3H), 2.07 (m, 2H), 1.54 (m, 2H), 1.23 (t, J=7.2 Hz, 3H), EIMS m/z: 430 ([M+H]+).

REFERENCES AND NOTES

1. Ingham, P. W.; McMahon, A. P. *Genes Dev.* 2001, 15, 3059. Dahmane, N.; Ruizi Altaba, A. *Development* 1999, 126, 3089.
2. Stecca, B.; Ruiz i Altaba, A. *J. Neurobiol.* 2005, 64, 476. Han, Y. G.; Spassky, N. et al., *Nat Neurosci.* 2008, 11, 277.
3. Machold, R.; Hayashi, S.; et al., *Neuron* 2003, 39, 937. Palma, V.; Lim, D. A., et al., *A. Development* 2005, 132, 335. Trowbridge, J. J.; Scott, M. P.; Bhatia, M. *Proc Natl Acad Sci USA* 2006, 103, 14134.
4. Beachy, P. A.; Karhadkar, S. S.; Berman, D. M. *Nature* 2004, 432, 324.
5. Taipale, J.; Beachy, P. A. *Nature* 2001, 411, 349.
6. Xie, J.; Murone, M. et al; *Nature* 1998, 391, 90.
7. Pietsch, T.; Waha, A. et al., *Cancer Res.* 1997, 57, 2085.
8. Raffel, C.; Jenkins, R. B., et al.; *Cancer Res.* 1997, 57, 842.
9. Reifenberger, J.; Wolter, M, et al *Cancer Res.* 1998, 58, 1798.
10. Taylor, M. D.; Liu, L.; et al., *Nat. Genet.* 2002, 31, 306.
11. Berman, D. M.; Karhadkar, S. S. et al., *Nature* 2003, 425, 846.
12. Thayer, S. P.; di Magliano, M. P. et al., *Nature* 2003, 425, 851.
13. Karhadkar, S. S.; Bova, G. S. et al.; *Nature* 2004, 431, 707.
14. Goodrich, L. V.; Milenkovic, L. et al.; *Science* 1997, 277, 1109.
15. Yang, Z. J.; Ellis, T. et al *Cancer Cell* 2008, 14, 135.
16. Tremblay, M. R.; Nesler, M. et al.; *Expert Opin. Ther. Patents* 2009, 19, 1039.
17. Metcalfe, C.; de Sauvage, F. S. *Cancer Res.* 2011, 71, 5057.
18. Stanton, B. Z.; Peng, L. F. *Molecular Biosyst.* 2010, 6, 44.
19. Mahindroo, N.; Punchihewa, C.; Fujii, N. *J. Med. Chem.* 2009, 52, 3829.
20. Low, J. A.; de Sauvage, F. S. *J. Clin. Oncol.* 2010, 28, 5321.
21. Ng, J. M.; Curran, T. *Nat. Rev. Cancer* 2011, 11, 493
22. Von Hoff, D. D.; LoRusso, P. M. et al *N. Eng. J. Med.* 2009, 361, 1164.
23. LoRusso, P. M.; Rudin, C. M. et al.; *Clin. Cancer Res.* 2011, 17, 2502.
24. News in Brief. *Nat. Med.* 2012, 18, 336.
25. Yauch, R. L.; Dijkgraaf, G. J. et al.; *Science* 2009, 326, 572.
26. Jiang, J.; Hui, C. *Dev. Cell* 2008, 15, 801.
27. Chen, W.; Ren, X. R. et al., *Science* 2004, 306, 2257.
28. Wang, J.; Lu, J.; Bond, M. C. et al., *Proc. Natl. Acad. Sci. U.S.A* 2010, 107, 9323.
29. Wang, J., Lu, J., Moak, Jr., et al., *Toxicol. Sci.* 2012, accepted for publication.
30. Daiss, B.; Office of Pesticide Programs, US EPA Reregistration Case No: 252, 2010.
31. Horton, M. K.; Rundle, A. et al., *Pediatrics* 2011, 127, e699.
32. Rudel, R. A.; Camann, D. E., et al., *Environ. Sci. Technol.* 2003, 37, 4543.
33. Rudin, C. M.; Hann, C. L. et al., *N. Eng. J. Med.* 2009, 361, 1173.
34. Oakley, R. H.; Laporte, S. A. et al., *J. Biol. Chem.* 1999, 274, 32248.
35. Chen, J. K.; Taipale, J.; et al., P. A. *Proc. Natl. Acad. Sci. U.S.A* 2002, 99, 14071.
36. Chen, W.; Barak, L.; Lyerly, H. K.; Wang, J. WO2009154739A2; 2009, 67 pp.
37. Pan, S.; Wu, X. et al., *ACS Med. Chem. Lett.* 2010, 1, 130.
38. Taipale, J.; Chen, J. K.; et al., *Nature* 2000, 406, 1005.
39. Wechsler-Reya, R. J.; Scott, M. P. *Neuron* 1999, 22, 103.
40. Oro, A. E.; Higgins, K. *Dev. Biol.* 2003, 255, 238.
41. Li, J. J.; Shanmugasundaram, V.; et al., *Bioorg. Med. Chem. Lett.* 2010, 20, 4932.
42. Chiang, C.; Swan, R. Z. et al., *Dev. Biol.* 1999, 205, 1.
43. Wang, L. C.; Liu, Z. Y., et al., *J. Invest. Dermatol.* 2000, 114, 901.
44. Paladini, R. D.; Saleh, J. et al., *J Invest. Dermatol.* 2005, 125, 638.
45. Tao, H. Y.; Jin, Q. H. et al., *Chem. Biol.* 2011, 18, 432.
46. Dijkgraaf, G. J. P.; Alicke, B. et al., *Cancer Res.* 2011, 71, 435.
47. Kim, J.; Lee, J. J. et al; *Proc. Natl. Acad. Sci. U.S.A* 2010, 107, 13432.
48. Lee, M. J.; Hatton, B. A., et al., J. M. *Proc. Natl. Acad. Sci. U.S.A* 2012.
49. Kinzel, O.; Alfieri, A. et al., *Bioorg. Med. Chem. Lett.* 2011, 21, 4429.

The foregoing is illustrative of the present invention, and is not to be construed as limiting thereof. The invention is defined by the following claims, with equivalents of the claims to be included therein.

What is claimed is:
1. A compound of Formula IIA or IIB:

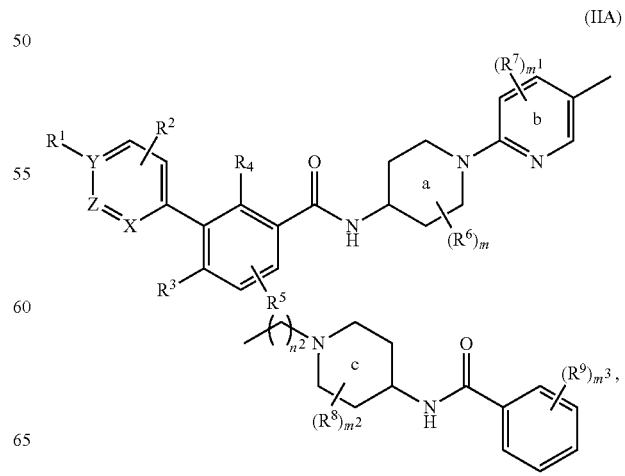

(IIA)

-continued

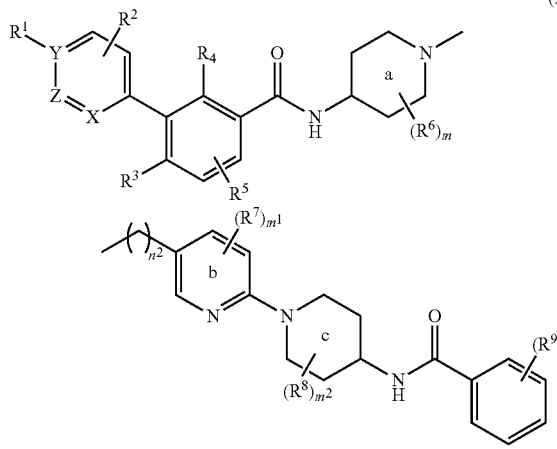

wherein:
X ix C or N;
Y is C or N;
Z is C or N;
R$^1$, R$^2$, R$^3$, R$^4$, R$^5$, each R$^6$, each R$^7$, each R$^8$, and each R$^9$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;
subject to the proviso that R$^1$ is absent when Y is N;
m, m$^1$, and m$^2$ are each integers of zero, 1, 2 or 3;
m$^3$ is an integer of zero, 1, 2 or 3;
n is an integer of from zero or 1 to 7, preferably 2;
n$^1$ is an integer of from one to six, preferably 2; and
n$^2$ is an integer of 1, 2 or 3;
or a pharmaceutically acceptable salt thereof.

2. The compound of claim 1, wherein:
X is C, Y is C, and Z is N;
X is C, Y is N, and Z is C; or
X is N, Y is C, and Z is C.

3. The compound of claim 1, wherein:
X is N, Y is N, and Z is C;
X is N, Y is C, and Z is N; or
X is C, Y is N, and Z is N.

4. The compound of claim 1, wherein said compound has the structure of Formula IIB.

5. The compound of claim 1, wherein R$^1$ is selected from the group consisting of H, alkyl, cycloalkyl, cycloalkylalkyl, cycloalkylalkenyl, heterocyclo, heterocycloalkyl, heterocycloalkenyl, aryl, arylalkyl, arylalkenyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy.

6. The compound of claim 1, wherein R$^2$ is selected from the group consisting of H, alkyl, cycloalkyl, cycloalkylalkyl, cycloalkylalkenyl, heterocyclo, heterocycloalkyl, heterocycloalkenyl, aryl, arylalkyl, arylalkenyl, heteroaryl, heteroarylalkyl, heteroarylalkenyl, alkoxy, halo, azido, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy.

7. The compound of claim 1, wherein R$^3$ is selected from the group consisting of H, alkyl, cycloalkyl, cycloalkylalkyl, cycloalkylalkenyl, heterocyclo, heterocycloalkyl, heterocycloalkenyl, aryl, arylalkyl, arylalkenyl, heteroaryl, heteroarylalkyl, heteroarylalkenyl, heteroarylalkynyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy.

8. The compound of claim 1, wherein R$^4$ is selected from the group consisting of H, alkyl, alkenyl, cycloalkyl, cycloalkylalkyl, cycloalkylalkenyl, heterocyclo, heterocycloalkyl, heterocycloalkenyl, aryl, arylalkyl, arylalkenyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy.

9. The compound of claim 1, wherein R$^5$ is selected from the group consisting of H, alkyl, alkenyl, cycloalkyl, cycloalkylalkyl, cycloalkylalkenyl, heterocyclo, heterocycloalkyl, heterocycloalkenyl, heterocycloalkynyl, aryl, arylalkyl, arylalkenyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy.

10. The compound of claim 1, wherein each R$^6$ is independently selected from the group consisting of H, alkyl, alkenyl, alkynyl, cycloalkyl, cycloalkylalkyl, cycloalkylalkenyl, heterocyclo, heterocycloalkyl, heterocycloalkenyl, aryl, arylalkyl, arylalkenyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy.

11. The compound of claim 1, wherein each R$^7$ is independently selected from the group consisting of H, alkyl, alkenyl, cycloalkyl, cycloalkylalkyl, cycloalkylalkenyl heterocyclo, heterocycloalkyl, heterocycloalkenyl, aryl, arylalkyl, arylalkenyl, arylalkynyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy.

12. The compound of claim 1, wherein each R$^8$ is independently selected from the group consisting of H, alkyl, alkenyl, cycloalkyl, cycloalkylalkyl, cycloalkylalkenyl, heterocyclo, heterocycloalkyl, heterocycloalkenyl, aryl, arylalkyl, arylalkenyl, heteroaryl, heteroarylalkyl, heteroarylalkenyl, alkoxy, halo, cyano, hydroxyl, acyl, aryloxy, alkylthio, amino, alkylamino, arylalkylamino, disubstituted amino, acylamino, acyloxy, ester, amide, sulfoxyl, sulfonyl, sulfonamide, alkoxylacylamino, and aminoacyloxy.

13. The compound of claim 1, wherein R$^1$ is selected from the group consisting of H, alkyl, alkoxy, halo, hydroxyl, acyl, amino, alkylamino, disubstituted amino, sulfoxyl, sulfonyl, sulfonamide, alkoxylacylamino, and aminoacyloxy.

14. The compound of claim 1, wherein R$^2$ is selected from the group consisting of H, alkyl, alkoxy, halo, hydroxyl, amino, alkylamino, disubstituted amino, sulfoxyl, sulfonyl, sulfonamide, alkoxylacylamino, and aminoacyloxy.

15. The compound of claim 1, wherein $R^3$ is selected from the group consisting of H, alkyl, alkenyl, alkynyl, alkoxy, halo, cyano, hydroxyl, alkylthio, amino, alkylamino, disubstituted aminosulfoxyl, sulfonyl, sulfonamide, alkoxylacylamino, and aminoacyloxy.

16. The compound of claim 1, wherein $R^4$ is selected from the group consisting of H, alkyl, alkoxy, halo, cyano, hydroxyl, alkylthio, amino, alkylamino, disubstituted amino, sulfoxyl, and sulfonyl.

17. The compound of claim 1, wherein $R^5$ is selected from the group consisting of H, alkyl, alkoxy, halo, cyano, hydroxyl, alkylthio, amino, alkylamino, disubstituted amino, sulfoxyl, and sulfonyl.

18. The compound of claim 1, wherein each $R^6$ is independently selected from the group consisting of H, alkyl halo, and hydroxyl.

19. The compound of claim 1, wherein each $R^7$ is independently selected from the group consisting of H, alkyl, alkoxy, halo, cyano, hydroxyl, amino, alkylamino, disubstituted amino sulfoxyl, and sulfonyl.

20. The compound of claim 1, wherein each $R^8$ is independently selected from the group consisting of H, alkyl, halo, and hydroxyl.

21. The compound of claim 1 having the structure of Formula IIB:

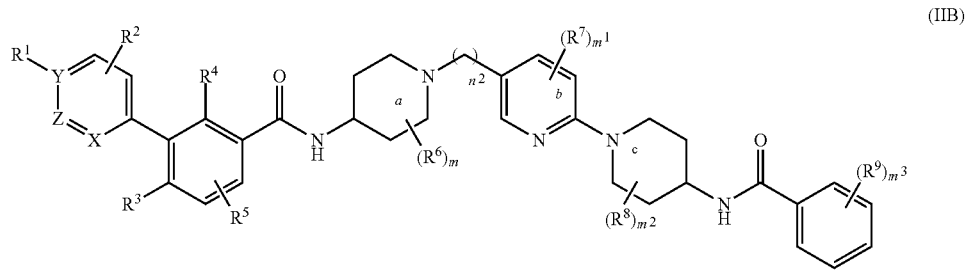

(IIB)

where:
X is C;
Y is C;
Z is N;
$n^2$ is 1;
$m^3$ is 1 or 2; and
$R^9$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy,
or a pharmaceutically acceptable salt thereof.

22. The compound of claim 21 having the structure of Formula A8:

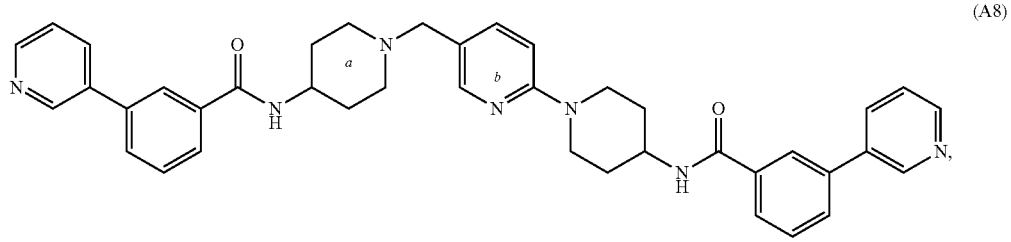 [SMILES: O=C(NC1CCN(Cc2ccc(N3CCC(NC(=O)c4cccc(-c5cccnc5)c4)CC3)nc2)CC1)c1cccc(-c2cccnc2)c1]

(A8)

or of

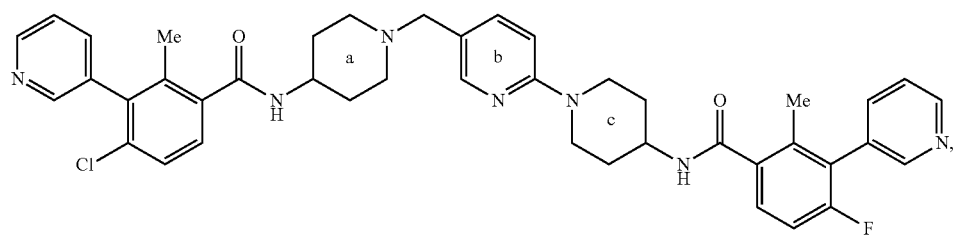 [SMILES: Cc1c(C(=O)NC2CCN(c3ccc(CN4CCC(NC(=O)c5ccc(Cl)c(-c6cccnc6)c5C)CC4)cn3)CC2)ccc(F)c1-c1cccnc1]

or a pharmaceutically acceptable salt thereof.

23. A composition comprising a compound of claim 1 in a pharmaceutically acceptable carrier.

24. A method for inhibiting unwanted proliferation of a medulloblastoma cell, comprising contacting the cell with a compound of claim 1.

25. The method of claim 24, wherein the compound is administered to an animal as part of a therapeutic application.

* * * * *

UNITED STATES PATENT AND TRADEMARK OFFICE
CERTIFICATE OF CORRECTION

| | | |
|---|---|---|
| PATENT NO. | : 9,512,106 B2 | Page 1 of 1 |
| APPLICATION NO. | : 14/405614 | |
| DATED | : December 6, 2016 | |
| INVENTOR(S) | : Chen et al. | |

It is certified that error appears in the above-identified patent and that said Letters Patent is hereby corrected as shown below:

In the Specification

Column 72, Line 16: Please correct "β-Arresting;" to read -- β-Arrestin2; --

Column 72, Line 22: Please correct "DCC, N,N-" to read -- DCC, N,N'- --

Column 72, Line 62: Please correct "β-arresting" to read -- β-arrestin2 --

Column 74, Line 47: Please correct "LDE-22537" to read -- LDE-225$_{37}$ --

In the Claims

Column 92, Claim 22, Formula A8: Please, correct the Formula below:

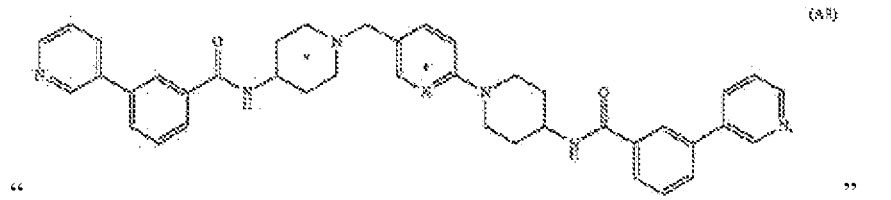

To read:

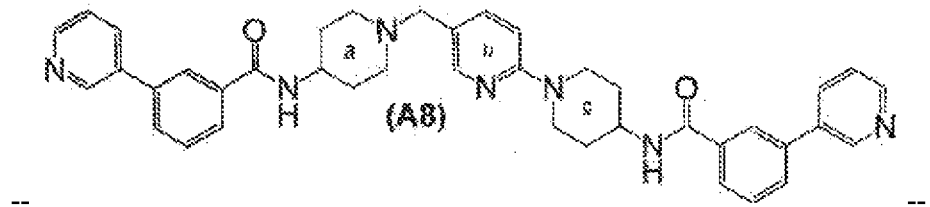

--

Signed and Sealed this
Eighteenth Day of July, 2017

Joseph Matal
*Performing the Functions and Duties of the
Under Secretary of Commerce for Intellectual Property and
Director of the United States Patent and Trademark Office*